United States Patent
Mergott et al.

(10) Patent No.: US 8,278,441 B2
(45) Date of Patent: Oct. 2, 2012

(54) BACE INHIBITORS

(75) Inventors: Dustin James Mergott, Zionsville, IN (US); Grant Mathews Vaught, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 211 days.

(21) Appl. No.: 12/830,476

(22) Filed: Jul. 6, 2010

(65) Prior Publication Data

US 2011/0009395 A1    Jan. 13, 2011

Related U.S. Application Data

(60) Provisional application No. 61/224,241, filed on Jul. 9, 2009.

(51) Int. Cl.
*C07D 513/04* (2006.01)
*A61K 31/542* (2006.01)

(52) U.S. Cl. ...................... 544/48; 514/224.2

(58) Field of Classification Search ............ 544/48; 514/224.2
See application file for complete search history.

(56) References Cited

U.S. PATENT DOCUMENTS

| 2009/0209755 A1 | 8/2009 | Suzuki et al. |
| 2010/0093999 A1 | 4/2010 | Motoki et al. |

FOREIGN PATENT DOCUMENTS

| WO | 2007049532 A1 | 5/2007 |
| WO | 2008133273 A1 | 11/2008 |
| WO | 2008133274 A1 | 11/2008 |
| WO | 2009151098 A1 | 12/2009 |

*Primary Examiner* — Kahsay T Habte
(74) *Attorney, Agent, or Firm* — Nelsen L. Lentz; Elizabeth A. Dingess-Hammond

(57) ABSTRACT

The present invention provides BACE inhibitors of Formula I:

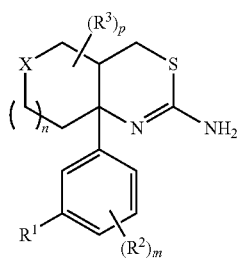

methods for their use, intermediates, and methods for their preparation.

1 Claim, No Drawings

BACE INHIBITORS

The present invention is in the field of treatment of Alzheimer's disease and other diseases and disorders involving amyloid β (Aβ) peptide, a neurotoxic and highly aggregatory peptide segment of amyloid precursor protein (APP). Complete or partial inhibition of β-secretase or β-site amyloid precursor protein-cleaving enzyme (BACE) has been shown to have a significant effect on plaque-related and plaque-dependent pathologies in mouse models suggesting that even small reductions in Aβ levels might result in long-term significant reduction in plaque burden and synaptic deficits, thus providing significant therapeutic benefits.

Currently described BACE inhibitors are peptidomimetic transition state analogs, typically containing a hydroxyethyl moiety. Although many of these compounds are potent inhibitors of BACE, their high molecular weights and low membrane permeability make them poor drug candidates. See Park and Lee, *Journal of the American Chemical Society*, 125(52), 16416-16422 (2003). There has been a progression from large peptidomimetic molecules to small molecules, such as a variety of hydroxyethylamine scaffolds as well as heterocyclic-containing scaffolds. See e.g., Durham and Shepherd, *Current Opinion in Drug Discovery & Development*, 9(6), 776-791 (2006). Certain aminothiazine compounds have been described as BACE inhibitors in WO 2007/049532, WO 2008/133273, and WO 2008/133274.

BACE inhibitors that are potent and more efficacious are necessary to provide treatments for Aβ peptide-mediated disorders, such as Alzheimer's disease. The present invention provides new potent and efficacious inhibitors of BACE.

The present invention provides compounds of Formula I:

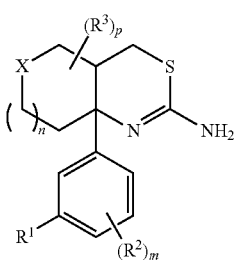

I wherein:
X is —CH$_2$— or —O—;
n is 0 or 1;
m is 0, 1, or 2;
p is 0 or 1; p must be 0 when X is —O—;
R$^1$ is —NHCOR$_4$, pyrimidinyl, pyridinyl optionally substituted with halo or phenyl optionally monosubstituted with —C$_1$-C$_3$ alkoxy;
R$^2$ is halo;
R$^3$ is —C$_1$-C$_3$ alkoxy, hydroxy, or —O—CH$_2$—O—CH$_3$; and
R$^4$ is phenyl, pyridinyl optionally substituted with halo, pyrimidinyl optionally substituted with halo, pyrizinyl, or thiazolyl;
or a pharmaceutically acceptable salt thereof.

The present invention also provides a method of treating Alzheimer's disease in a patient comprising administering to a patient in need of such treatment an effective amount of a compound of the present invention.

The present invention further provides a method of preventing the progression of mild cognitive impairment to Alzheimer's disease in a patient comprising administering to a patient in need of such treatment an effective amount of a compound of the present invention or a pharmaceutically acceptable salt thereof.

The present invention further provides a method of preventing the progression in a patient at risk for developing Alzheimer's disease comprising administering to a patient in need of such treatment an effective amount of a compound of the present invention or a pharmaceutically acceptable salt thereof.

The present invention also provides a method of inhibiting BACE in a patient comprising administering to a mammal in need of such treatment an effective amount of a compound of the present invention or a pharmaceutically acceptable salt thereof.

The present invention also provides a method for inhibiting BACE-mediated cleavage of amyloid precursor protein comprising administering to a patient in need of such treatment an effective amount of a compound of the present invention or a pharmaceutically acceptable salt thereof.

The present invention further provides a method for the inhibition of production of Aβ peptide comprising administering to a patient in need of such treatment an effective amount of a compound of the present invention or a pharmaceutically acceptable salt thereof.

The present invention also provides a pharmaceutical formulation comprising a compound of the invention or a pharmaceutically acceptable salt thereof, in combination with a pharmaceutically acceptable carrier, diluent, or excipient. In a particular embodiment, the formulation further comprises one or more other therapeutic agents.

Furthermore, this invention provides a compound of the invention or a pharmaceutically acceptable salt thereof for use in therapy, in particular for the treatment of Alzheimer's disease or for the prevention of the progression of mild cognitive impairment to Alzheimer's disease. Even furthermore, this invention provides the use of a compound of the invention or a pharmaceutically acceptable salt thereof for the manufacture of a medicament for the treatment of Alzheimer's disease. This invention also provides the use of a compound of the invention or a pharmaceutically acceptable salt thereof for the manufacture of a medicament for the prevention of the progression of mild cognitive impairment to Alzheimer's disease. The invention also provides the use of a compound of the invention or a pharmaceutically acceptable salt thereof for the manufacture of a medicament for the inhibition of BACE. The invention further provides the use of a compound of the invention or a pharmaceutically acceptable salt thereof for the manufacture of a medicament for the inhibition of production of Aβ peptide.

Additionally, this invention provides a pharmaceutical formulation adapted for the treatment of Alzheimer's disease. Furthermore, this invention provides a pharmaceutical formulation adapted for the prevention of the progression of mild cognitive impairment to Alzheimer's disease. This invention also provides a pharmaceutical formulation adapted for the inhibition of BACE.

Furthermore the present invention provides a pharmaceutical formulation adapted for the inhibition of BACE-mediated cleavage of amyloid precursor protein. The present invention also provides a pharmaceutical formulation adapted for the treatment of conditions resulting from excessive levels of Aβ peptide comprising a compound of the invention or a pharmaceutically acceptable salt thereof in combination with one or more pharmaceutically acceptable excipients, carriers, or diluents.

The general chemical terms used in the formulae above have their usual meanings. For example, the term "—C$_1$-C$_3$ alkoxy" is a —C$_1$-C$_3$ alkyl group bonded to an oxygen atom and refers to methoxy, ethoxy, propoxy, and iso-propoxy. However, "halo" refers to fluoro and chloro.

The term "nitrogen protecting group" is taken to mean a moiety that is stable to projected reaction conditions and yet may be selectively removed by reagents and reaction conditions compatible with the regenerated amine. Such groups are well known by the skilled artisan and are described in the literature. See, e.g., Greene and Wuts, *Protective Groups in Organic Synthesis*, Third Edition, Chapter 7, John Wiley and Sons Inc., (1999).

The term "inhibition of production of Aβ peptide" is taken to mean decreasing of in vivo levels of Aβ peptide in a mammal.

The term "effective amount of a compound of Formula I" is taken to mean the dose or doses of a compound of the invention required to inhibit BACE sufficiently to decrease in vivo levels of Aβ peptide in a mammal.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "prevention of the progression of mild cognitive impairment to Alzheimer's disease" includes slowing, arresting, or reversing the progression of mild cognitive impairment to Alzheimer's disease in a patient.

The skilled artisan will appreciate that compounds of the invention can exist in tautomeric forms, as depicted in FIG. (1). When any reference in this application to one of the specific tautomers of the compounds of the invention is given, it is understood to encompass both tautomeric forms and all mixtures thereof.

FIG. (1)

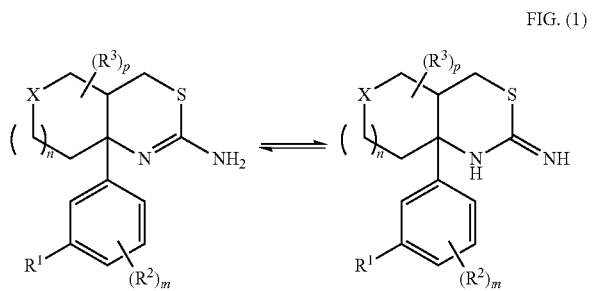

The skilled artisan will appreciate that compounds of the invention are comprised of a core that contains at least two chiral centers:

FIG. (2)

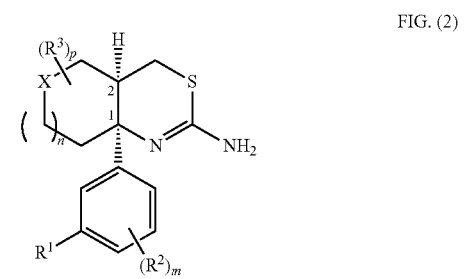

Although the present invention contemplates all individual enantiomers, as well as mixtures of the enantiomers of said compounds including racemates, the compounds with the absolute configuration at the atoms labeled 1 and 2 as illustrated in FIG. (2) are preferred compounds of the invention.

Additionally, the skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

The compounds of the present invention are amines, and accordingly react with any of a number of inorganic and organic acids to form pharmaceutically acceptable acid addition salts. Pharmaceutically acceptable salts and common methodology for preparing them are well known in the art. See, e.g., P. Stahl, et al. *Handbook of Pharmaceutical Salts: Properties, Selection and Use*, (VCHA/Wiley-VCH, 2002); S. M. Berge, et al., "Pharmaceutical Salts," *Journal of Pharmaceutical Sciences*, Vol. 66, No. 1, January 1977. Preferred pharmaceutically acceptable salts are those formed with hydrochloric acid.

Although all of the compounds of the invention are useful inhibitors of BACE, certain classes of compounds are preferred. The following paragraphs describe such preferred classes:

a) n is 0;
b) n is 1;
c) m is 0;
d) m is 1;
e) m is 2;
f) p is 0;
g) p is 1;
h) p must be 0 when X is —O—;
i) X is —O—;
j) X is —CH$_2$—;
k) R$^1$ is —NHCOR$_4$;
l) R$^1$ is pyridinyl;
m) R$^1$ is pyridinyl optionally substituted with —Cl and —F;
n) R$^1$ is pyrimidinyl;
o) R$^1$ is pyrimidinyl or pyridinyl optionally substituted with halo;
p) R$^1$ is —NHCOR$_4$, pyrimidinyl, or pyridinyl optionally substituted with —Cl and —F;
q) R$^1$ is —NHCOR$_4$, phenyl optionally substituted with —C$_1$-C$_3$ alkoxy, pyrimidinyl, or pyridinyl optionally substituted with —Cl and —F;
r) R$^1$ is —NHCOR$_4$, phenyl optionally substituted with —C$_1$-C$_3$ alkoxy, or pyrimidinyl;
s) R$^1$ is —NHCOR$_4$ or pyrimidinyl;
t) R$^2$ is fluoro;
u) R$^3$ is —C$_1$-C$_3$ alkoxy or hydroxy;
v) R$^3$ is —OCH$_3$, —OCH$_2$(CH$_3$)$_2$, or hydroxy;
w) R$^4$ is phenyl
x) R$^4$ is thiazolyl;
y) R$^4$ is pyridinyl optionally substituted with —Cl or —F, pyrimidinyl optionally substituted with halo, or pyrizinyl;

z) R⁴ is pyridinyl optionally substituted with halo, pyrimidinyl optionally substituted with halo, or thiazolyl;
aa) R⁴ is pyridinyl optionally substituted with halo, pyrimidinyl optionally substituted with halo, pyrizinyl, or thiazolyl;
bb) R⁴ is pyridinyl optionally substituted with halo or pyrimidinyl optionally substituted with halo;
cc) R⁴ is pyridinyl;
dd) R⁴ is pyridinyl optionally substituted with halo;
ee) R⁴ is pyridinyl optionally substituted with fluoro;
ff) The compound of the invention has a cis configuration at the chiral centers at the junction of the fused aminothiazine ring;
gg) The compound of the invention is a free base;
hh) The compound of the invention is a pharmaceutically acceptable salt;
ii) The compound of the invention is the hydrochloride salt.
jj) The compound of the invention is the dihydrochloride salt.
kk) The compound of the invention is the ethanesulfonate salt.
ll) The compound of the invention is the p-toluenesulfonate salt.

A preferred embodiment of the compounds of the present invention relates to compounds of the invention, wherein X is —CH₂— or —O—; n is 0 or 1; m is 0, 1, or 2; p is 0 or 1; p must be 0 when X is —O—; R¹ is —NHCOR₄, pyrimidinyl, or pyridinyl optionally substituted with halo; R² is fluoro; R³ is —C₁-C₃ alkoxy or hydroxy; R⁴ is pyridinyl optionally substituted with halo, pyrimidinyl optionally substituted with halo, pyrizinyl, or thiazolyl; or a pharmaceutically acceptable salt thereof. In said embodiment, halo is chloro or fluoro when R⁴ is pyridinyl or chloro when R⁴ is pyrimidinyl. Furthermore, in said embodiment, it is preferred that the compounds possess a cis configuration at the chiral centers at the junction of the fused aminothiazine ring; or a pharmaceutically acceptable salt thereof.

Another preferred embodiment of the compounds of the present invention relates to compounds of Formula I, wherein X is —CH₂— or —O—; n is 0 or 1; m is 0 or 1; p is 1; p must be 0 when X is —O—; R¹ is —NHCOR₄, phenyl optionally substituted with —C₁-C₃ alkoxy, pyrimidinyl, or pyridinyl optionally substituted with halo; R² is fluoro; R³ is —C₁-C₃ alkoxy or hydroxy; R⁴ is pyridinyl optionally substituted with halo, pyrimidinyl optionally substituted with halo, or thiazolyl; or a pharmaceutically acceptable salt thereof. In said embodiment, halo is chloro or fluoro when R⁴ is pyridinyl or pyrimidinyl; or a pharmaceutically acceptable salt thereof. Furthermore, in said embodiment, it is preferred that the compounds possess a cis configuration at the chiral centers at the junction of the fused aminothiazine ring; or a pharmaceutically acceptable salt thereof.

A more preferred embodiment of the compounds of the present invention relates to compounds of Formula I, wherein X is —CH₂— or —O—; n is 0 or 1; m is 0, 1, or 2; p is 0 or 1; p must be 0 when X is —O—; R¹ is —NHCOR₄ or pyrimidinyl; R² is fluoro; R³ is —C₁-C₃ alkoxy or hydroxy; R⁴ is pyridinyl optionally substituted with halo, pyrimidinyl optionally substituted with halo, pyrizinyl, or thiazolyl; or a pharmaceutically acceptable salt thereof. In said embodiment, halo is chloro or fluoro when R⁴ is pyridinyl or pyrimidinyl; or a pharmaceutically acceptable salt thereof. Furthermore, in said embodiment, it is preferred that the compounds possess a cis configuration at the chiral centers at the junction of the fused aminothiazine ring; or a pharmaceutically acceptable salt thereof.

A further embodiment of the compounds of the present invention relates to compounds of Formula I, wherein X is —CH₂— or —O—; n is 0 or 1; m is 0 or 1; p is 0 or 1; p must be 0 when X is —O—; R¹ is —NHCOR₄, phenyl optionally substituted with —C₁-C₃ alkoxy, or pyrimidinyl; R² is fluoro; R³ is —C₁-C₃ alkoxy or hydroxy; R⁴ is pyridinyl optionally substituted with halo, pyrimidinyl optionally substituted with halo, pyrizinyl, or thiazolyl; or a pharmaceutically acceptable salt thereof. In said embodiment, halo is chloro or fluoro when R⁴ is pyridinyl or pyrimidinyl. Furthermore, in said embodiment, it is preferred that the compounds possess a cis configuration at the chiral centers at the junction of the fused aminothiazine ring; or a pharmaceutically acceptable salt thereof.

A most preferred embodiment of the compounds of the present invention relates to compounds of Formula I, wherein X is —CH₂— or —O—; n is 0 or 1; m is 0 or 1; p is 0 or 1; p must be 0 when X is —O—; R¹ is —NHCOR₄ or pyrimidinyl; R² is fluoro; R³ is —C₁-C₃ alkoxy or hydroxy; R⁴ is pyridinyl optionally substituted with halo, or pyrimidinyl optionally substituted with halo; or a pharmaceutically acceptable salt thereof. In said embodiment, halo is chloro or fluoro when R⁴ is pyridinyl or pyrimidinyl; or a pharmaceutically acceptable salt thereof. Furthermore, in said embodiment, it is preferred that the compounds possess a cis configuration at the chiral centers at the junction of the fused aminothiazine ring; or a pharmaceutically acceptable salt thereof.

Another most preferred embodiment of the compounds of the present invention relates to compounds of Formula I, wherein X is —CH₂— or —O—; n is 0 or 1; m is 0 or 1; p is 0; R¹ is —NHCOR₄; R² is fluoro; R⁴ is pyridinyl optionally substituted with halo; or a pharmaceutically acceptable salt thereof. In said embodiment, halo is chloro or fluoro when R⁴ is pyridinyl; or a pharmaceutically acceptable salt thereof. Furthermore, in said embodiment, it is preferred that the compounds possess a cis configuration at the chiral centers at the junction of the fused aminothiazine ring; or a pharmaceutically acceptable salt thereof.

An especially preferred embodiment of the compounds of the present invention relates to compounds of Formula I wherein X is —O—; n is 0; m is 1; p is 0; R¹ is —NHCOR₄; R² is halo; R⁴ is pyridinyl substituted with halo; or a pharmaceutically acceptable salt thereof. In said embodiment, it is preferred that R² is fluoro; or a pharmaceutically acceptable salt thereof. Further, in said embodiment, it is preferred that the compounds possess a cis configuration at the chiral centers at the junction of the fused aminothiazine ring; or a pharmaceutically acceptable salt thereof.

A further especially preferred embodiment of the compounds of the present invention relating to compounds of Formula I is

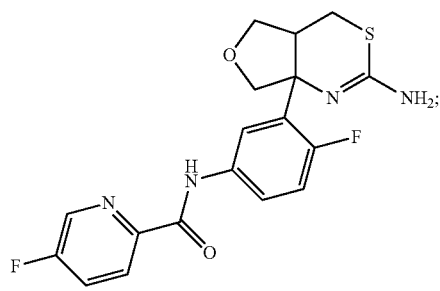

or a pharmaceutically acceptable salt thereof.

Another especially preferred embodiment of the compounds of the present invention relating to compounds of Formula I is

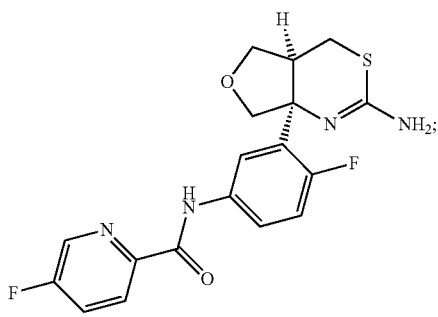

or a pharmaceutically acceptable salt thereof.

The compounds of Formula I are inhibitors of BACE. Thus, the present invention also provides a method of inhibiting BACE in a mammal that comprises administering to a mammal in need of said treatment a BACE-inhibiting amount of a compound of Formula I. It is preferred that the mammal to be treated by the administration of the compounds of Formula I is human.

As inhibitors of BACE, the compounds of the present invention are useful for suppressing the production of Aβ peptide, and therefore for the treatment of disorders resulting from excessive Aβ peptide levels due to over-production and/or reduced clearance of Aβ peptide. A further embodiment of the present invention is the use of a compound of Formula I for the manufacture of a medicament for treating a disease or condition capable of being improved or prevented by inhibition of BACE. The compounds of Formula I are therefore believed to be useful in treating or preventing Alzheimer's disease, mild cognitive impairment, Down's Syndrome, Hereditary Cerebral Hemorrhage with Amyloidosis of the Dutch-Type, cerebral amyloid angiopathy, other degenerative dementias such as: dementias of mixed vascular and degenerative origin, dementia associated with Parkinson's disease, dementia associated with progressive supranuclear palsy, dementia associated cortical basal degeneration, and diffuse Lewy body type of Alzheimer's disease.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula I, or salts thereof. The products of each step in the schemes below can be recovered by conventional methods, including extraction, evaporation, precipitation, chromatography, filtration, trituration, and crystallization.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of Formula I by methods such as chiral chromatography. Additionally, the intermediates described in the following schemes contain a number of nitrogen protecting groups. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis, supra.*

The abbreviations used herein are defined according to *Aldrichimica Acta*, Vol. 17, No. 1, 1984. Other abbreviations are defined as follows: "Prep" refers to preparation; "Ex" refers to example; "min" refers to minute or minutes; "ACN" refers to acetonitrile; "DIPEA" refers to diisopropylethylamine; "DIC" refers to diisopropylcarbodiimide; "Et$_2$O" refers to diethyl ether; "EtOAc" refers to ethyl acetate; "HATU" refers to 2-(1H-7-azabenzotriazol-1-yl)-1,1,3,3-tetramethyl uronium hexafluorophosphate methanaminium "HBTU" refers to O-benzotriazole-N,N,N',N'-tetramethyl-uronium-hexafluoro-phosphate; "HOAt" refers to 1-hydroxy-7-azabenzotriazole; "iPrOH" refers to isopropanol; "MeOH" refers to methyl alcohol or methanol; "(OEt)" refers to ethoxide; "PyBOP" refers to benzotriazol-1-yloxytripyrrolidino-phosphonium hexafluorophosphate; "PyBrop" refers to bromo-tris-pyrrolidino phosphoniumhexafluoro phosphate; "DMAP" refers to 4-dimethylaminopyridine; "PPh$_3$" refers to triphenylphosphine; "TFA" refers to trifluoroacetic acid; "THF" refers to tetrahydrofuran; "EtOH" refers to ethyl alcohol or ethanol; "SCX" refers to strong cation exchange; "T$_R$" refers to retention time; "IC$_{50}$" refers to the concentration of an agent that produces 50% of the maximal inhibitory response possible for that agent; "APP" refers to amyloid precursor protein; "DMEM" refers to Dulbecco's Modified Eagle's Medium; "F12" refers to Ham's F12 medium; "FBS" refers to Fetal Bovine Serum; "FRET" refers to fluorescence resonance energy transfer; "HEK" refers to human embryonic kidney "PDAPP" refers to platelet derived amyloid precursor protein; and "RFU" refers to relative fluorescence unit.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

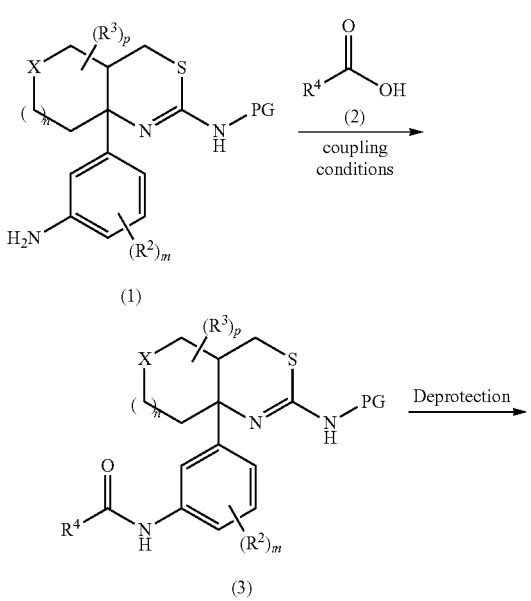

Scheme I

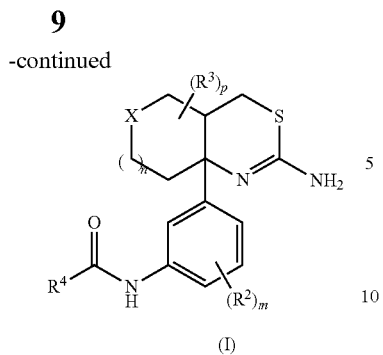

Scheme I depicts the acylation of an appropriate amine compound of formula (1) with an aryl carboxylic acid of formula (2) to give a compound of formula (I) after the deprotection of the intermediate (3). "PG" is a protecting group developed for the amino group, such as carbamates and amides. Such protecting groups are well known and appreciated in the art.

A compound of formula (1) is reacted with a compound of formula (2) under coupling conditions. One skilled in the art will recognize that there are a number of methods and reagents for amide formation resulting from the reaction of carboxylic acids and amines. For example, the reaction of an appropriate compound of formula (1) with an appropriate acid of formula (2) in the presence of a coupling reagent and an amine base, such as DIPEA or triethylamine, will give a compound of formula (3). Coupling reagents include carbodiimides, such as DCC, DIC, EDCI, and aromatic coupling reagents, such as HOBt and HOAt. Additionally, uronium or phosphonium salts of non-nucleophilic anions, such as HBTU, HATU, PyBOP, and PyBrOP can be used in place of the more traditional coupling reagents. Additives such as DMAP may be used to enhance the reactions. Alternatively, a compound of formula (1) can be acylated using substituted benzoyl chlorides in the presence of a base, such as triethylamine or pyridine.

The protecting group in intermediate (3) can be removed under acidic or basic conditions to give the compounds of formula (1). The deprotection of such compounds is well known and appreciated in the art.

In an optional step, a pharmaceutically acceptable salt of a compound of Formula (I) can be formed by reaction of an appropriate free base of Formula (I) with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art.

Scheme II

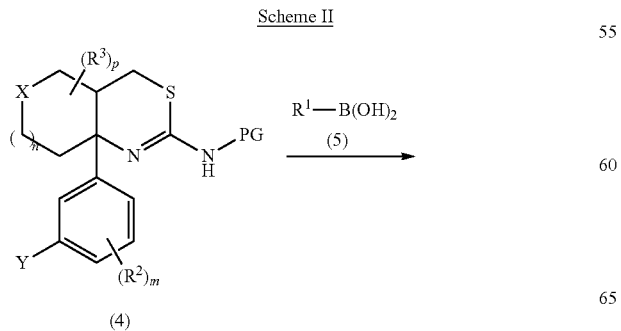

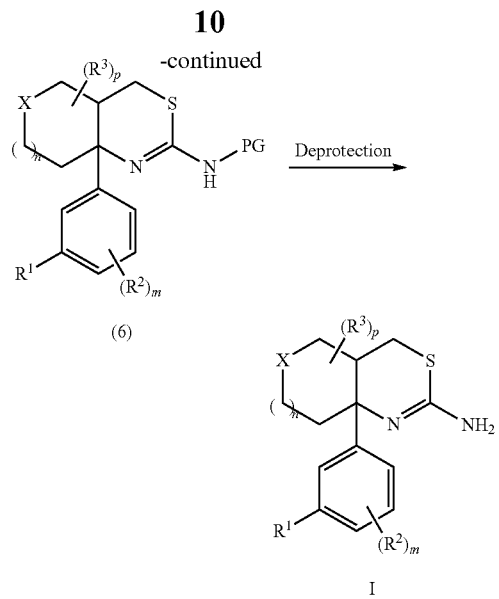

Scheme II depicts the alkylation of an appropriate compound of formula (4) with an aryl boronic acid (5) to give a compound of formula I after deprotection of the intermediate (6). Y is trifluoromethanesulfonyl or a halogen, such as Br or I. $R^1$ is an aryl group, such as phenyl, or a heteroaryl group, such as pyridinyl.

For example, an appropriate compound of formula (4) is reacted with an appropriate boronic acid (6) under Suzuki-Miyaura cross coupling conditions. The skilled artisan will recognize that there are a variety of conditions useful for facilitating such cross-coupling reactions. Accordingly, a suitable palladium reagent includes bis(triphenylphosphine) palladium(II) chloride, tris(dibenzylideneacetone)dipalladium (0) with tricyclohexylphosphine, (1,1'-bis(diphenylphosphino)ferrocene)palladium(II) chloride, palladium tetrakistriphenylphosphine, or palladium(II) acetate. A suitable base includes cesium carbonate, sodium carbonate, potassium carbonate, or potassium phosphate tribasic monohydrate.

The protecting group can be removed under acidic or basic conditions to give bi-aryl compounds of formula I. The deprotection of such compounds is well known and appreciated in the art.

Scheme III

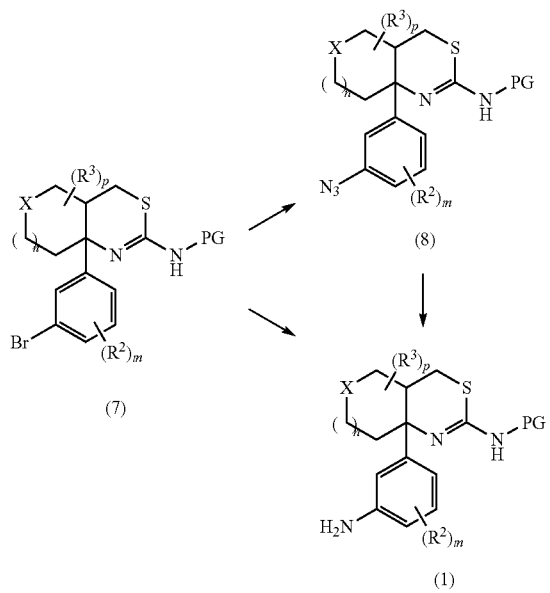

Scheme III depicts two variations to prepare the primary amine (1) starting from an appropriate aryl bromide (7).

In one variation, azido-dehalogenation is performed on the appropriate aryl bromide (7) in the presence of an azide source, such as sodium azide. Such azido-dehalogenation reactions are well known and appreciated in the art. Reduction of the resulting azide (8) to the primary amine (1) may be effected by using a number of reducing agents well known in the art, such as LiAlH$_4$, NaBH$_4$, PPh$_3$, or via hydrogenation conditions that are well known and described in the art.

Alternatively, the appropriate primary amine (1) can be prepared directly by reacting an appropriate aryl bromide (7) with an ammonia surrogate, such as trifluoroacetamide in the presence of a catalyst, such as copper iodide, a base, such as potassium carbonate, and a ligand, such as (+/-) trans N,N'-dimethyl 1,2-cyclohexanediamine. Such reactions are well known and appreciated in the art.

As will be readily appreciated, compounds of formula (7) can be promptly prepared by methods similar to those described herein by procedures that are well-known and established in the art. As will be readily understood, the steps to prepare the compounds of formula I are dependent upon the particular compound being synthesized, the starting compound, and the relative lability of the substituted moieties.

PREPARATIONS AND EXAMPLES

The following preparations and examples further illustrate the invention.

The names for the compounds of the present invention are provided by ChemDraw® Ultra, version 10.0.

The mass spectrometry data, unless specified otherwise, is obtained via LC/MS: Phenomenex Gemini C$_{18}$ (2.0×50 μm, 3.5 nm) column at a temperature of 50° C.+/-10° C. with a flow rate of 1 mL/min. The elution system is 5 to 100% ACN w/0.1% ammonium hydroxide for 7.0 minutes then held at 100% ACN for 1.0 minute coupled with electrospray ionization (100-800 amu scan range; 0.2 amu step; 80 v Fragmentor; 1.0 gain; 80 threshold).

The gas chromatography data unless specified otherwise is obtained via GC/MS: Agilent gas chromatography DB-5 ms (0.25 mm×15 m×0.25 nm) with a temperature program of 60-280° C. in 7.3 minutes then held at 280° C. for 2.0 minutes and a split ratio of 20:1.

Preparation 1 tert-Butyl 2-(allyloxy)acetate

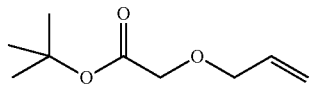

Tetrabutylammonium hydrogenosulfate (470 g, 1.40 mol) is added to a solution of sodium hydroxide (6.6 Kg, 165 mol) in water (14 L) and toluene (14 L) at 20° C. Allyl alcohol (801.5 g, 13.8 mol) is added and the mixture is stirred at 20° C. for 1 h. The mixture is cooled to 5° C., and tert-butyl 2-bromoacetate (4 Kg, 20.5 mol) is added slowly maintaining the internal temperature below 15° C. The reaction mixture is stirred at room temperature for 16 h. The mixture is diluted with water (12 L) and hexanes (12 L) and the organic phase is separated. The aqueous phase is extracted with MTBE (5 L). The combined organic phase is dried over magnesium sulfate, filtered, and concentrated to afford the title compound as colorless oil (2.6 Kg, 100%). ES/MS m/e: 173 (M+1).

Preparation 2

2-(Allyloxy)acetic acid

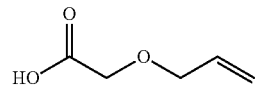

Tert-butyl 2-(allyloxy)acetate (2.6 Kg, 15.1 mol) is added to dichloromethane (14 L). 4 M HCl in dioxane (14 L) is added in one portion and the solution is stirred at 25° C. for 16 h. The solvent is removed under reduced pressure and the residue is dried under vacuum at room temperature to afford the title compound (2.2 Kg, 100%). ES/MS m/e: 117 (M+1).

Preparation 3

2-(Allyloxy)-N-methoxy-N-methylacetamide

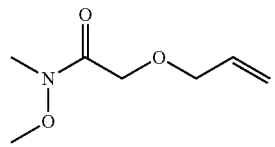

Thionyl chloride (1.5 L) is added in one portion to a solution of 2-(allyloxy)acetic acid (2.2 Kg, 18.9 mol) in toluene (3.0 L), and the mixture is heated at 65° C. under a nitrogen atmosphere for 1 h. The mixture is cooled to room temperature and is added to a solution of N,O-dimethylhydroxylamine hydrochloride (2.1 Kg, 21.5 mol) and N-methyl morpholine (6.5 L, 59.2 mol) in dichloromethane (19 L) at 5° C. The reaction mixture is stirred at 25° C. for 16 h. Water is added, and the reaction mixture is extracted with dichloromethane. The combined organic phase is collected and washed with 1 M HCl (6 L), dried over magnesium sulfate and concentrated under reduced pressure. The residue is purified by silica gel chromatography eluting with ethyl acetate in hexanes to afford the title compound (1.49 Kg, 50%). ES/MS m/e: 160 (M+1).

Preparation 4

2-(Allyloxy)-1-(5-bromo-2-fluorophenyl)ethanone

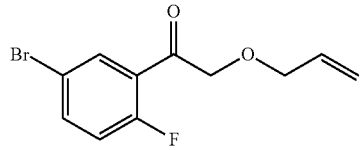

To a stirred -72° C. solution of 4-bromo-1-fluoro-2-iodobenzene (130.4 g, 433.5 mmol) in tetrahydrofuran (722 mL) is added 2.5 M butyl lithium in hexane (173.4 mL, 433.5 mmol) under a nitrogen atmosphere over 40 min. The reaction is stirred for 30 minutes at -72° C. and 2-(allyloxy)-N-methoxy-N-methylacetamide (57.5 g, 361.2 mmol) in tetrahydrofuran (115 mL) is added dropwise for 35 minutes. After 45 min at −72° C., the cooling bath is removed and mixture is warmed to 25° C. The reaction is quenched with saturated aqueous NH$_4$Cl (500 mL), diluted with water (300 mL) and extracted three times with ethyl acetate. Organics are combined, dried over magnesium sulfate, filtered, and the solvent is removed under reduced pressure. The residue is purified by silica gel chromatography using a linear gradient of 5% to 10% ethyl acetate in hexanes to give the title compound (63 g, 64%). ES/MS m/e ($^{79}$Br/$^{81}$Br) 273/275 (M+1).

The following compounds in Table 1 are prepared essentially as described in the preparation of 2-(allyloxy)-1-(5-bromo-2-fluorophenyl)ethanone.

TABLE 1

| Prep | Chemical name | NMR or ES/MS (m/e) |
|---|---|---|
| 4a | 2-(Allyloxy)-1-(3-bromophenyl)ethanone | NMR[1] |
| 4b | 2-(Allyloxy)-1-(3-bromo-5-fluorophenyl)ethanone | ($^{79}$Br/$^{81}$Br) 271/273 (M − 1) |
| 4c | 2-(Allyloxy)-1-(5-bromo-2,4-difluorophenyl)ethanone[2] | ($^{79}$Br/$^{81}$Br) 291/293 (M + 1) |
| 4d | 2-(Allyloxy)-1-(3-bromo-4-fluorophenyl)ethanone; 2-(allyloxy)-1-(2-fluoro-5-iodophenyl)ethanone[3] | Isomer 1: ($^{79}$Br/$^{81}$Br) 273/275 (M + 1); Isomer 2: 593 (M + 1) |

$^1$H NMR (400 MHz, CDCl$_3$): 8.06 (t, J = 1.6 Hz, 1H), 7.86-7.84 (m, 1H), 7.71-7.68 (m, 1H), 7.34 (t, J = 7.9 Hz, 1H), 5.98-5.91 (m, 1H), 5.34-5.23 (m, 2H), 4.69 (s, 2H), 4.14-4.11 (m, 2H).
[2]Diethyl ether is utilized instead of THF as the reaction solvent.
[3]3:1 Toluene:hexane is utilized instead of THF as the reaction solvent. Compounds are recovered as a mixture Preparation 5

2-(Allyloxy)-1-(5-bromo-2-fluorophenyl)ethanone oxime

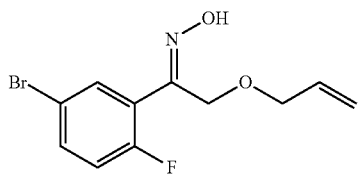

To a solution of 2-(allyloxy)-1-(5-bromo-2-fluorophenyl) ethanone (118 g, 432.1 mmol) in ethanol (1.7 L) is added hydroxylamine hydrochloride (34.5 g, 496.9 mmol) and sodium ethanoate (40.8 g, 496.9 mmol) at 25° C. The reaction is heated at 70° C. for 1 hr. The reaction is cooled and the solvent is removed under reduced pressure. The residue is washed with water (1 L) and is extracted three times with dichloromethane (3×500 mL). The organic phase is dried over magnesium sulfate, filtered, and the solvent is removed under reduced pressure, to obtain the title compound as a mixture of two possible oximes (120 g, 96%). ES/MS m/e ($^{79}$Br/$^{81}$Br) 288, 290 (M+1).

The following compounds in Table 2 are prepared essentially as described in the preparation of 2-(allyloxy)-1-(5-bromo-2-fluorophenyl)ethanone oxime.

TABLE 2

| Prep | Chemical name | ES/MS (m/e) (M + 1) |
|---|---|---|
| 5a | (E,Z)-2-(Allyloxy)-1-(3-bromophenyl)ethanone oxime | ($^{79}$Br/$^{81}$Br) 270/272 |
| 5b | (E,Z)-2-(Allyloxy)-1-(3-bromo-5-fluorophenyl)ethanone oxime | ($^{79}$Br/$^{81}$Br) 288/290 |
| 5c | (E,Z)-2-(Allyloxy)-1-(5-bromo-2,4-difluorophenyl)ethanone oxime | ($^{79}$Br/$^{81}$Br) 306/308 |
| 5d | (E,Z)-2-(Allyloxy)-1-(3-bromo-4-fluorophenyl)ethanone oxime; (E,Z)-2-(Allyloxy)-1-(2-fluoro-5-iodophenyl)ethanone oxime[4] | Isomer 1: ($^{79}$Br/$^{81}$Br) 288/290; Isomer 2: 336 |

[4]Compounds are recovered as a mixture.

Preparation 6

Racemic (3aSR,6aSR)-6a-(5-Bromo-2-fluorophenyl) hexahydrofuro[3,4-c]isoxazole

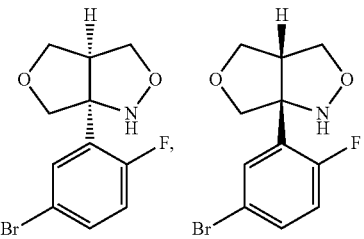

A solution of 2-(allyloxy)-1-(5-bromo-2-fluorophenyl) ethanone oxime (120 g, 417 mmol) in xylene (2 L) is heated at 140° C. for 6 h. The reaction is cooled and the solvent is removed under reduced pressure to give a solid. The solid is purified by trituration with 9:1 hexanes/MTBE to give the title compound (85 g, 72%). ES/MS m/e ($^{79}$Br/$^{81}$Br) 288, 290 (M+1).

The following compounds in Table 3 are prepared essentially as described in the preparation of racemic (3aSR, 6aSR)-6a-(5-bromo-2-fluorophenyl)hexahydrofuro[3,4-c] isoxazole.

TABLE 3

| Prep | Chemical name | ES/MS (m/e) (M + 1) |
|---|---|---|
| 6a | Racemic (3aSR,6aSR)-6a-(3-Bromophenyl)hexahydrofuro[3,4-c]isoxazole | ($^{79}$Br/$^{81}$Br) 270/272 |
| 6b | Racemic (3aSR,6aSR)-6a-(3-Bromo-5-fluorophenyl)hexahydrofuro[3,4-c]isoxazole | ($^{79}$Br/$^{81}$Br) 288/290 |
| 6c | Racemic (3aSR,6aSR)-6a-(5-Bromo-2,4-difluorophenyl)hexahydrofuro[3,4-c]isoxazole[5] | ($^{79}$Br/$^{81}$Br) 306/308 |
| 6d | Racemic (3aSR,6aSR)-6a-(3-Bromo-4-fluorophenyl)hexahydrofuro[3,4-c]isoxazole; Racemic (3aSR,6aSR)-6a-(2-Fluoro-5-iodophenyl)hexahydrofuro[3,4-c]isoxazole[5, 6] | Isomer 1: ($^{79}$Br/$^{81}$Br) 288/290; Isomer 2: 336 |

[5]This reaction is performed in toluene for 18 hours at 150° C. in a sealed tube.
[6]Compounds are recovered as a mixture.

Preparation 7

Racemic ((3RS,4SR)-4-Amino-4-(5-bromo-2-fluorophenyl)tetrahydrofuran-3-yl)methanol

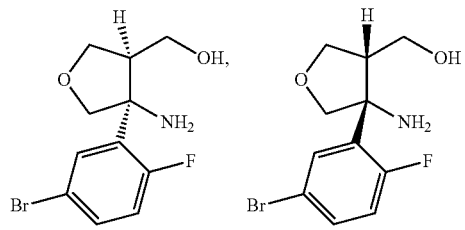

Zinc powder (190 g, 2.91 mol) is added to a mixture of racemic (3aSR,6aSR)-6a-(5-bromo-2-fluorophenyl)hexahydrofuro[3,4-c]isoxazole (84 g, 290 mmol) in acetic acid (1.4 L) at a rate maintaining the temperature below 30° C. The reaction is heated at 40° C. for 5 h. The reaction is cooled to room temperature and is filtered through a pad of diatomaceous earth, washed with acetic acid and water (200 mL). The solvent is removed under reduced pressure. Water (500 mL) is added to the residue, and the pH is adjusted to pH 10 with 2 M aqueous sodium hydroxide. The basic aqueous suspension is extracted three times with 15% isopropyl alcohol in dichloromethane (3×500 mL). The combined organic layer is dried over magnesium sulfate and the solvent is removed under reduced pressure to give the title compound as a white solid (73.0 g, 86%). ES/MS m/e ($^{79}$Br/$^{81}$Br) 290, 292 (M+1).

The following compounds in Table 4 are prepared essentially as described in the preparation of racemic ((3RS,4SR)-4-amino-4-(5-bromo-2-fluorophenyl)tetrahydrofuran-3-yl)methanol.

TABLE 4

| Prep | Chemical name | ES/MS (m/e) (M + 1) |
|---|---|---|
| 7a | Racemic ((3RS,4SR)-4-Amino-4-(3-bromophenyl)tetrahydrofuran-3-yl)methanol | ($^{79}$Br/$^{81}$Br) 272/274 |
| 7b | Racemic ((3RS,4SR)-4-Amino-4-(3-bromo-5-fluorophenyl)tetrahydrofuran-3-yl)methanol | ($^{79}$Br/$^{81}$Br) 290/292 |
| 7c | Racemic ((3RS,4SR)-4-Amino-4-(5-bromo-2,4-difluorophenyl)tetrahydrofuran-3-yl)methanol | ($^{79}$Br/$^{81}$Br) 308/310 |
| 7d | Racemic ((3RS,4SR)-4-Amino-4-(3-bromo-4-fluorophenyl)tetrahydrofuran-3-yl)methanol; racemic ((3RS,4SR)-4-amino-4-(2-fluoro-5-iodophenyl)tetrahydrofuran-3-yl)methanol[7] | Isomer 1: ($^{79}$Br/$^{81}$Br) 290/292; Isomer 2: 338 |

[7]20 equivalents of zinc dust are used in 0.06 M acetic acid. Compounds are recovered as a mixture.

Preparation 8

Racemic N-((3SR,4RS)-3-(5-Bromo-2-fluorophenyl)-4-(hydroxymethyl)tetrahydrofuran-3-ylcarbamothioyl)benzamide

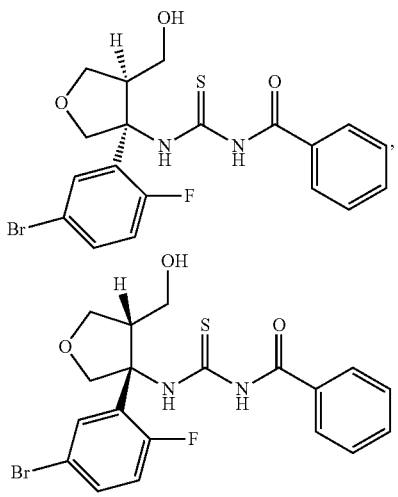

To a solution of racemic ((3RS,4SR)-4-amino-4-(5-bromo-2-fluorophenyl)tetrahydrofuran-3-yl)methanol (75 g, 259 mmol) in tetrahydrofuran (1.3 L) at 25° C. under a nitrogen atmosphere is added dropwise bis(trimethylsilyl)trifluoroacetamide (76.3 mL, 259 mmol) keeping the internal temperature below 30° C. The reaction is stirred at 25° C. for 30 minutes. Benzoyl isothiocyanate (38.4 mL, 284 mmol) is added over 10 minutes keeping internal temperature below 35° C. and the reaction is stirred at 25° C. for 30 min. The reaction mixture is diluted with ethyl acetate (500 mL) and is washed three times with 1 N HCl (3×500 mL), followed by water and brine. The solution is dried over magnesium sulfate and the solvent is removed under reduced pressure. The residue is purified by silica gel chromatography using a linear gradient of 25% to 50% ethyl acetate in hexanes to give the title compound (110 g, 94%). ES/MS m/e ($^{79}$Br/$^{81}$Br) 453, 455 (M+1).

The following compounds in Table 5 are prepared essentially as described in the preparation of racemic N-((3SR,4RS)-3-(5-bromo-2-fluorophenyl)-4-(hydroxymethyl)tetrahydrofuran-3-ylcarbamothioyl)benzamide.

TABLE 5

| Prep | Chemical name | ES/MS (m/e) (M + 1) |
|---|---|---|
| 8a | Racemic N-((3SR,4RS)-3-(3-Bromophenyl)-4-(hydroxymethyl)tetrahydrofuran-3-ylcarbamothioyl)benzamide | ($^{79}$Br/$^{81}$Br) 435/437 |
| 8b | Racemic N-((3SR,4RS)-3-(3-Bromo-5-fluorophenyl)-4-(hydroxymethyl)tetrahydrofuran-3-ylcarbamothioyl)benzamide | ($^{79}$Br/$^{81}$Br) 453/455 |
| 8c | Racemic N-((3SR,4RS)-3-(5-Bromo-2,4-difluorophenyl)-4-(hydroxymethyl)tetrahydrofuran-3-ylcarbamothioyl)benzamide | ($^{79}$Br/$^{81}$Br) 471/473 |
| 8d | Racemic N-((3SR,4RS)-3-(3-Bromo-4-fluorophenyl)-4-(hydroxymethyl)tetrahydrofuran-3-ylcarbamothioyl)benzamide; racemic N-((3SR,4RS)-3-(2-Fluoro-5-iodophenyl)-4-(hydroxymethyl)tetrahydrofuran-3-ylcarbamothioyl)benzamide[8] | Isomer 1: ($^{79}$Br/$^{81}$Br) 453/455; Isomer 2: 501 |

[8]Compounds are recovered as a mixture.

Preparation 9

Racemic N-((4aSR,7aSR)-7a-(5-Bromo-2-fluorophenyl)-4a,5,7,7a-tetrahydro-4H-furo[3,4-d][1,3]thiazin-2-yl)benzamide

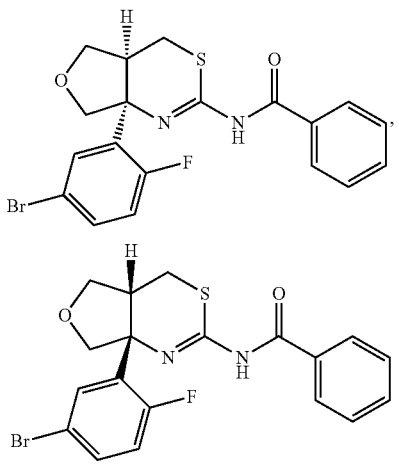

To a 15° C. mixture of racemic N-((3SR,4RS)-3-(5-bromo-2-fluorophenyl)-4-(hydroxymethyl)tetrahydrofuran-3-ylcarbamothioyl)benzamide (110 g, 243 mmol) and triphenylphosphine (76.4 g, 291 mmol) in tetrahydrofuran (970 mL) is added di-tert-butyl azodicarboxylate (67.1 g, 291 mmol) in 3 portions over 10 minutes keeping internal temperature below 25° C. After the addition, the reaction mixture is stirred at 25° C. for 1 hour. The solvent is removed under reduced pressure and the residue is purified by silica gel chromatography using a linear gradient of 14% to 33% ethyl acetate in hexanes to give the title compound (80 g, 76%). ES/MS m/e ($^{79}$Br/$^{81}$Br) 435, 437 (M+1).

The following compounds in Table 6 are prepared essentially as described in the preparation of racemic N-((4aSR,7aSR)-7a-(5-bromo-2-fluorophenyl)-4a,5,7,7a-tetrahydro-4H-furo[3,4-d][1,3]thiazin-2-yl)benzamide.

TABLE 6

| Prep | Chemical name | ES/MS (m/e) (M + 1) |
|---|---|---|
| 9a | Racemic N-((4aSR,7aSR)-7a-(3-Bromophenyl)-4a,5,7,7a-tetrahydro-4H-furo[3,4-d][1,3]thiazin-2-yl)benzamide | ($^{79}$Br/$^{81}$Br) 417/419 |
| 9b | Racemic N-((4aSR,7aSR)-7a-(3-Bromo-5-fluorophenyl)-4a,5,7,7a-tetrahydro-4H-furo[3,4-d][1,3]thiazin-2-yl)benzamide | ($^{79}$Br/$^{81}$Br) 435/437 |
| 9c | Racemic N-((4aSR,7aSR)-7a-(5-Bromo-2,4-difluorophenyl)-4a,5,7,7a-tetrahydro-4H-furo[3,4-d][1,3]thiazin-2-yl)benzamide[9] | ($^{79}$Br/$^{81}$Br) 453/455 |
| 9d | Racemic N-((4aSR,7aSR)-7a-(3-Bromo-4-fluorophenyl)-4a,5,7,7a-tetrahydro-4H-furo[3,4-d][1,3]thiazin-2-yl)benzamide; racemic N-((4aSR,7aSR)-7a-(2-Fluoro-5-iodophenyl)-4a,5,7,7a-tetrahydro-4H-furo[3,4-d][1,3]thiazin-2-yl)benzamide[10] | Isomer 1: ($^{79}$Br/$^{81}$Br) 435/437; Isomer 2: 483 |

[9]Purified by radial chromatography eluting with 10% to 15% ethyl acetate in hexane.
[10]Compounds are recovered as a mixture.

Preparation 10

N-((4aS,7aS)-7a-(5-Bromo-2-fluorophenyl)-4a,5,7,7a-tetrahydro-4H-furo[3,4-d][1,3]thiazin-2-yl)benzamide

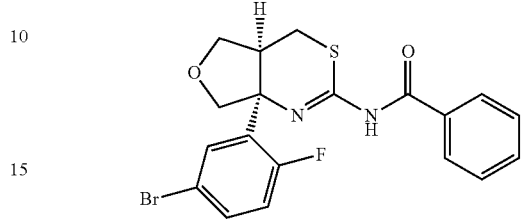

Racemic N-((4aSR,7aSR)— (7a(5-bromo-2-fluorophenyl)-4a,5,7,7a-tetrahydro-4H-furo[3,4-d][1,3]thiazin-2-yl) benzamide (108 g, 248 mmol) is purified by chiral HPLC: Chiralcel OJ-H 8×25 cm column; eluent: 90:10 (methanol: acetonitrile) with 0.2% dimethylethylamine; flow: 300 mL/min at UV 254 nm. The second eluting isomer is isolated to provide the enantiomerically enriched title compound (42.0 g, 40%). ES/MS m/e ($^{79}$Br/$^{81}$Br) 434.9/436.9 (M+1).

The following compounds in Table 7 are prepared essentially as described in the preparation of N-((4aS,7aS)-7a-(5-bromo-2-fluorophenyl)-4a,5,7,7a-tetrahydro-4H-furo[3,4-d][1,3]thiazin-2-yl)benzamide.

TABLE 7

| Prep | Chemical name | ES/MS (m/e) (M + 1) |
|---|---|---|
| 10a | N-((4aS,7aS)-7a-(3-Bromophenyl)-4a,5,7,7a-tetrahydro-4H-furo[3,4-d][1,3]thiazin-2-yl)benzamide | ($^{79}$Br/$^{81}$Br) 417/419 |
| 10b | N-((4aS,7aS)-7a-(3-Bromo-5-fluorophenyl)-4a,5,7,7a-tetrahydro-4H-furo[3,4-d][1,3]thiazin-2-yl)benzamide | ($^{79}$Br/$^{81}$Br) 435/437 |
| 10c | N-((4aS,7aS)-7a-(5-Bromo-2,4-difluorophenyl)-4a,5,7,7a-tetrahydro-4H-furo[3,4-d][1,3]thiazin-2-yl)benzamide | ($^{79}$Br/$^{81}$Br) 453/455 |

Preparation 11

Racemic (4aSR,7aSR)-7a-(5-Bromo-2-fluorophenyl)-4a,5,7,7a-tetrahydro-4H-furo[3,4-d][1,3]thiazin-2-amine

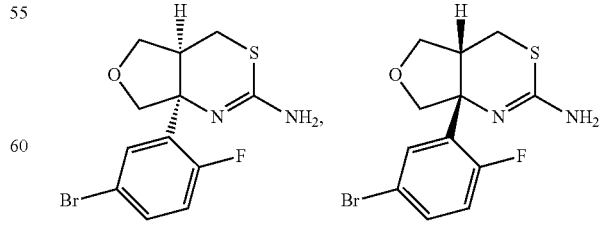

5 N Aqueous hydrochloric acid (158 mL) is added to N-(7a-(5-bromo-2-fluorophenyl)-4a,5,7,7a-tetrahydro-4H-furo[3,4-d][1,3]thiazin-2-yl)benzamide (16.35 g, 7.89 mmol) and the mixture is heated to 90° C. After 18 hours, the mixture is allowed to cool to ambient temperature and washed with dichloromethane. The organic layer is extracted once with 5 N aqueous hydrochloric acid. The pH of the aqueous layer is adjusted to basic with 50% aqueous sodium hydroxide and is extracted twice with 10% isopropyl alcohol:dichloromethane. The organic layer is concentrated under reduced pressure. The resulting residue is purified by radial chromatography eluting with 2% to 5% 7 N ammonia in methanol: dichloromethane to give the title compound (2.23 g, 47%). ES/MS m/e ($^{79}$Br/$^{81}$Br) 331, 333 (M+1).

The following compounds in Table 8 are prepared essentially by the method of racemic (4aSR,7aSR)-7a-(5-bromo-2-fluorophenyl)-4a,5,7,7a-tetrahydro-4H-furo[3,4-d][1,3]thiazin-2-amine

TABLE 8

| Prep | Chemical name | ES/MS (m/e) (M + 1) |
|---|---|---|
| 11a | Racemic (4aSR,7aSR)-7a-(3-Bromo-4-fluorophenyl)-4a,5,7,7a-tetrahydro-4H-furo[3,4-d][1,3]thiazin-2-amine; racemic (4aSR,7aSR)-7a-(2-Fluoro-5-iodophenyl)-4a,5,7,7a-tetrahydro-4H-furo[3,4-d][1,3]thiazin-2-amine[11] | Isomer 1: ($^{79}$Br/$^{81}$Br) 331/333; Isomer 2: 379 |

[11]Compounds are recovered as a mixture.

Preparation 12

N-((4aS,7aS)-7a-(5-Amino-2-fluorophenyl)-4a,5,7,7a-tetrahydro-4H-furo[3,4-d][1,3]thiazin-2-yl)benzamide

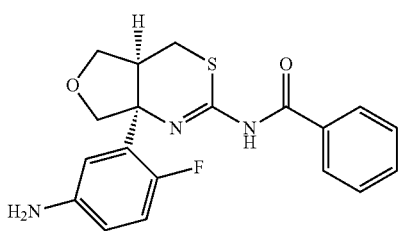

To a 2 L round bottom flask is added N-((4aS,7aS)-7a-(5-bromo-2-fluorophenyl)-4a,5,7,7a-tetrahydro-4H-furo[3,4-d][1,3]thiazin-2-yl)benzamide (35.0 g, 80.4 mmol), trifluoroacetamide (16.2 g, 143 mmol), copper(I) iodide (2.66 g, 13.7 mmol), sodium iodide (21.3 g, 141 mmol) and potassium carbonate (21.5 g, 153 mmol). The flask is capped with a septum, vacuum and back filled with nitrogen. 1,4-dioxane (731 mL) (previously degassed with vacuum-nitrogen) is added via cannula, and N,N'-dimethyl-, trans (+/−) 1,2-cyclohexanediamine (10.1 g, 70.8 mmol) is added. The mixture is placed in a preheated oil bath at 100° C. and stirred at this temperature for 19 h. The septum is replaced by a reflux condenser and a mixture of methanol (154 mL) and water (154 mL) is added through the condenser. The mixture is stirred at 100° C. for 3.5 h, cooled to 22° C., and concentrated partially under reduced pressure (to 0.6 L volume). Aqueous ammonium hydroxide (25%, 154 mL) is added and the mixture is stirred for 10 min. The mixture is extracted three times with ethyl acetate (3×500 mL) and the solvent is removed under reduced pressure. A residue is obtained that is purified by flash chromatography with a linear gradient of 50% to 75% ethyl acetate in hexane to give the title compound (14.9 g, 47%). ES/MS m/e: 372 (M+1).

Preparation 13

N-((4aS,7aS)-7a-(3-Azidophenyl)-4a,5,7,7a-tetrahydro-4H-furo[3,4-d][1,3]thiazin-2-yl)benzamide

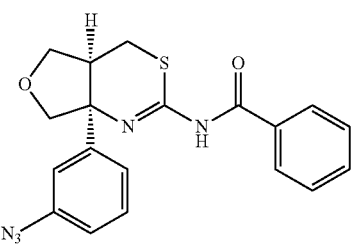

A 0.66 M solution of L-ascorbic acid is prepared by dissolving L-ascorbic acid sodium salt (0.79 g, 2.0 mmol) in water (6 mL). N-((4aS,7aS)-7a-(3-bromophenyl)-4a,5,7,7a-tetrahydro-4H-furo[3,4-d][1,3]thiazin-2-yl)benzamide (1.40 g, 3.35 mmol) and 1,2-cyclohexanediamine, N,N'-dimethyl-, trans (+/−) (162 mg, 1.11 mmol) are dissolved in ethanol (13.4 mL). Sodium azide (0.661 g, 10.1 mmol) is added. The 0.66 M aqueous L-ascorbic acid sodium salt (2.24 mL) and water (2.58 mL) are added. The reaction flask is fitted with a reflux condenser and the mixture is degassed and evacuated with nitrogen. Copper (II) sulfate pentahydrate (0.184 g, 0.738 mmol) is added and the reaction flask is heated to 80° C. and stirred for 1.5 h. The reaction mixture is cooled to room temperature and ice water is added. The reaction mixture is extracted three times with ethyl acetate. The combined organic phase is dried over sodium sulfate and the solvent is removed under reduced pressure to give a residue that is purified on silica gel with 50% ethyl acetate in hexanes to give the title compound (0.620 g, 49%). Further elution of the flash column with 100% ethyl acetate yields more title compound (0.488 g, 41%). ES/MS m/e: 380 (M+1).

The following compounds in Table 9 are prepared essentially by the method of N-((4aS,7aS)-7a-(3-azidophenyl)-4a,5,7,7a-tetrahydro-4H-furo[3,4-d][1,3]thiazin-2-yl)benzamide.

TABLE 9

| Prep | Chemical name | ES/MS (m/e) (M + 1) |
|---|---|---|
| 13a | Racemic N-((4aSR,7aSR)-7a-(3-Azidophenyl)-4a,5,7,7a-tetrahydro-4H-furo[3,4-d][1,3]thiazin-2-yl)benzamide | 380 |
| 13b | N-((4aS,7aS)-7a-(3-azido-5-fluorophenyl)-4a,5,7,7a-tetrahydro-4H-furo[3,4-d][1,3]thiazin-2-yl)benzamide | 398 |

Preparation 14

N-((4aS,7aS)-7a-(3-Aminophenyl)-4a,5,7,7a-tetrahydro-4H-furo[3,4-d][1,3]thiazin-2-yl)benzamide

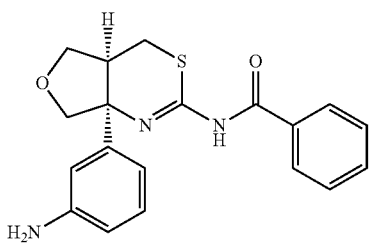

N-((4aS,7aS)-7a-(3-azidophenyl)-4a,5,7,7a-tetrahydro-4H-furo[3,4-d][1,3]thiazin-2-yl)benzamide (0.62 g, 1.63 mmol) is diluted with ethanol (10 mL) and Pd on carbon (10%, wet, 0.062 g). The mixture is degassed and stirred at room temperature under hydrogen (30 psi) overnight. The mixture is filtered through diatomaceous earth using ethanol as a rinse. The solvent is removed under reduced pressure to give the title compound, (0.106 g, 18%). ES/MS m/e: 354 (M+1).

The following compounds in Table 10 are prepared essentially by the method of N-((4aS,7aS)-7a-(3-aminophenyl)-4a,5,7,7a-tetrahydro-4H-furo[3,4-d][1,3]thiazin-2-yl)benzamide.

TABLE 10

| Prep | Chemical name | ES/MS (m/e) (M + 1) |
|---|---|---|
| 14a | Racemic N-((4aSR,7aSR)-7a-(3-Aminophenyl)-4a,5,7,7a-tetrahydro-4H-furo[3,4-d][1,3]thiazin-2-yl)benzamide | 354 |
| 14b | N-((4aS,7aS)-7a-(3-Amino-5-fluorophenyl)-4a,5,7,7a-tetrahydro-4H-furo[3,4-d][1,3]thiazin-2-yl)benzamide | 372 |

Preparation 15

N-(3-((4aS,7aS)-2-Benzamido-4a,5,7,7a-tetrahydro-4H-furo[3,4-d][1,3]thiazin-7a-yl)-4-fluorophenyl)-5-fluoropicolinamide

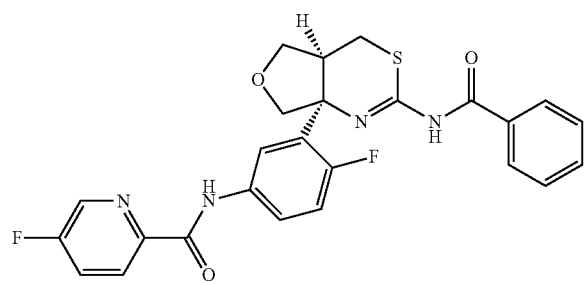

A mixture of N-((4aS,7aS)-7a-(5-amino-2-fluorophenyl)-4a,5,7,7a-tetrahydro-4H-furo[3,4-d][1,3]thiazin-2-yl)benzamide (20.4 g, 51.8 mmol), 5-fluoropicolinic acid (8.77 g, 62.2 mmol), 1-hydroxybenzotriazole hydrate (10.3 g, 67.4 mmol) and 1-(3-dimethylaminopropyl)-3-ethylcarbodiimide hydrochloride (13.2 g, 67.4 mmol) in a mixture of dichloromethane (345 mL) and DMF (6.5 mL) is stirred at 22° C. for 80 min. A solution of 2 M sodium hydroxide (129.5 mL, 259 mmol) is added and the stirring is continued for 10 min. The mixture is separated and the aqueous phase is extracted with twice with dichloromethane (2×100 mL). The organic layer is concentrated under reduced pressure and the residue is diluted with ethyl acetate (200 mL). The organic layer is washed with cooled water (2×50 mL), brine (50 mL) and filtered through a short pad of silica using 100% ethyl acetate to give title compound (23.8 g, 79%). ES/MS m/e: 495 (M+1).

The following compounds in Table 11 are prepared essentially as described in the preparation of N-(3-((4aS,7 aS)-2-benzamido-4a,5,7,7a-tetrahydro-4H-furo[3,4-d][1,3]thiazin-7a-yl)-4-fluorophenyl)-5-fluoropicolinamide.

TABLE 11

| Prep | Chemical name | ES/MS (m/e) (M + 1) |
|---|---|---|
| 15a | N-(3-((4aS,7aS)-2-Benzamido-4a,5,7,7a-tetrahydro-4H-furo[3,4-d][1,3]thiazin-7a-yl)phenyl)-5-fluoropicolinamide | 477 |
| 15b | N-(3-((4aS,7aS)-2-Benzamido-4a,5,7,7a-tetrahydro-4H-furo[3,4-d][1,3]thiazin-7a-yl)-5-fluorophenyl)-5-fluoropicolinamide | 495 |
| 15c | Racemic N-(3-((4aSR,7aSR)-2-Benzamido-4a,5,7,7a-tetrahydro-4H-furo[3,4-d][1,3]thiazin-7a-yl)phenyl)-5-fluoropicolinamide | 477 |

Preparation 16

N-(3-((4aS,7aS)-2-Amino-4a,5,7,7a-tetrahydro-4H-furo[3,4-d][1,3]thiazin-7a-yl)-4-fluorophenyl)-5-fluoropicolinamide

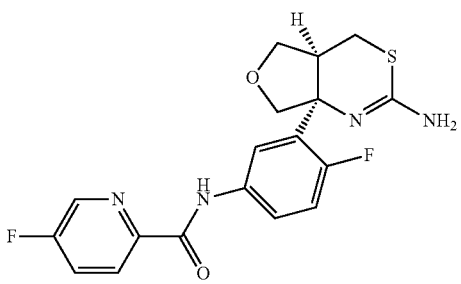

A solution of N-(3-((4aS,7aS)-2-benzamido-4a,5,7,7a-tetrahydro-4H-furo[3,4-d][1,3]thiazin-7a-yl)-4-fluorophenyl)-5-fluoropicolinamide (23.7 g 40.8 mmol), o-methylhydroxylamine hydrochloride (34.4 g, 412 mmol) and pyridine (33.3 mL) in ethanol (735 mL) is heated to 50° C. for 4 h. The mixture is concentrated. The residue is washed twice with methyl tert-butyl ether (2×250 mL) and poured into a saturated aqueous solution of sodium bicarbonate (453 mL). The suspension is shaken for 5 min and extracted with dichloromethane (1×1 L and 2×0.5 L). The organic layer is washed with water (0.5 L) dried over magnesium sulfate and the solvent is removed under reduced pressure to afford a solid. Additional solid is obtained from the aqueous phase by filtration. The solids are combined and triturated with water (300 mL) in an ultrasound bath for 30 min. The suspension is filtered off, washed with water, and dried under vacuum to give title compound (17.3 g, 100%). ES/MS m/e: 391 (M+1).

Preparation 17

1,5-Dibromo-2,4-difluorobenzene

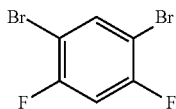

Iron powder (16.49 g, 291 mmol) is added to 1-bromo-2,4-difluorobenzene (110 mL, 968 mmol) in 1,2-dichloroethane (968 mL) in a 3-neck flask at ambient temperature under a stream of nitrogen. A solution of bromine (59.7 mL, 1.16 mol) in 1,2-dichloroethane (968 mL) is added dropwise over 1 hour and the reaction mixture is stirred at ambient temperature for 18 h. The reaction mixture is cooled to 0° C. and a saturated aqueous solution of sodium bisulfate (1.11 L, 533 mmol) is added portionwise and the mixture is separated. The aqueous phase is extracted with dichloromethane. The organic layer is washed with a saturated aqueous solution of sodium bicarbonate, water, and brine. The organic layer is dried over sodium sulfate, and the solvent is removed under reduced pressure to give a residue purified with a pad of silica using diethyl ether to give the title compound (229 g, 76%). $^1$H NMR (400 MHz, CDCl$_3$) δ 7.70 (dd, J=4.6, 6.8 Hz, 1H), 6.95-6.92 (m, 1H).

Preparation 18

4-(3-Bromophenyl)tetrahydro-2H-pyran-4-ol

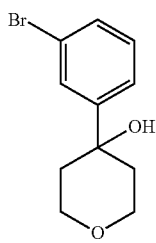

To a stirred −78° C. solution of 1,3-dibromobenzene (19.71 g, 81.05 mmol) in THF (150 mL) is added 1.6 M butyl lithium in hexane (50.66 mL, 81.05 mmol) and the reaction is stirred 10 minutes. 4H-Pyran-4-one, tetrahydro- (5.41 g, 54.04 mmol) is added dropwise and the reaction is stirred at −78° C. for 2 h. The reaction is quenched by addition of saturated aqueous ammonium chloride (25 mL) and is then diluted with minimal water and extracted with EtOAc. The organic layer is dried over Na$_2$SO$_4$ and the solvent is removed under reduced pressure to afford a residue that is purified by silica gel chromatography eluting with a linear gradient of 5% to 100% EtOAc in hexanes to give the title compound (11.18 g, 76%). GC-MS (m/e): ($^{79}$Br/$^{81}$Br) 256, 258 (M−1).

The following compounds in Table 12 are prepared essentially as described in the preparation of (4-(3-bromophenyl)tetrahydro-2H-pyran-4-ol.

TABLE 12

| Prep. No. | Chemical name | NMR or ES/MS (m/e) |
|---|---|---|
| 18a | 4-(5-Bromo-2-fluorophenyl)tetrahydro-2H-pyran-4-ol | ($^{79}$Br/$^{81}$Br) 274/276 (GC-MS) |
| 18b | 4-(3-Bromo-4-fluorophenyl)tetrahydro-2H-pyran-4-ol[12] | ($^{79}$Br/$^{81}$Br) 274/276 (GC-MS) |
| 18c | 4-(5-Bromo-2,4-difluorophenyl)tetrahydro-2H-pyran-4-ol | ($^{79}$Br/$^{81}$Br) 292/294 (GC-MS) |
| 18d | 1-(3-Bromophenyl)cyclohexanol | ($^{79}$Br/$^{81}$Br) 254/256 (GC-MS) |
| 18e | 1-(4-Fluoro-3-methoxyphenyl)cyclopentanol | 192 (GC-MS) |
| 18f | 1-(3-Bromophenyl)cyclopentanol[13] | NMR[14] |

[12]2:1 toluene:hexanes is used as the reaction solvent.
[13]Diethyl ether is used as the reaction solvent.
[14]$^1$H NMR (400 MHz, CDCl$_3$) δ 7.64 (t, J = 2.0 Hz, 1H), 7.40-7.31 (m, 2H), 7.19 (t, J = 7.9 Hz, 1H), 1.99-1.82 (m, 8H).

Preparation 19

4-(3-Bromophenyl)-3,6-dihydro-2H-pyran

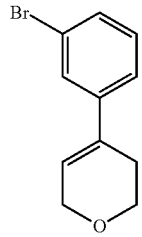

A mixture of 4-(3-bromophenyl)tetrahydro-2H-pyran-4-ol (11.17 g, 41.3 mmol) and p-toluenesulfonic acid monohydrate (0.797 g, 4.13 mmol) in toluene (100 mL) is heated to reflux for 30 minutes using a Dean-Stark trap to remove water. The reaction is diluted with water and 5 N NaOH and extracted with EtOAc. The organic layer is dried over Na$_2$SO$_4$ and the solvent is removed under reduced pressure to afford a residue that is purified on silica gel chromatography eluting with a linear gradient of 5% to 100% EtOAc in hexanes to give the title compound (8.85 g, 90%). $^1$H NMR (400 MHz, CDCl$_3$) δ 2.45-2.50 (m, 2H), 3.92 (t, 2H, J=5.71 Hz), 4.31 (q, 2H, J=3.07 Hz, J=5.71 Hz), 6.12-6.14 (m, 1H), 7.19 (t, 1H, J=7.91 Hz), 7.28-7.32 (m, 1H), 7.36-7.39 (m, 1H), 7.51 (t, 1H, J=1.76 Hz).

The following compounds in Table 13 are prepared essentially as described in the preparation of 4-(3-bromophenyl)-3,6-dihydro-2H-pyran.

TABLE 13

| Prep | Chemical name | NMR or GC-MS (m/e) |
|---|---|---|
| 19a | 4-(5-Bromo-2-fluorophenyl)-3,6-dihydro-2H-pyran | ($^{79}$Br/$^{81}$Br) 256/258 |
| 19b | 4-(3-Bromo-4-fluorophenyl)-3,6-dihydro-2H-pyran | ($^{79}$Br/$^{81}$Br) 256/258 |

TABLE 13-continued

| Prep | Chemical name | NMR or GC-MS (m/e) |
|---|---|---|
| 19c | 4-(5-Bromo-2,4-difluorophenyl)-3,6-dihydro-2H-pyran | ($^{79}$Br/$^{81}$Br) 274/276 |
| 19d | 1-Bromo-3-cyclohexenylbenzene | ($^{79}$Br/$^{81}$Br) 236/238 |
| 19e | 4-Cyclopentenyl-1-fluoro-2-methoxybenzene | 192 |
| 19f | 1-Bromo-3-cyclopentenylbenzene | NMR[15] |

[15]$^1$H NMR (400 MHz, CDCl$_3$) δ 7.55 (t, J = 2.0 Hz, 1H), 7.35-7.31 (m, 1H), 7.18-7.14 (m, 2H), 6.21-6.17 (m, 1H), 2.73-2.68 (m, 2H), 2.56-2.50 (m, 2H), 2.01 (quintet, J = 7.5 Hz, 2H).

Preparation 20

(4-(3-Bromophenyl)-3,6-dihydro-2H-pyran-3-yl)methanol

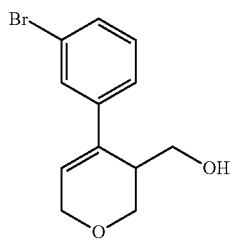

A 0° C. solution of 4-(3-bromophenyl)-3,6-dihydro-2H-pyran (0.50 g, 2.09 mmol) in CH$_2$Cl$_2$ (15 mL) is treated with paraformaldehyde (0.208 g, 2.20 mmol) and stirred for 5 minutes at 0° C. A 1 M solution of dimethylaluminum chloride in hexanes (3.03 mL, 3.03 mmol) is added drop-wise to the slurry. The reaction is warmed to room temperature and stirred for 1 hour. The reaction is cooled to 0° C. and more paraformaldehyde (0.208 g, 2.20 mmol) and 1 M solution of dimethylaluminum chloride in hexanes (3.03 mL, 3.03 mmol) is added. The reaction is warmed to room temperature and stirred overnight. The reaction is quenched by pouring into an ice/1 N HCl mixture and is extracted three times with EtOAc. The combined organic layers are dried over Na$_2$SO$_4$ and the solvent is removed under reduced pressure to afford a residue that is purified on silica gel chromatography eluting with a linear gradient of 5% to 100% EtOAc in hexanes to give the title compound (0.315 g, 53%). $^1$H NMR (400 MHz, CDCl$_3$) δ 7.50 (t, J=2.0 Hz, 1H), 7.40 (dd, J=2.2, 7.9 Hz, 1H), 7.29-7.27 (m, 1H), 7.20 (t, J=7.9 Hz, 1H), 6.11 (t, J=2.9 Hz, 1H), 4.32-4.29 (m, 2H), 4.28-4.25 (m, 1H), 3.76 (dd, J=3.1, 11.4 Hz, 1H), 3.70-3.64 (m, 2H), 2.70 (d, J=2.2 Hz, 1H), 1.89 (dd, J=4.6, 6.4 Hz, 1H).

The following compounds in Table 14 are prepared essentially as described in the preparation of (4-(3-bromophenyl)-3,6-dihydro-2H-pyran-3-yl)methanol.

TABLE 14

| Prep | Chemical name | NMR or GC-MS (m/e) (M + 1) |
|---|---|---|
| 20a | (4-(5-Bromo-2-fluorophenyl)-3,6-dihydro-2H-pyran-3-yl)methanol | ($^{79}$Br/$^{81}$Br) 286/288 |
| 20b | (4-(3-Bromo-4-fluorophenyl)-3,6-dihydro-2H-pyran-3-yl)methanol | NMR[16] |
| 20c | (4-(5-Bromo-2,4-difluorophenyl)-3,6-dihydro-2H-pyran-3-yl)methanol | NMR[17] |
| 20d | (2-(3-Bromophenyl)cyclohex-2-enyl)methanol | ($^{79}$Br/$^{81}$Br) 266/268 |
| 20e | (2-(4-Fluoro-3-methoxyphenyl)cyclopent-2-enyl)methanol | 222 |
| 20f | (2-(3-Bromophenyl)cyclopent-2-enyl)methanol | NMR[18] |

[16]$^1$H NMR (400 MHz, CDCl$_3$) δ 7.52 (dd, J = 2.2, 6.6 Hz, 1H), 7.26-7 22 (m, 1H), 7.06 (t, J = 8.4 Hz, 1H), 6.04 (t, J = 2.6 Hz, 1H), 4.28-4.22 (m, 3H), 3.73 (dd, J = 3.1, 11.4 Hz, 1H), 3.64-3.62 (m, 2H), 2.63 (d, J = 1.3 Hz, 1H), 1.88 (s, 1H).

[17]$^1$H NMR (400 MHz, CDCl$_3$) δ 7.41 (t, J = 7.7 Hz, 1H), 6.86 (dd, J = 8.4, 10.1 Hz, 1H), 5.96 (t, J = 2.6 Hz, 1H), 4.27-4.25 (m, 1H), 4.15-4.06 (m, 2H), 3.83 (dd, J = 3.5, 11.4 Hz, 1H), 3.61 (d, J = 4.8 Hz, 2H), 2.69-2.64 (m, 1H), 1.75-1.91 (s, 1H).

[18]$^1$H NMR (400 MHz, CDCl$_3$) δ 7.53 (s, 1H), 7.32 (t, J = 7.2 Hz, 2H), 7.15 (t, J = 7.9 Hz, 1H), 6.19 (s, 1H), 3.67 (dd, J = 3.7, 10.8 Hz, 1H), 3.54 (dd, J = 6.4, 10.8 Hz, 1H), 3.31 (dd, J = 1.3, 2.6 Hz, 1H), 2.57-2.47 (m, 2H), 2.23-2.13 (m, 1H), 2.02-2.02 (m, 1H).

Preparation 21

(4-(3-Bromophenyl)-3,6-dihydro-2H-pyran-3-yl)methyl methanesulfonate

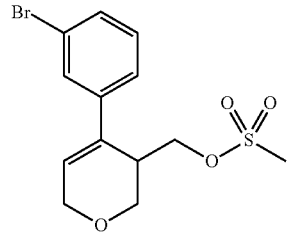

A 0° C. solution of (4-(3-bromophenyl)-3,6-dihydro-2H-pyran-3-yl)methanol (0.305 g, 1.08 mmol) in CH$_2$Cl$_2$ (10 mL) is treated with triethylamine (0.218 g, 2.15 mmol) and then methanesulfonyl chloride (0.148 g, 1.29 mmol) and the reaction is stirred at 0° C. for 30 min. The reaction is diluted with water and extracted with CH$_2$Cl$_2$. The organic layer is dried over Na$_2$SO$_4$ and the solvent is removed under reduced pressure to afford the title compound (0.432 g, 97%). $^1$H NMR (400 MHz, CDCl$_3$) δ 7.51 (t, J=1.8 Hz, 1H), 7.44-7.41 (m, 1H), 7.31-7.29 (m, 1H), 7.25-7.21 (m, 1H), 6.18 (t, J=2.6 Hz, 1H), 4.33-4.31 (m, 2H), 4.20 (dd, J=1.5, 11.6 Hz, 2H), 4.14-4.08 (m, 1H), 3.72-3.68 (m, 1H), 3.01-2.98 (m, 1H), 2.95 (s, 3H).

The following compounds in Table 15 are prepared essentially as described in the preparation of (4-(3-bromophenyl)-3,6-dihydro-2H-pyran-3-yl)methyl methanesulfonate.

TABLE 15

| Prep | Chemical name | NMR or GC-MS (m/e) (M + 1) |
|---|---|---|
| 21a | (4-(5-Bromo-2-fluorophenyl)-3,6-dihydro-2H-pyran-3-yl)methyl methanesulfonate | NMR[19] |
| 21b | (4-(3-Bromo-4-fluorophenyl)-3,6-dihydro-2H-pyran-3-yl)methyl methanesulfonate | NMR[20] |
| 21c | (4-(5-Bromo-2,4-difluorophenyl)-3,6-dihydro-2H-pyran-3-yl)methyl methanesulfonate | NMR[21] |
| 21d | (2-(3-Bromophenyl)cyclohex-2-enyl)methyl methanesulfonate | NMR[22] |
| 21e | (2-(4-Fluoro-3-methoxyphenyl)cyclopent-2-enyl)methyl methanesulfonate | 300 |
| 21f | (2-(3-Bromophenyl)cyclopent-2-enyl)methyl methanesulfonate[23] | NMR[24] |

[19]$^1$H NMR (400 MHz, CDCl$_3$) δ 7.36 (ddd, J = 8.4, 4.4, 2.6 Hz, 1H), 7.31 (dd, J = 2.6, 6.6 Hz, 1H), 6.93 (dd, J = 8.8, 10.1 Hz, 1H), 6.04 (t, J = 2.6 Hz, 1H), 4.20-4.31 (m, 3H), 4.08-4.03 (m, 2H), 3.80-3.76 (m, 1H), 3.10 (s, 1H), 2.89 (s, 3H).
[20]$^1$H NMR (400 MHz, CDCl$_3$) δ 7.56 (dd, J = 2.2, 6.6 Hz, 1H), 7.28 (ddd, J = 8.6, 4.6, 2.4 Hz, 1H), 7.11 (t, J = 8.4 Hz, 1H), 6.13 (t, J = 2.9 Hz, 1H), 4.32-4.30 (m, 2H), 4.24 (t, J = 10.1 Hz, 1H), 4.19 (dd, J = 1.3, 11.4 Hz, 1H), 4.10-4.06 (m, 1H), 3.68 (ddd, J = 11.6, 2.9, 1.3 Hz, 1H), 2.95 (s, 4H).
[21]$^1$H NMR (400 MHz, CDCl$_3$) δ 7.39 (t, J = 7.7 Hz, 1H), 6.89 (dd, J = 8.1, 10.3 Hz, 1H), 6.02 (t, J = 2.6 Hz, 1H), 4.20-4.31 (m, 3H), 4.08-4.02 (m, 2H), 3.81-3.75 (m, 1H), 2.92 (s, 4H).
[22]$^1$H NMR (400 MHz, CDCl$_3$) δ 7.42-7.44 (m, 1H), 7.36-3.39 (m, 1H), 7.18-7.22 (m, 2H), 6.08-6.11 (m, 1H), 4.00-4.03 (m, 2H), 3.08-3.13 (brd, 1H), 2.85 (s, 3H), 2.18-2.22 (m, 2H), 1.94-2.01 (m, 1H), 1.78-1.88 (m, 1H), 1.63-1.71 (m, 2H).
[23]DMAP and triethylamine is utilized in this reaction.
[24]$^1$H NMR (400 MHz, CDCl$_3$) δ 7.53 (s, 1H), 7.37-7.29 (m, 2H), 7.19 (t, J = 7.9 Hz, 1H), 6.22 (s, 1H), 4.26 (dd, J = 4.0, 10.1 Hz, 1H), 4.01 (dd, J = 7.9, 9.7 Hz, 1H), 3.54-3.52 (m, 1H), 2.86 (s, 3H), 2.59-2.51 (m, 2H), 2.28-2.19 (m, 1H), 2.04 (ddd, J = 17.0, 7.8, 3.8 Hz, 1H).

Preparation 22

(4-(3-Bromophenyl)-3,6-dihydro-2H-pyran-3-yl) methyl carbamimidothioate methanesulfonate

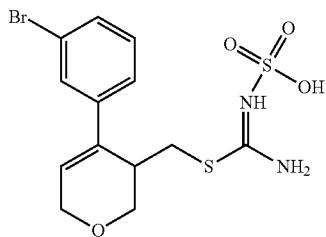

A mixture of (4-(3-bromophenyl)-3,6-dihydro-2H-pyran-3-yl)methyl methanesulfonate (4.82 g, 11.7 mmol) and thiourea (1.78 g, 23.3 mmol) in isopropyl alcohol (100 mL) is heated to reflux for 24 h. The reaction is cooled and the solvent is removed under reduced vacuum to give a residue that is combined with acetonitrile (30 mL) and hexanes (10 mL). A solid crystallizes and the slurry is cooled to 0° C. The slurry is filtered using 3:1 ACN:hexanes as a rinse (25 mL) to give the title compound as the mesylate salt (3.45 g, 70%). ES/MS m/e ($^{79}$Br/$^{81}$Br) 327, 329 (M+1).

The following compounds in Table 16 are prepared essentially as described in the preparation of (4-(3-bromophenyl)-3,6-dihydro-2H-pyran-3-yl)methyl carbamimidothioate methanesulfonate.

TABLE 16

| Prep | Chemical name | ES/MS (m/e) (M + 1) |
|---|---|---|
| 22a | (4-(5-Bromo-2-fluorophenyl)-3,6-dihydro-2H-pyran-3-yl)methyl carbamimidothioate methanesulfonate | ($^{79}$Br/$^{81}$Br) 345/347 |
| 22b | (4-(3-Bromo-4-fluorophenyl)-3,6-dihydro-2H-pyran-3-yl)methyl carbamimidothioate methanesulfonate | ($^{79}$Br/$^{81}$Br) 345/347 |
| 22c | (4-(5-Bromo-2,4-difluorophenyl)-3,6-dihydro-2H-pyran-3-yl)methyl carbamimidothioate methanesulfonate | ($^{79}$Br/$^{81}$Br) 363/365 |
| 22d | (2-(3-Bromophenyl)cyclohex-2-enyl)methyl carbamimidothioate methanesulfonate | ($^{79}$Br/$^{81}$Br) 325/327 |
| 22e | (2-(4-fluoro-3-methoxyphenyl)cyclopent-2-enyl)methyl carbamimidothioate methanesulfonate | 281 |
| 22f | (2-(3-bromophenyl)cyclopent-2-enyl)methyl carbamimidothioate methanesulfonate | ($^{79}$Br/$^{81}$Br) 311/313 |

Preparation 23

Racemic (4aSR,8aSR)-8a-(3-Bromophenyl)-4,4a,5,7,8,8a-hexahydropyrano[4,3-d][1,3]thiazin-2-amine

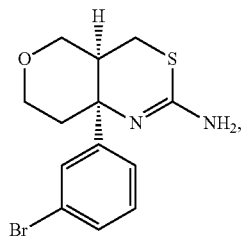

A mixture of (4-(3-bromophenyl)-3,6-dihydro-2H-pyran-3-yl)methyl carbamimidothioate methanesulfonate (3.41 g, 8.05 mmol) in methanesulfonic acid (35 mL) is heated at 50° C. for 5 h. The reaction is cooled and added to ice water. The mixture is diluted with EtOAc and the pH adjusted with 5 N NaOH to basic. The basic aqueous layer is extracted three times with ethyl acetate and the organic layer is dried over $Na_2SO_4$. The solvent is removed under reduced pressure. The resulting residue is triturated with $CH_2Cl_2$ to give the title racemic compound. Additional racemic product is obtained by purification of the filtrate by silica gel chromatography eluting with a linear gradient of 1% to 10% 7 M $NH_3$/MeOH in $CH_2Cl_2$ (1.99 g, 76%). ES/MS m/e ($^{79}Br/^{81}Br$) 327, 329 (M+1).

The following compounds in Table 17 are prepared essentially as described in the preparation of (4aSR,8aSR)-8a-(3-bromophenyl)-4,4a,5,7,8,8a-hexahydropyrano[4,3-d][1,3]thiazin-2-amine

Preparation 24

Racemic tert-Butyl (4aSR,8aSR)-8a-(3-bromophenyl)-4,4a,5,7,8,8a-hexahydropyrano[4,3-d][1,3]thiazin-2-ylcarbamate

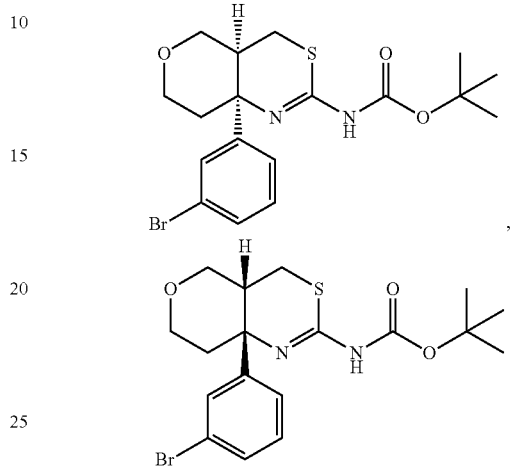

A mixture of racemic (4aSR,8aSR)-8a-(3-bromophenyl)-4,4a,5,7,8,8a-hexahydropyrano[4,3-d][1,3]thiazin-2-amine (2.08 g, 6.36 mmol) and di-t-butyldicarbonate (2.77 g, 12.7 mmol) in 1,4-dioxane (60 mL) and saturated aqueous $NaHCO_3$ (60 mL) is stirred at room temperature for 8 h. The mixture is diluted water and extracted three times with EtOAc. The combined organic layers are dried over $Na_2SO_4$ and the solvent is removed under reduced pressure to afford material that is purified by silica gel chromatography eluting with a linear gradient of 5% to 100% EtOAc in hexanes to give the title compound (2.81 g, 100%). ES/MS m/e ($^{79}Br/^{81}Br$) 427, 429 (M+1).

The following compounds in Table 18 are prepared essentially as described in the preparation of racemic tert-butyl (4aSR,8aSR)-8a-(3-bromophenyl)-4,4a,5,7,8,8a-hexahydropyrano[4,3-d][1,3]thiazin-2-ylcarbamate.

TABLE 17

| Prep | Chemical name | ES/MS (m/e) (M + 1) |
|---|---|---|
| 23a | Racemic (4aSR,8aSR)-8a-(5-Bromo-2-fluorophenyl)-4,4a,5,7,8,8a-hexahydropyrano[4,3-d][1,3]thiazin-2-amine[25] | ($^{79}Br/^{81}Br$) 345, 347 |
| 23b | Racemic (4aSR,8aSR)-8a-(3-Bromo-4-fluorophenyl)-4,4a,5,7,8,8a-hexahydropyrano[4,3-d][1,3]thiazin-2-amine[26] | ($^{79}Br/^{81}Br$) 345/347 |
| 23c | Racemic (4aSR,8aSR)-8a-(5-Bromo-2,4-difluorophenyl)-4,4a,5,7,8,8a-hexahydropyrano[4,3-d][1,3]thiazin-2-amine[25] | ($^{79}Br/^{81}Br$) 363/365 |
| 23d | Racemic (4aRS,8aSR)-8a-(3-Bromophenyl)-4a,5,6,7,8,8a-hexahydro-4H-benzo[d][1,3]thiazin-2-amine | ($^{79}Br/^{81}Br$) 325/327 |
| 23e | Racemic (4aRS,7aSR)-7a-(4-Fluoro-3-methoxyphenyl)-4,4a,5,6,7,7a-hexahydrocyclopenta[d][1,3]thiazin-2-amine[27] | 281 |
| 23f | Racemic (4aRS,7aSR)-7a-(3-Bromophenyl)-4,4a,5,6,7,7a-hexahydrocyclopenta[d][1,3]thiazin-2-amine methanesulfonate[28] | ($^{79}Br/^{81}Br$) 311/313 |

[25] The reaction is heated at 90° C. overnight.
[26] The reaction is heated at 50° C. for 5 h.
[27] The reaction is stirred at room temperature for 3 h.
[28] The reaction is stirred at room temperature for 17 h. Product isolated as the salt.

TABLE 18

| Prep | Chemical name | ES/MS (m/e) (M + 1) |
|---|---|---|
| 24a | Racemic tert-Butyl (4aSR,8aSR)-8a-(5-bromo-2-fluorophenyl)-4,4a,5,7,8,8a-hexahydropyrano[4,3-d][1,3]thiazin-2-ylcarbamate | ($^{79}$Br/$^{81}$Br) 445/447 |
| 24b | Racemic tert-Butyl (4aSR,8aSR)-8a-(3-bromo-4-fluorophenyl)-4,4a,5,7,8,8a-hexahydropyrano[4,3-d][1,3]thiazin-2-ylcarbamate | ($^{79}$Br/$^{81}$Br) 445/447 |
| 24c | Racemic tert-Butyl (4aSR,8aSR)-8a-(5-bromo-2,4-difluorophenyl)-4,4a,5,7,8,8a-hexahydropyrano[4,3-d][1,3]thiazin-2-ylcarbamate | ($^{79}$Br/$^{81}$Br) 463/465 |
| 24d | Racemic tert-Butyl (4aRS,8aSR)-8a-(3-bromophenyl)-4a,5,6,7,8,8a-hexahydro-4H-benzo[d][1,3]thiazin-2-ylcarbamate | ($^{79}$Br/$^{81}$Br) 425/427 |
| 24e | Racemic tert-Butyl (4aRS,7aSR)-7a-(4-fluoro-3-methoxyphenyl)-4,4a,5,6,7,7a-hexahydrocyclopenta[d][1,3]thiazin-2-ylcarbamate | 381 |
| 24f | Racemic tert-Butyl (4aRS,7aSR)-7a-(3-bromophenyl)-4,4a,5,6,7,7a-hexahydrocyclopenta[d][1,3]thiazin-2-ylcarbamate | ($^{79}$Br/$^{81}$Br) 411/413 |
| 24g | Racemic tert-Butyl (4aSR,7aSR)-7a-(5-bromo-2-fluorophenyl)-4a,5,7,7a-tetrahydro-4H-furo[3,4-d][1,3]thiazin-2-ylcarbamate | ($^{79}$Br/$^{81}$Br) 431/433 |

Preparation 25 tert-Butyl (8aS)-8a-(3-bromophenyl)-4,4a,5,7,8,8a-hexahydropyrano[4,3-d][1,3]thiazin-2-ylcarbamate

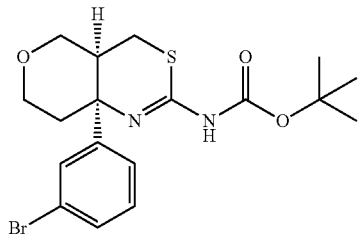

Racemic tert-butyl (4aSR,8aSR)-8a-(3-bromophenyl)-4,4a,5,7,8,8a-hexahydropyrano[4,3-d][1,3]thiazin-2-ylcarbamate (2.80 g, 6.55 mmol) is purified by chiral HPLC: Column: Chiralcel OJ 8×35 cm; eluent: 75:25 (methanol:acetonitrile); flow: 400 mL/min at UV 260 nm. The second eluting isomer is isolated to provide the enantiomerically enriched title compound (1.31 g, 47%). ES/MS m/e ($^{79}$Br/$^{81}$Br) 427, 429 (M+1).

The following compounds in Table 19 are prepared essentially as described in the preparation of tert-butyl (8aS)-8a-(3-bromophenyl)-4,4a,5,7,8,8a-hexahydropyrano[4,3-d][1,3]thiazin-2-ylcarbamate.

Preparation 26 tert-Butyl (8aS)-8a-(3-azidophenyl)-4,4a,5,7,8,8a-hexahydropyrano[4,3-d][1,3]thiazin-2-ylcarbamate

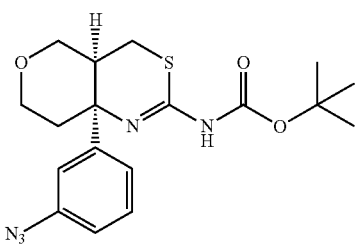

A 0.33 M solution of copper sulfate is prepared by dissolving copper (II) sulfate pentahydrate (1.0 g, 2.0 mmol) in water (12 mL). A 0.66 M solution of L-ascorbic acid is prepared by dissolving L-ascorbic acid sodium salt (1.58 g, 4.0 mmol) in water (12 mL). To a solution of tert-butyl (8aS)-8a-(3-bromophenyl)-4,4a,5,7,8,8a-hexahydropyrano[4,3-d][1,3]thiazin-2-ylcarbamate (0.500 g, 1.20 mmol) in ethanol (3.6 mL) is added sodium azide (0.228 g, 3.50 mmol), 1,2-cyclohexanediamine, N,N'-dimethyl-, trans (+/−) (0.0549 g, 0.386 mmol), 0.66 M aqueous L-ascorbic acid sodium salt (0.772 mL, 0.509 mmol), and water (0.71 mL) and the mixture is purged with nitrogen. A 0.33 M aqueous solution of copper (II) sulfate pentahydrate (0.773 mL, 0.255 mmol) is added

TABLE 19

| Prep. No. | Chemical name | ES/MS (m/e) (M + 1) |
|---|---|---|
| 25a | tert-Butyl (8aS)-8a-(5-bromo-2-fluorophenyl)-4,4a,5,7,8,8a-hexahydropyrano[4,3-d][1,3]thiazin-2-ylcarbamate | ($^{79}$Br/$^{81}$Br) 445/447 |
| 25b | tert-Butyl (8aS)-8a-(3-bromo-4-fluorophenyl)-4,4a,5,7,8,8a-hexahydropyrano[4,3-d][1,3]thiazin-2-ylcarbamate | ($^{79}$Br/$^{81}$Br) 445/447 |
| 25c | tert-Butyl (8aS)-8a-(5-bromo-2,4-difluorophenyl)-4,4a,5,7,8,8a-hexahydropyrano[4,3-d][1,3]thiazin-2-ylcarbamate | ($^{79}$Br/$^{81}$Br) 463/465 |
| 25d | tert-Butyl (8aS)-8a-(3-bromophenyl)-4a,5,6,7,8,8a-hexahydro-4H-benzo[d][1,3]thiazin-2-ylcarbamate | ($^{79}$Br/$^{81}$Br) 425/427 |
| 25e | tert-Butyl (7aS)-7a-(4-fluoro-3-methoxyphenyl)-4,4a,5,6,7,7a-hexahydrocyclopenta[d][1,3]thiazin-2-ylcarbamate | 381 |
| 25f | tert-Butyl (7aS)-7a-(3-bromophenyl)-4,4a,5,6,7,7a-hexahydrocyclopenta[d][1,3]thiazin-2-ylcarbamate | ($^{79}$Br/$^{81}$Br) 411/413 | and the reaction is heated to 80° C. for 12 min. The reaction is poured into cold water to afford a blue mixture that is extracted three times with EtOAc. The organic layer is dried over Na$_2$SO$_4$ to afford crude material which is purified by silica gel chromatography eluting with a linear gradient of 5% to 100% EtOAc in hexanes to give the title compound (0.400 g, 88%). ES/MS m/e: 390 (M+1).

The following compounds in Table 20 are prepared essentially as described in the preparation of tert-butyl (8aS)-8a-(3-azidophenyl)-4,4a,5,7,8,8a-hexahydropyrano[4,3-d][1,3]thiazin-2-ylcarbamate.

TABLE 20

| Prep | Chemical name | ES/MS (m/e) (M + 1) |
|---|---|---|
| 26a | tert-Butyl (8aS)-8a-(5-azido-2-fluorophenyl)-4,4a,5,7,8,8a-hexahydropyrano[4,3-d][1,3]thiazin-2-ylcarbamate | 408 |
| 26b | tert-Butyl (8aS)-8a-(3-azido-4-fluorophenyl)-4,4a,5,7,8,8a-hexahydropyrano[4,3-d][1,3]thiazin-2-ylcarbamate | 408 |
| 26c | tert-Butyl (8aS)-8a-(3-azidophenyl)-4a,5,6,7,8,8a-hexahydro-4H-benzo[d][1,3]thiazin-2-ylcarbamate | 388 |
| 26d | tert-Butyl (7aS)-7a-(3-azidophenyl)-4,4a,5,6,7,7a-hexahydrocyclopenta[d][1,3]thiazin-2-ylcarbamate | 374 |
| 26e | Racemic tert-Butyl (4aSR,7aSR)-7a-(5-azido-2-fluorophenyl)-4a,5,7,7a-tetrahydro-4H-furo[3,4-d][1,3]thiazin-2-ylcarbamate | 394 |

Preparation 27 tert-Butyl (8aS)-8a-(3-aminophenyl)-4,4a,5,7,8,8a-hexahydropyrano[4,3-d][1,3]thiazin-2-ylcarbamate

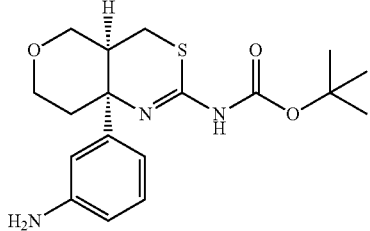

A mixture of tert-butyl (8aS)-8a-(3-azidophenyl)-4,4a,5,7,8,8a-hexahydropyrano[4,3-d][1,3]thiazin-2-ylcarbamate (0.398 g, 1.02 mmol) and palladium on carbon −10% by weight (0.200 g) in ethanol (25 mL) is purged with nitrogen then hydrogen. The reaction is stirred at room temperature under hydrogen (30 psi) for 2 h. Na$_2$SO$_4$ is added to the reaction mixture and it is filtered through diatomaceous earth, using methanol to rinse the filter cake. The solvent is removed under reduced pressure to give the title compound (0.361 g, 97%). ES/MS m/e: 364 (M+1).

The following compounds in Table 21 are prepared essentially as described in the preparation of tert-butyl (8aS)-8a-(3-aminophenyl)-4,4a,5,7,8,8a-hexahydropyrano[4,3-d][1,3]thiazin-2-ylcarbamate.

TABLE 21

| Prep | Chemical name | ES/MS (m/e) (M + 1) |
|---|---|---|
| 27a | tert-Butyl (8aS)-8a-(5-amino-2-fluorophenyl)-4,4a,5,7,8,8a-hexahydropyrano[4,3-d][1,3]thiazin-2-ylcarbamate | 382 |
| 27b | tert-Butyl (8aS)-8a-(3-amino-4-fluorophenyl)-4,4a,5,7,8,8a-hexahydropyrano[4,3-d][1,3]thiazin-2-ylcarbamate | 382 |
| 27c | tert-Butyl (8aS)-8a-(3-aminophenyl)-4a,5,6,7,8,8a-hexahydro-4H-benzo[d][1,3]thiazin-2-ylcarbamate | 362 |
| 27d | tert-Butyl (7aS)-7a-(3-aminophenyl)-4,4a,5,6,7,7a-hexahydrocyclopenta[d][1,3]thiazin-2-ylcarbamate | 348 |
| 27e | Racemic tert-Butyl (4aSR,7aSR)-7a-(5-amino-2-fluorophenyl)-4a,5,7,7a-tetrahydro-4H-furo[3,4-d][1,3]thiazin-2-ylcarbamate | 368 |

Preparation 28 tert-Butyl (8aS)-8a-(3-(5-chloropicolinamido)phenyl)-4,4a,5,7,8,8a-hexahydropyrano[4,3-d][1,3]thiazin-2-ylcarbamate

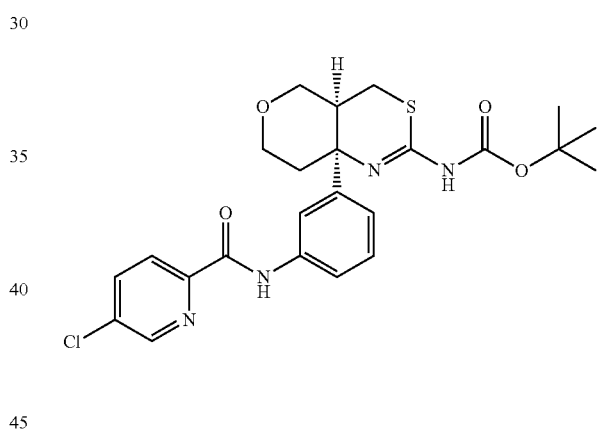

To a mixture of tert-butyl (8aS)-8a-(3-aminophenyl)-4,4a,5,7,8,8a-hexahydropyrano[4,3-d][1,3]thiazin-2-ylcarbamate (0.15 g, 0.413 mmol), 5-chloropyridine-2-carboxylic acid (0.078 g, 0.495 mmol) and 1-hydroxybenzotriazole (0.073 g, 0.536 mmol) in CH$_2$Cl$_2$ (2.75 mL) and DMF (0.3 mL) is added 1-(3-dimethylaminopropyl)-3-ethylcarbodiimide hydrochloride (0.103 g, 0.536 mmol). The reaction is stirred overnight at room temperature. The reaction mixture is diluted with water, 5 N NaOH (0.5 mL) and extracted three times with CH$_2$Cl$_2$. The combined organic layer is dried over Na$_2$SO$_4$ and the crude product is purified by silica gel chromatography eluting with a linear gradient of 5% to 100% EtOAc in hexanes to give the title compound (0.176 g, 85%). ES/MS m/e: ($^{35}$Cl/$^{37}$Cl) 503, 505 (M+1).

The following compounds in Table 22 are prepared essentially as described in the preparation of tert-butyl (8aS)-8a-(3-(5-chloropicolinamido)phenyl)-4,4a,5,7,8,8a-hexahydropyrano[4,3-d][1,3]thiazin-2-ylcarbamate.

TABLE 22

| Prep | Chemical name | ES/MS (m/e) (M + 1) |
|---|---|---|
| 28a | tert-Butyl (8aS)-8a-(5-(5-chloropicolinamido)-2-fluorophenyl)-4,4a,5,7,8,8a-hexahydropyrano[4,3-d][1,3]thiazin-2-ylcarbamate | ($^{35}$Cl/$^{37}$Cl) 521/523 |
| 28b | tert-Butyl (8aS)-8a-(2-fluoro-5-(5-fluoropicolinamido)phenyl)-4,4a,5,7,8,8a-hexahydropyrano[4,3-d][1,3]thiazin-2-ylcarbamate | 505 |
| 28c | tert-Butyl (8aS)-8a-(2-fluoro-5-(thiazole-2-carboxamido)phenyl)-4,4a,5,7,8,8a-hexahydropyrano[4,3-d][1,3]thiazin-2-ylcarbamate | 493 |
| 28d | tert-Butyl (8aS)-8a-(2-fluoro-5-(picolinamido)phenyl)-4,4a,5,7,8,8a-hexahydropyrano[4,3-d][1,3]thiazin-2-ylcarbamate | 487 |
| 28e | tert-Butyl (8aS)-8a-(5-(5-chloropyrimidine-2-carboxamido)-2-fluorophenyl)-4,4a,5,7,8,8a-hexahydropyrano[4,3-d][1,3]thiazin-2-ylcarbamate | ($^{35}$Cl/$^{37}$Cl) 522, 524 |
| 28f | tert-Butyl (8aS)-8a-(2-fluoro-5-(5-fluoropyrimidine-2-carboxamido)phenyl)-4,4a,5,7,8,8a-hexahydropyrano[4,3-d][1,3]thiazin-2-ylcarbamate | 506 |
| 28g | tert-Butyl (8aS)-8a-(3-(5-chloropicolinamido)-4-fluorophenyl)-4,4a,5,7,8,8a-hexahydropyrano[4,3-d][1,3]thiazin-2-ylcarbamate | ($^{35}$Cl/$^{37}$Cl) 521, 523 |
| 28h | tert-Butyl (8aS)-8a-(3-(5-chloropicolinamido)phenyl)-4a,5,6,7,8,8a-hexahydro-4H-benzo[d][1,3]thiazin-2-ylcarbamate | ($^{35}$Cl/$^{37}$Cl) 501, 503 |
| 28i | tert-Butyl (7aS)-7a-(3-(isonicotinamido)phenyl)-4,4a,5,6,7,7a-hexahydrocyclopenta[d][1,3]thiazin-2-ylcarbamate | 453 |
| 28j | tert-Butyl (7aS)-7a-(3-(picolinamido)phenyl)-4,4a,5,6,7,7a-hexahydrocyclopenta[d][1,3]thiazin-2-ylcarbamate | 453 |
| 28k | tert-Butyl (7aS)-7a-(3-(pyrazine-2-carboxamido)phenyl)-4,4a,5,6,7,7a-hexahydrocyclopenta[d][1,3]thiazin-2-ylcarbamate | 454 |
| 28m | tert-Butyl (7aS)-7a-(3-(pyrimidine-2-carboxamido)phenyl)-4,4a,5,6,7,7a-hexahydrocyclopenta[d][1,3]thiazin-2-ylcarbamate | 454 |
| 28n | tert-Butyl (7aS)-7a-(3-benzamidophenyl)-4,4a,5,6,7,7a-hexahydrocyclopenta[d][1,3]thiazin-2-ylcarbamate | 452 |
| 28p | tert-Butyl (7aS)-7a-(3-(pyrimidine-4-carboxamido)phenyl)-4,4a,5,6,7,7a-hexahydrocyclopenta[d][1,3]thiazin-2-ylcarbamate | 454 |
| 28q | Racemic tert-Butyl (7aSR)-7a-(2-fluoro-5-(5-fluoropicolinamido)phenyl)-4a,5,7,7a-tetrahydro-4H-furo[3,4-d][1,3]thiazin-2-ylcarbamate | 491 |
| 28r | Racemic tert-Butyl (7aSR)-7a-(5-(5-chloropicolinamido)-2-fluorophenyl)-4a,5,7,7a-tetrahydro-4H-furo[3,4-d][1,3]thiazin-2-ylcarbamate | 507 |
| 28s | Racemic tert-Butyl (7aSR)-7a-(2-fluoro-5-(5-fluoropyrimidine-2-carboxamido)phenyl)-4a,5,7,7a-tetrahydro-4H-furo[3,4-d][1,3]thiazin-2-ylcarbamate | 492 |

Preparation 29 tert-Butyl (4aS,7aS)-7a-(2-fluoro-5-(5-fluoropicolinamido)phenyl)-4a,5,7,7a-tetrahydro-4H-furo[3,4-d][1,3]thiazin-2-ylcarbamate

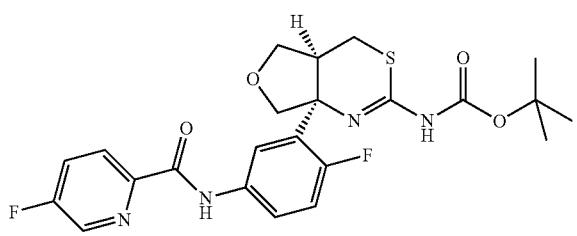

Racemic tert-butyl (4aSR,7aSR)-7a-(2-fluoro-5-(5-fluoropicolinamido)phenyl)-4a,5,7,7a-tetrahydro-4H-furo[3,4-d][1,3]thiazin-2-ylcarbamate (0.226 g, 0.460 mmol) is purified by chiral HPLC: 2.1×25 cm Chiralcel OD-H, 5 micron column, 30% methanol/CO$_2$, flow rate: 70 mL/min, UV: 230 nm. The second eluting isomer is isolated to provide the enantiomerically enriched title compound (0.092 g, 41%). ES/MS (m/e): 491 (M+1).

The following compounds in Table 23 are prepared essentially by the method of tert-butyl (4aS,7aS)-7a-(2-fluoro-5-(5-fluoropicolinamido)phenyl)-4a,5,7,7a-tetrahydro-4H-furo[3,4-d][1,3]thiazin-2-ylcarbamate.

TABLE 23

| Prep | Chemical name | ES/MS (m/e) (M + 1) |
|---|---|---|
| 29a | tert-Butyl (4aS,7aS)-7a-(5-(5-chloropicolinamido)-2-fluorophenyl)-4a,5,7,7a-tetrahydro-4H-furo[3,4-d][1,3]thiazin-2-ylcarbamate | 507 |
| 29b | tert-Butyl (4aS,7aS)-7a-(2-fluoro-5-(5-fluoropyrimidine-2-carboxamido)phenyl)-4a,5,7,7a-tetrahydro-4H-furo[3,4-d][1,3]thiazin-2-ylcarbamate | 492 |

Preparation 30 tert-Butyl (8aS)-8a-(2,4-difluoro-5-(pyrimidin-5-yl)phenyl)-4,4a,5,7,8,8a-hexahydropyrano[4,3-d][1,3]thiazin-2-ylcarbamate

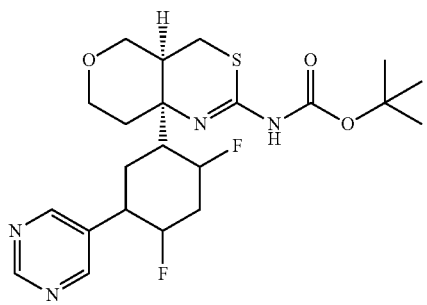

A mixture of tert-butyl 8a-(5-bromo-2,4-difluorophenyl)-4,4a,5,7,8,8a-hexahydropyrano[4,3-d][1,3]thiazin-2-ylcarbamate (0.300 g, 0.647 mmol) in 1,2-dimethoxyethane (10 mL), ethanol (4 mL) and water (5 mL) is purged with nitrogen and heated to 97° C. Pyrimidine-5-boronic acid (0.655 g, 5.18 mmol), cesium carbonate (1.90 g, 5.83 mmol) and bis(triphenylphosphine)palladium(II) chloride (0.091 g, 0.129 mmol) is added in a single portion and the reaction is heated at 97° C. for 20 minutes. The reaction is cooled, diluted with water, and extracted with EtOAc. The organic layer is dried over $Na_2SO_4$ and the crude product is purified by silica gel chromatography eluting with a linear gradient of 5% to 100% EtOAc in hexanes to give the title compound (0.258 g, 86%). ES/MS (m/e): 463 (M+1).

The following compound in Table 24 are prepared essentially as described in the preparation of tert-butyl (8aS)-8a-(2,4-difluoro-5-(pyrimidin-5-yl)phenyl)-4,4a,5,7,8,8a-hexahydropyrano[4,3-d][1,3]thiazin-2-ylcarbamate.

TABLE 24

| Prep. No. | Chemical name | ES/MS (m/e) |
|---|---|---|
| 30a | Racemic tert-Butyl (4aSR,7aSR)-7a-(4-fluoro-3-(pyrimidin-5-yl)phenyl)-4a,5,7,7a-tetrahydro-4H-furo[3,4-d][1,3]thiazin-2-ylcarbamate; racemic tert-Butyl (4aSR,7aSR)-7a-(2-fluoro-5-(pyrimidin-5-yl)phenyl)-4a,5,7,7a-tetrahydro-4H-furo[3,4-d][1,3]thiazin-2-ylcarbamate[29] | 453 (M + 23) |

[29]Compounds are recovered as a mixture.

Preparation 31

Racemic (4aSR,7aSR)-7a-(4-Fluoro-3-(pyrimidin-5-yl)phenyl)-4a,5,7,7a-tetrahydro-4H-furo[3,4-d][1,3]thiazin-2-amine and Racemic (4aSR,7aSR)-7a-(2-Fluoro-5-(pyrimidin-5-yl)phenyl)-4a,5,7,7a-tetrahydro-4H-furo[3,4-d][1,3]thiazin-2-amine

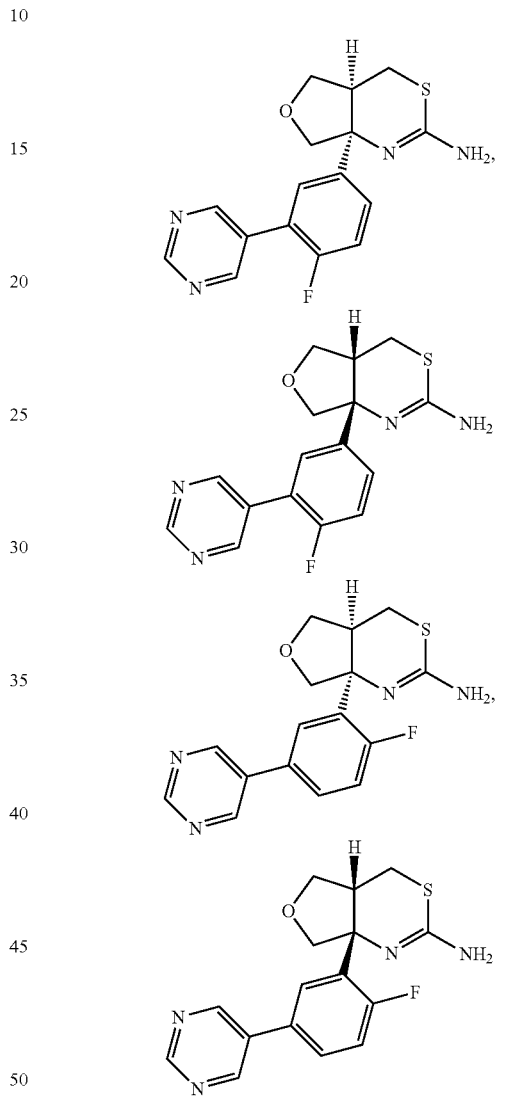

A solution of 4 M Hydrogen chloride in dioxane (19.2 mL) is added to a mixture of racemic tert-butyl (4aSR,7aSR)-7a-(4-fluoro-3-(pyrimidin-5-yl)phenyl)-4a,5,7,7a-tetrahydro-4H-furo[3,4-d][1,3]thiazin-2-ylcarbamate and racemic tert-butyl (4aSR,7aSR)-7a-(2-fluoro-5-(pyrimidin-5-yl)phenyl)-4a,5,7,7a-tetrahydro-4H-furo[3,4-d][1,3]thiazin-2-ylcarbamate (1.80 g, 0.962 mmol) and the reaction is stirred at room temperature for 3 h. The mixture is diluted with aqueous 1 N HCl and is extracted with dichloromethane. Aqueous 5 N sodium hydroxide is added to the aqueous layer to make it basic and it is extracted twice with 10% isopropyl alcohol in dichloromethane. The solvent is removed under reduced pressure to give a residue that is purified on silica gel using radial chromatography eluting with 3% to 10% 2M ammonia in methanol:dichloromethane. The material is purified again using radial chromatography eluting with 10% isopropylamine:30% ethyl acetate:60% hexane to give the title compounds as a racemic two component mixture (0.231 g, 73%). ES/MS m/e: 331 (M+1).

Preparation 32

(4aS,7aS)-7a-(4-Fluoro-3-(pyrimidin-5-yl)phenyl)-4a,5,7,7a-tetrahydro-4H-furo[3,4-d][1,3]thiazin-2-amine and (4aS,7aS)-7a-(2-Fluoro-5-(pyrimidin-5-yl)phenyl)-4a,5,7,7a-tetrahydro-4H-furo[3,4-d][1,3]thiazin-2-amine

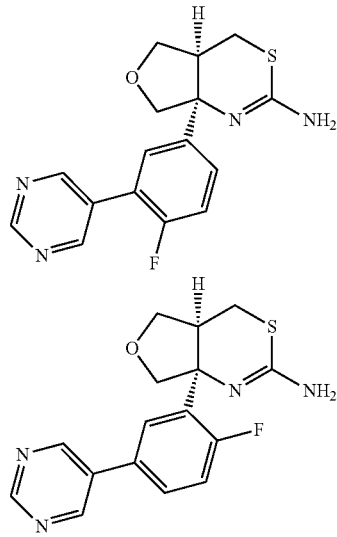

The mixture of racemic (4aSR,7aSR)-7a-(4-fluoro-3-(pyrimidin-5-yl)phenyl)-4a,5,7,7a-tetrahydro-4H-furo[3,4-d][1,3]thiazin-2-amine and racemic (4aSR,7aSR)-7a-(2-fluoro-5-(pyrimidin-5-yl)phenyl)-4a,5,7,7a-tetrahydro-4H-furo[3,4-d][1,3]thiazin-2-amine (0.231 g, 0.697 mmol) are separated using a Chiralpak AD-H 3×25 cm column eluting with 3/2 EtOH:acetonitrile with 0.2% dimethylethylamine at a flow rate of 30 mL/min., 225 nM to give (4aS,7aS)-7a-(4-fluoro-3-(pyrimidin-5-yl)phenyl)-4a,5,7,7a-tetrahydro-4H-furo[3,4-d][1,3]thiazin-2-amine ($T_R$=3.12) (0.032 g, 14%): ES/MS m/e: 331 (M+1) and (4aS,7aS)-7a-(2-fluoro-5-(pyrimidin-5-yl)phenyl)-4a,5,7,7a-tetrahydro-4H-furo[3,4-d][1,3]thiazin-2-amine ($T_R$=4.479) (0.058 g, 25%). ES/MS m/e: 331 (M+1).

Preparation 33

(7aS)-7a-(4-Fluoro-3-methoxyphenyl)-4,4a,5,6,7,7a-hexahydrocyclopenta[d][1,3]thiazin-2-amine

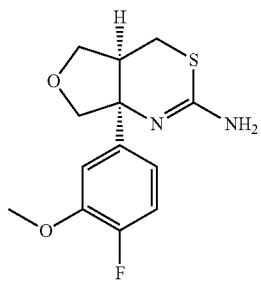

To a solution tert-butyl 7a-(4-fluoro-3-methoxyphenyl)-4,4a,5,6,7,7a-hexahydrocyclopenta[d][1,3]thiazin-2-ylcarbamate (1.04 g, 2.73 mmol) in CH$_2$Cl$_2$ (20 mL) is added TFA (5 mL) and the reaction is stirred at room temperature for 16 hr. The solvent is removed under reduced pressure to give a residue that is diluted with water and 5N NaOH. The aqueous layer is extracted four times with EtOAc. The organic layer is dried over Na$_2$SO$_4$ and the solvent is removed under reduced pressure. The crude product is purified with a 10 g SCX column using 4:1 CH$_2$Cl$_2$:MeOH and then 2:1 CH$_2$Cl$_2$: 7 N NH$_3$ in MeOH to elute the product and give the title compound (0.756 g, 99%). ES/MS m/e: 281 (M+1).

Preparation 34

5-((7aS)-2-Amino-4,4a,5,6,7,7a-hexahydrocyclopenta[d][1,3]thiazin-7a-yl)-2-fluorophenol

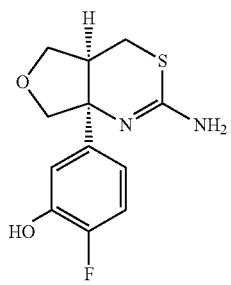

To a −78° C. solution of (7aS)-7a-(4-fluoro-3-methoxyphenyl)-4,4a,5,6,7,7a-hexahydrocyclopenta[d][1,3]thiazin-2-amine (0.717 g, 2.56 mmol) in CH$_2$Cl$_2$ (15 mL) is added boron tribromide 11.20 g, 7.67 mmol). The reaction is warmed to 0° C. and is stirred for 2 hr. The reaction is diluted with water and the pH is adjusted to 7. The aqueous is extracted three times with EtOAc (some MeOH is added to help dissolve some solids during the extraction). The organic layer is dried over Na$_2$SO$_4$ and the solvent is removed under reduced pressure. The crude product is purified with a 10 g SCX column using 4:1 CH$_2$Cl$_2$:MeOH and then 2:1 CH$_2$Cl$_2$:7 N NH$_3$ in MeOH to elute the product and give the title compound (0.56 g, 82%). ES/MS m/e: 267 (M+1).

Preparation 35 tert-Butyl (7aS)-7a-(4-fluoro-3-hydroxyphenyl)-4,4a,5,6,7,7a-hexahydrocyclopenta[d][1,3]thiazin-2-ylcarbamate

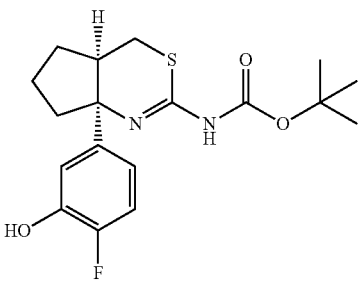

To a mixture of 5-((4aR,7aS)-2-amino-4,4a,5,6,7,7a-hexahydrocyclopenta[d][1,3]thiazin-7a-yl)-2-fluorophenol (0.524 g, 1.97 mmol) in 1,4-dioxane (20 mL) and saturated aqueous NaHCO$_3$ (20 mL) is added a solution of di-tert-butyldicarbonate (0.451 g, 2.07 mmol) in 1,4-dioxane (2 mL). The mixture is stirred at room temperature for 16 h. The mixture is diluted water and extracted three times with EtOAc. The organic layer is dried over Na$_2$SO$_4$ and the crude product is purified by silica gel chromatography eluting with a linear gradient of 5% to 100% EtOAc in hexanes to give the title compound (0.436 g, 61%). ES/MS m/e: 367 (M+1).

Preparation 36

5-((7aS)-2-(tert-Butoxycarbonylamino)-4,4a,5,6,7,7a-hexahydrocyclopenta[d][1,3]thiazin-7a-yl)-2-fluorophenyl trifluoromethanesulfonate

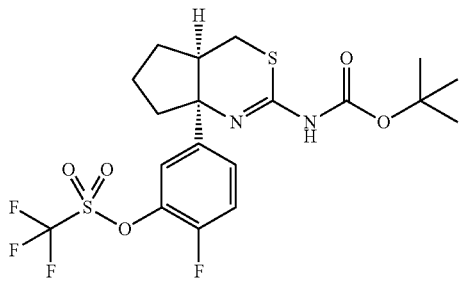

To a 0° C. mixture of tert-butyl (4aR,7aS)-7a-(4-fluoro-3-hydroxyphenyl)-4,4a,5,6,7,7a-hexahydrocyclopenta[d][1,3]thiazin-2-ylcarbamate (0.428 g, 1.17 mmol) and pyridine (0.148 g, 1.87 mmol) in dichloromethane (25 mL) is added trifluoromethanesulfonic anhydride (0.395 g, 1.40 mmol). The reaction is stirred at 0° C. for 45 min. The reaction is diluted with water and 1 N HCl (4 mL) and is extracted three times with CH$_2$Cl$_2$. The organic layer is dried over Na$_2$SO$_4$ and the solvent is removed under reduced pressure to give the title compound (0.633 g, 100%). ES/MS m/e: 499 (M+1).

Preparation 37

5-Bromo-2,4-difluorobenzaldehyde

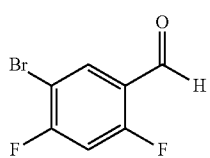

A 1.6 M solution of butyl lithium in hexane (114 mL, 182 mmol) is added to a −78° C. solution of 1,5-dibromo-2,4-difluorobenzene (41.3 g, 152 mmol) in diethyl ether (290 mL). Dimethylformamide (14.4 g, 198 mmol) is added and the reaction is stirred at −78° C. for 15 minutes. The reaction is quenched with 1 N HCl (300 mL), is diluted with water, and extracted three times with ethyl acetate. The organic layer is dried over sodium sulfate and the solvent is removed under reduced pressure to give crude material that is purified by silica gel chromatography with a linear gradient of 0% to 50% CH$_2$Cl$_2$ in hexanes over 30 minutes to give the title compound (20.51 g, 61%). GC-MS m/e ($^{79}$Br/$^{81}$Br) 220, 222.

Preparation 38

1-(3-Bromophenyl)but-3-en-1-ol

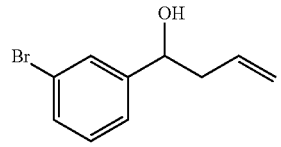

To a solution of 3-bromobenzaldehyde (15.8 g, 85.6 mmol) in dry diethyl ether (200 mL) at 0° C. under nitrogen atmosphere with stirring is added allylmagnesium bromide solution in ether (85.6 mL, 85.6 mmol) dropwise. The resulting mixture is warmed to room temperature over 1 hr and is quenched by the addition of 1 N HCl aqueous solution. The reaction is extracted with dichloromethane, washed with brine, dried over sodium sulfate, filtered, and concentrated under reduced pressure. The crude product is purified by silica gel chromatography eluting with 0% to 100% dichloromethane in hexanes over 50 minutes to give the title compound as a racemic mixture (17.01 g, 88%). ES/MS m/e ($^{79}$Br/$^{81}$Br) 227, 229 (M+1).

The following compounds in Table 25 are prepared essentially as described in the preparation of 1-(3-bromophenyl)but-3-en-1-ol.

TABLE 25

| Prep | Chemical name | MS (m/e) |
| --- | --- | --- |
| 38a | 1-(3-Bromo-4-fluorophenyl)but-3-en-1-ol | ES/MS ($^{79}$Br/$^{81}$Br) 243/245 (M − 1) |
| 38b | 1-(5-Bromo-2,4-difluorophenyl)but-3-en-1-ol | GC-MS ($^{79}$Br/$^{81}$Br) 262/264 (M+) |

Preparation 39

(1-(3-Bromophenyl)but-3-enyloxy)(tert-butyl)dimethylsilane

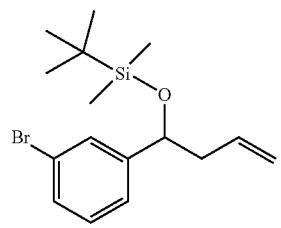

A solution of 1-(3-bromophenyl)but-3-en-1-ol (17.0 g, 74.9 mmol), 1H-imidazole (11.8 g, 172.2 mmol) and tert-butyldimethylchlorosilane (13.9 g, 89.8 mmol) in DMF (40 mL) is stirred at room temperature for 2 hours. The mixture is diluted with dichloromethane and is washed sequentially with water and saturated ammonium chloride aqueous solution. The organic layer is dried over sodium sulfate, filtered, and concentrated under reduced pressure to give a residue.

The crude product is purified by silica gel chromatography eluting with 5% ethyl acetate in hexanes to give the title compound as racemic mixture (23.9 g, 94%). $^1$H NMR (400 MHz, CDCl$_3$) δ 7.44 (s, 1H), 7.34 (d, 1H, J=7.5 Hz), 7.24-7.14 (m, 2H), 5.78-5.70 (m, 1H), 5.02-4.97 (m, 2H), 4.65-4.62 (m, 1H), 2.45-2.31 (m, 2H), 0.87 (s, 9H), 0.02 (s, 3H), 0.12 (s, 3H).

The following compounds in Table 26 are prepared essentially as described in the preparation of (1-(3-bromophenyl)but-3-enyloxy)(tert-butyl)dimethylsilane.

TABLE 26

| Prep | Chemical name | NMR |
|---|---|---|
| 39a | 1-(3-Bromo-4-fluorophenyl)but-3-en-1-ol | NMR[30] |
| 39b | (1-(5-Bromo-2,4-difluorophenyl)but-3-enyloxy)(tert-butyl)dimethylsilane | NMR[31] |

[30] $^1$H NMR (400 MHz, CDCl$_3$) δ 7.48-7.46 (m, 1H), 7.24-7.16 (m, 1H), 7.03 (t, 1H, J = 8.5 Hz), 5.76-5.67 (m, 1H), 5.02-4.96 (m, 2H), 4.64-4.61 (m, 1H), 2.43-2.31 (m, 2H), 0.87 (s, 9H), 0.02 (s, 3H), −0.13 (s, 3H).
[31] $^1$H NMR (400 MHz, CDCl$_3$) δ 7.63 (t, J = 7.7 Hz, 1H), 6.78 (dd, J = 8.4, 9.6 Hz, 1H), 5.76-5.68 (m, 1H), 5.01-4.95 (m, 3H), 2.36 (t, J = 6.5 Hz, 2H), 0.86 (s, 9H), 0.03 (s, 3H), −0.11 (s, 3H).

Preparation 40

3-(3-Bromophenyl)-3-(tert-butyldimethylsilyloxy)propanal

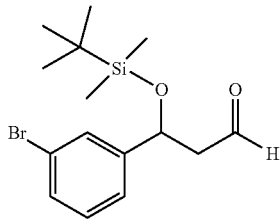

A solution of (1-(3-bromophenyl)but-3-enyloxy)(tert-butyl)dimethylsilane (23.9 g, 70.1 mmol) dichloromethane (120 mL) is cooled to −78° C. under nitrogen atmosphere. Ozone is then bubbled through the solution until it becomes blue. The mixture is flushed with nitrogen. Triethylamine (14.2 g, 140.2 mmol) is added to the solution. The mixture is warmed to room temperature and stirred for 4 hours. The mixture is concentrated under reduced pressure. The crude product is purified by silica gel chromatography eluting with a linear gradient of 0% to 8% ethyl acetate in hexanes over 25 minutes to give the title compound as a racemic mixture (17.9 g, 74%): $^1$H NMR (400 MHz, CDCl$_3$) δ 9.75-9.74 (m, 1H), 7.48 (d, 1H, J=1.8 Hz), 7.38-7.36 (m, 1H), 7.25-7.23 (m, 1H), 7.18 (t, 1H, J=7.7 Hz), 5.15 (dd, 1H, J=4.0, 7.9 Hz), 2.81 (ddd, 1H, J=15.9, 8.0, 2.5 Hz), 2.63-2.57 (m, 1H), 0.84-0.83 (m, 9H), 0.02-0.02 (m, 3H), −0.14 (s, 3H).

The following compounds in Table 27 are prepared essentially as described in the preparation of 3-(3-bromophenyl)-3-(tert-butyldimethylsilyloxy)propanal.

TABLE 27

| Prep | Chemical name | NMR |
|---|---|---|
| 40a | 3-(3-Bromo-4-fluorophenyl)-3-(tert-butyldimethylsilyloxy)propanal | NMR[32] |

TABLE 27-continued

| Prep | Chemical name | NMR |
|---|---|---|
| 40b | 3-(5-Bromo-2,4-difluorophenyl)-3-(tert-butyldimethylsilyloxy)propanal | NMR[33] |

[32] $^1$H NMR (400 MHz, CDCl$_3$) δ 9.74 (t, 1H, J = 2.0 Hz), 7.52 (dd, 1H, J = 2.1, 6.6 Hz), 7.25-7.21 (m, 1H), 7.06 (t, 1H, J = 8.4 Hz), 5.15 (dd, 1H, J = 4.3, 7.9 Hz), 2.81 (ddd, 1H, J = 16.1, 7.9, 2.4 Hz), 2.60 (ddd, 1H, J = 16.1, 4.3, 1.8 Hz), 0.84 (s, 9H), 0.03 (s, 3H), −0.14 (s, 3H).
[33] $^1$H NMR (400 MHz, CDCl$_3$) δ 9.74 (ddd, J = 1.9, 2.5 Hz, 1H), 7.68-7.64 (m, 1H), 6.83 (dd, J = 8.2, 9.7 Hz, 1H), 5.43 (ddd, J = 7.9, 3.9, 0.5 Hz, 1H), 2.78 (ddd, J = 16.1, 7.9, 2.7 Hz, 1H), 2.62 (ddd, J = 16.1, 3.9, 1.7 Hz, 1H), 0.85 (s, 9H), 0.05 (s, 3H), −0.11 (s, 3H).

Preparation 41

1-(3-Bromophenyl)-1-(tert-butyldimethylsilyloxy)hex-5-en-3-ol

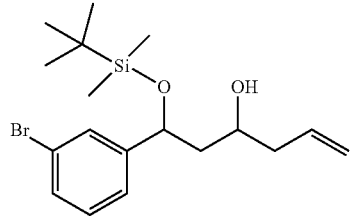

To a 0° C. solution of 3-(3-bromophenyl)-3-(tert-butyldimethylsilyloxy)propanal (17.9 g, 52.1 mmol) in dry diethyl ether (150 mL) is added 1 M allylmagnesium bromide solution in ether (52.1 mL, 52.1 mmol). The resulting mixture is warmed to room temperature over 1 hour. The mixture is diluted with dichloromethane and is quenched by addition of saturated aqueous solution of ammonium chloride. The mixture is extracted three times with dichloromethane. The combined organic layers are washed with brine, dried over sodium sulfate, filtered, and concentrated under reduced pressure to give the title compound as a racemic diastereomeric mixture (18.8 g, 84%). $^1$H NMR (400 MHz, CDCl$_3$) δ 7.45 (s, 1H), 7.38-7.34 (m, 1H), 7.24-7.21 (m, 1H), 7.19-7.15 (m, 1H), 5.84-5.76 (m, 1H), 5.09-5.04 (m, 1H), 5.00 (t, J=5.3 Hz, 1H), 4.86-4.80 (m, 1H), 3.83-3.75 (m, 2H), 2.23-2.15 (m, 2H), 1.80-1.69 (m, 2H), 0.89 (d, 9H, J=6.6 Hz), 0.06-0.04 (m, 3H), −0.17 (d, J=40.4 Hz, 3H).

The following compounds in Table 28 are prepared essentially as described in the preparation of 1-(3-bromophenyl)-1-(tert-butyldimethylsilyloxy)hex-5-en-3-ol.

TABLE 28

| Prep | Chemical name | NMR |
|---|---|---|
| 41a | 1-(3-Bromo-4-fluorophenyl)-1-(tert-butyldimethylsilyloxy)hex-5-en-3-ol | NMR[34] |
| 41b | 1-(5-Bromo-2,4-difluorophenyl)-1-(tert-butyldimethylsilyloxy)hex-5-en-3-ol | NMR[35] |

[34] $^1$H NMR (400 MHz, CDCl$_3$) δ 7.49 (dt, J = 6.6, 2.0 Hz, 1H), 7.23-7.20 (m, 1H), 7.05 (t, J = 8.4 Hz, 1H), 5.82-5.76 (m, 1H), 5.09-5.04 (m, 1H), 4.98 (t, J = 5.3 Hz, 1H), 4.88-4.82 (m, 1H), 3.83-3.74 (m, 2H), 3.05-2.22-2.15 (m, 2H), 1.85-1.71 (m, 2H), 0.88-0.87 (m, 9H), 0.05-0.04 (m, 3H), −0.17 (d, J = 34.4 Hz, 3H).
[35] $^1$H NMR (400 MHz, CDCl$_3$) δ 7.68-7.60 (m, 1H), 6.83-6.78 (m, 1H), 5.82-5.76 (m, 1H), 5.28-5.24 (m, 0.5H), 5.13-5.09 (m, 0.5H), 5.09-5.05 (m, 2H), 3.82-3.79 (m, 1H), 2.96 (d, J = 1.9 Hz, 0.5H), 2.59 (d, J = 3.2 Hz, 0.5H), 2.22-2.19 (m, 2H), 1.83-1.73 (m, 2H), 0.88 (s, 4.5H), 0.87 (s, 4.5H), 0.06 (s, 1.5H), 0.06 (s, 1.5H), −0.11 (s, 1.5H), −0.19 (s, 1.5H).

Preparation 42

1-(3-Bromophenyl)hex-5-ene-1,3-diol

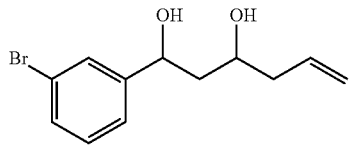

To a solution of 1-(3-bromophenyl)-1-(tert-butyldimethylsilyloxy)hex-5-en-3-ol (18.8 g, 44.0 mmol) in tetrahydrofuran (60 mL) is added 1 M tetrabutylammonium fluoride solution in THF (66.0 mL, 66.0 mmol). The resulting mixture is stirred at room temperature for 2 hours. The mixture is diluted with dichloromethane and is washed sequentially with water and saturated ammonium chloride aqueous solution. The organic layer is dried over sodium sulfate, filtered, and concentrated under reduced pressure to give a residue. The crude product is purified by silica gel chromatography eluting with a linear gradient of 20% to 40% ethyl acetate in hexanes over 26 minutes to give the title compound as racemic diastereomeric mixture (11.8 g, 99%). $^1$H NMR (400 MHz, CDCl$_3$) δ 7.52 (s, 1H), 7.38-7.36 (m, 1H), 7.28-7.24 (m, 1H), 7.22-7.17 (m, 1H), 5.83-5.75 (m, 1H), 5.15-5.11 (m, 2H), 5.03-4.89 (m, 1H), 4.00-3.90 (m, 1H), 2.32-2.21 (m, 2H), 1.96-1.89 (m, 2H).

The following compounds in Table 29 are prepared essentially as described in the preparation of 1-(3-bromophenyl)hex-5-ene-1,3-diol.

TABLE 29

| Prep | Chemical name | NMR |
|---|---|---|
| 42a | 1-(3-Bromo-4-fluorophenyl)hex-5-ene-1,3-diol | NMR[36] |
| 42b | 1-(5-Bromo-2,4-difluorophenyl)hex-5-ene-1,3-diol | NMR[37] |

[36]$^1$H NMR (400 MHz, CDCl$_3$) δ 7.56 (dt, J = 6.6, 2.0 Hz, 1H), 7.26-7.22 (m, 1H), 7.09-7.04 (m, 1H), 5.82-5.76 (m, 1H), 5.16-5.11 (m, 2H), 5.05-4.89 (m, 1H), 3.99-3.93 (m, 1H), 2.32-2.27 (m, 2H), 1.89-1.78 (m, 2H).
[37]$^1$H NMR (400 MHz, CDCl$_3$) δ 7.77-7.73 (m, 1H), 6.84-6.78 (m, 1H), 5.82-5.76 (m, 1H), 5.27-5.15 (m, 3H), 4.07-4.02 (m, 1H), 3.85-3.81 (m, 0.5H), 3.62 (d, J = 5.4 Hz, 0.5H), 2.46 (dd, J = 1.2, 2.9 Hz, 0.5H), 2.33-2.31 (m, 2.5H), 1.94-1.88 (m, 1H), 1.85-1.81 (m, −1H), 1.69 (dt, J = 14.5, 10.2 Hz, 1H).

Preparation 43

1-(3-Bromophenyl)-3-hydroxyhex-5-en-1-one

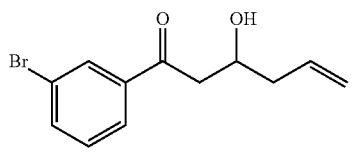

A mixture of 1-(3-bromophenyl)hex-5-ene-1,3-diol (2.60 g, 9.59 mmol) and manganese(IV) oxide (9.81 g, 95.9 mmol) in dichloromethane (80 mL) is heated and stirred for 4 h under reflux. The reaction mixture is filtered through a pad of diatomaceous earth and the residue is washed twice with dichloromethane. The filtrate is concentrated under reduced pressure to afford the title compound (2.12 g, 82%). $^1$H NMR (400 MHz, CDCl$_3$) δ 8.05 (d, 1H, J=1.8 Hz), 7.85 (d, 1H, J=7.5 Hz), 7.69-7.52 (m, 1H), 7.35-7.31 (m, 1H), 5.91-5.82 (m, 1H), 5.18-5.12 (m, 2H), 4.32-4.26 (m, 1H), 3.09-3.00 (m, 2H), 2.39-2.30 (m, 2H).

The following compounds in Table 30 are prepared essentially as described in the preparation of 1-(3-bromophenyl)-3-hydroxyhex-5-en-1-one.

TABLE 30

| Prep | Chemical name | NMR |
|---|---|---|
| 43a | 1-(3-Bromo-4-fluorophenyl)-3-hydroxyhex-5-en-1-one | NMR[38] |
| 43b | 1-(5-Bromo-2,4-difluorophenyl)-3-hydroxyhex-5-en-1-one | NMR[39] |

[38]$^1$H NMR (400 MHz, CDCl$_3$) δ 8.16 (dd, J = 2.2, 6.6 Hz, 1H), 7.89 (ddd, J = 8.6, 4.7, 2.2 Hz, 1H), 7.19 (t, J = 8.3 Hz, 1H), 5.91-5.83 (m, 1H), 5.19-5.15 (m, 2H), 4.31-4.30 (m, 1H), 3.12-2.98 (m, 2H), 2.39-2.36 (m, 2H).
[39]$^1$H NMR (400 MHz, CDCl$_3$) δ 8.11 (t, J = 7.7 Hz, 1H), 6.94 (dd, J = 8.0, 10.4 Hz, 1H), 5.88-5.79 (m, 1H), 5.15-5.12 (m, 2H), 4.29-4.26 (m, 1H), 3.14-3.03 (m, 2H), 2.79 (d, J = 3.5 Hz, 1H), 2.35-2.30 (m, 2H).

Preparation 44

1-(3-Bromophenyl)-3-(tert-butyldimethylsilyloxy)hex-5-en-1-one

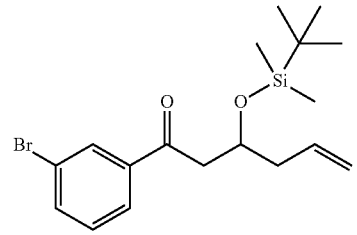

A mixture of 1-(3-bromophenyl)-3-hydroxyhex-5-en-1-one (9.08 g, 33.7 mmol), 1H-imidazole (5.34 g, 77.6 mmol) and tert-butyldimethylchlorosilane (6.29 g, 40.5 mmol) in DMF (40 mL) is stirred at room temperature for 2 h. The mixture is diluted with dichloromethane and is washed sequentially with water and saturated ammonium chloride aqueous solution. The organic layer is dried over sodium sulfate, filtered, and concentrated under reduced pressure. The crude product is purified by silica gel chromatography eluting with a linear gradient of 0% to 5% ethyl acetate in hexanes over 20 minutes to give the title compound as a racemic mixture (11.3 g, 88%). ES/MS m/e ($^{79}$Br/$^{81}$Br) 383, 385 (M+1).

The following compounds in Table 31 are prepared essentially as described in the preparation of 1-(3-bromophenyl)-3-(tert-butyldimethylsilyloxy)hex-5-en-1-one.

TABLE 31

| Prep | Chemical name | NMR |
|---|---|---|
| 44a | 1-(3-Bromo-4-fluorophenyl)-3-(tert-butyldimethylsilyloxy)hex-5-en-1-one | NMR[40] |
| 44b | 1-(5-Bromo-2,4-difluorophenyl)-3-(tert-butyldimethylsilyloxy)hex-5-en-1-one | NMR[41] |

[40]$^1$H NMR (400 MHz, CDCl$_3$) δ 8.16 (dd, J = 2.1, 6.6 Hz, 1H), 7.89 (ddd, J = 8.6, 4.7, 2.1 Hz, 1H), 7.19-7.15 (m, 1H), 5.90-5.82 (m, 1H), 5.12-5.07 (m, 2H), 3.15 (dd, J = 7.7, 15.3 Hz, 1H), 2.82 (dd, J = 4.6, 15.3 Hz, 1H), 2.38-2.33 (m, 2H), 0.88-0.78 (m, 9H), 0.04-0.01 (m, 6H).
[41]$^1$H NMR (400 MHz, CDCl$_3$) δ 8.05-8.01 (m, 1H), 6.92 (ddd, J = 10.3, 8.0, 0.3 Hz, 1H), 5.85-5.78 (m, 1H), 5.06 (d, J = 1.2 Hz, 1H), 5.03-5.01 (m, 1H), 4.40-4.35 (m, 1H), 3.12-2.99 (m, 2H), 2.30-2.27 (m, 2H), 0.78 (s, 9H), 0.03 (s, 3H), −0.07 (s, 3H).

Preparation 45

1-Benzyl-6a-(3-bromophenyl)-5-(tert-butyldimethyl-silyloxy)hexahydro-1H-cyclopenta[c]isoxazole

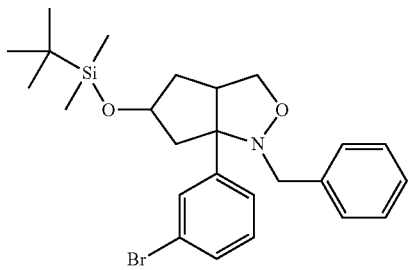

To a solution of 1-(3-bromophenyl)-3-(tert-butyldimethyl-silyloxy)hex-5-en-1-one (6.84 g, 17.8 mmol) and N-benzyl-hydroxylamine (2.86 g, 23.2 mmol) in THF (60 mL) is added Ti(OEt)$_4$ (8.14 g, 35.7 mmol). The reaction mixture is heated to 70° C. in a sealed tube. After 2 h, the temperature is increased to 80° C. and stirring is continued for 3 days. The reaction mixture is cooled to room temperature. Water and ethyl acetate are added and the mixture is stirred vigorously for 15 minutes. The solids are allowed to settle and the organic and aqueous layers are decanted through a pad of diatomaceous earth. The layers are separated and the aqueous layer is extracted three times with ethyl acetate. The combined organic layers are washed with brine, dried over sodium sulfate, filtered, and concentrated under reduced pressure. The crude product is purified by silica gel chromatography eluting with 0% to 20% ethyl acetate in hexanes gradient over 20 minutes to give the title compound as a diastereomeric mixture (7.42 g, 85%). ES/MS m/e ($^{79}$Br/$^{81}$Br) 488, 490 (M+1).

The following compounds in Table 32 are prepared essentially as described in the preparation of 1-benzyl-6a-(3-bromophenyl)-5-(tert-butyldimethylsilyloxy)hexahydro-1H-cyclopenta[c]isoxazole.

Preparation 46

1-Benzyl-5-(tert-butyldimethylsilyloxy)-6a-(3'-methoxybiphenyl-3-yl)hexahydro-1H-cyclopenta[c]isoxazole

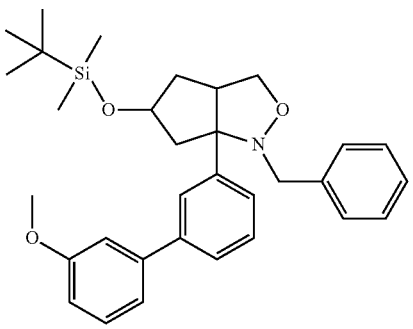

To a stirred solution of 1-benzyl-6a-(3-bromophenyl)-5-(tert-butyldimethylsilyloxy)hexahydro-1H-cyclopenta[c]isoxazole (7.42 g, 15.2 mmol) in 1,2-dimethoxyethane (30 mL) is added 2 M aqueous solution of sodium carbonate (22.8 mL, 45.6 mmol), 3-methoxyphenylboronic acid (2.77 g, 18.2 mmol) and (1,1'-bis(diphenylphosphino)ferrocene)palladium(II) chloride (0.759 g, 0.911 mmol). The reaction mixture is heated at 110° C. for 7 hours. The reaction is cooled, diluted with ethyl acetate, and filtered. The resulting filtrate is separated and the aqueous layer is extracted three times with ethyl acetate. The combined organic layers are washed with brine, dried over sodium sulfate, filtered, and concentrated under reduced pressure. The crude product is purified by silica gel chromatography eluting with 10% to 20% ethyl acetate in hexanes gradient over 20 minutes to give the title compound (7.59 g, 92%). ES/MS m/e: 516 (M+1).

TABLE 32

| Prep | Chemical name | ES/MS (m/e) (M + 1) |
|---|---|---|
| 45a | 6a-(3-Bromophenyl)-5-(tert-butyldimethylsilyloxy)-1-(2,4-dimethoxybenzyl)hexahydro-1H-cyclopenta[c]isoxazole[42] | ($^{79}$Br/$^{81}$Br) 548/550 |
| 45b | 6a-(3-Bromo-4-fluorophenyl)-5-(tert-butyldimethylsilyloxy)-1-(2,4-dimethoxybenzyl)hexahydro-1H-cyclopenta[c]isoxazole[42] | ($^{79}$Br/$^{81}$Br) 566, 568 |
| 45c | Racemic (3aRS,5RS,6aSR)-6a-(5-Bromo-2,4-difluorophenyl)-5-(tert-butyldimethylsilyloxy)-1-(2,4-dimethoxybenzyl)hexahydro-1H-cyclopenta[c]isoxazole[42] | ($^{79}$Br/$^{81}$Br) 584, 586 |
| 45d | 6a-(3-Bromo-4-fluorophenyl)-5-(tert-butyldimethylsilyloxy)-1-(4-methoxybenzyl)hexahydro-1H-cyclopenta[c]isoxazole[43] | ($^{79}$Br/$^{81}$Br) 536, 538 |

[42] N-(2,4-dimethoxybenzyl)hydroxylamine utilized instead of N-benzylhydroxylamine
[43] N-(4-methoxybenzyl)hydroxylamine utilized instead of N-benzylhydroxylamine

Preparation 47

(2-Amino-4-(tert-butyldimethylsilyloxy)-2-(3'-methoxybiphenyl-3-yl)cyclopentyl)methanol

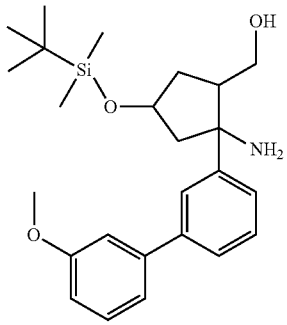

A mixture of 1-benzyl-5-(tert-butyldimethylsilyloxy)-6a-(3'-methoxybiphenyl-3-yl)hexahydro-1H-cyclopenta[c]isoxazole (2.04 g, 3.76 mmol) and palladium on carbon (0.400 g) in acetic acid (10 mL) is stirred at room temperature under hydrogen atmosphere (50 psi) for 19 hours. The reaction is filtered through a pad of diatomaceous earth and the filter cake is washed with methanol three times and the filtrate is concentrated under reduced pressure. The residue is dissolved in dichloromethane, the pH adjusted to pH 12 by addition of saturated aqueous sodium bicarbonate, and is extracted three times with dichloromethane. The combined organic layers are dried over sodium sulfate, filtered, and concentrated under reduced pressure to give the title compound. ES/MS m/e: 428 (M+1).

Preparation 48

N-(4-(tert-Butyldimethylsilyloxy)-2-(hydroxymethyl)-1-(3'-methoxybiphenyl-3-yl)cyclopentylcarbamothioyl)benzamide

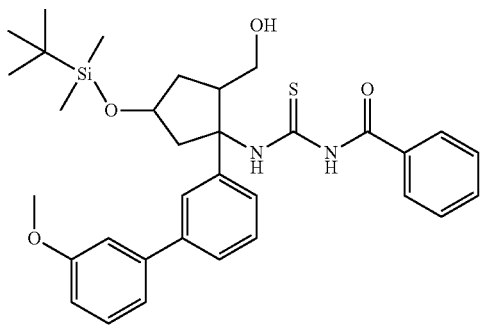

A solution of (2-amino-4-(tert-butyldimethylsilyloxy)-2-(3'-methoxybiphenyl-3-yl)cyclopentyl)methanol (9.44 g, 22.1 mmol) and benzoyl isothiocyanate (3.49 g, 21.0 mmol) in THF (88 mL) is stirred for 1.5 hours at room temperature and concentrated under reduced pressure. The crude product is purified by silica gel chromatography eluting with a linear gradient of 0% to 5% methanol in dichloromethane over 27 minutes to give the title compound (9.61 g, 70%). ES/MS m/e: 589 (M−1).

Preparation 49

Racemic N-((4aRS,6RS,7aSR)-6-(tert-Butyldimethylsilyloxy)-7a-(3'-methoxybiphenyl-3-yl)-4,4a,5,6,7,7a-hexahydrocyclopenta[d][1,3]thiazin-2-yl)benzamide

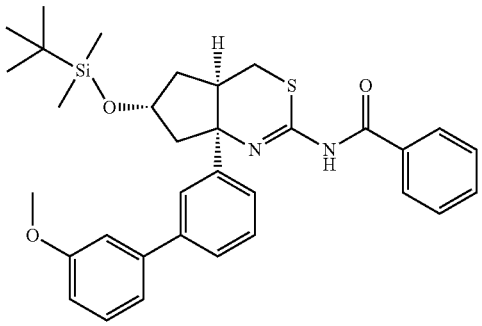

A solution of N-(4-(tert-butyldimethylsilyloxy)-2-(hydroxymethyl)-1-(3'-methoxybiphenyl-3-yl)cyclopentylcarbamothioyl)benzamide (6.37 g, 8.41 mmol) and triphenylphosphine (4.41 g, 16.8 mmol) in THF (30 mL) is added to a separate solution of di-tert-butyl azodicarboxylate (3.87 g, 16.8 mmol) in THF (15 mL) at room temperature. The reaction is stirred for 30 minutes and is concentrated under reduced pressure. The crude product is purified by silica gel chromatography eluting with a linear gradient of 10% to 40% ethyl acetate in hexanes over 26 minutes to give a crude diastereomeric mixture (7.39 g, 100%). The mixture is purified again on silica gel chromatography to separate the diastereomers eluting with 15% ethyl acetate in hexanes to give the title compound as a racemic mixture (1.47 g, 24%). ES/MS m/e: 573 (M+1).

The following compound in Table 33 is prepared essentially as described in the preparation of racemic N-((4aRS,6RS,7aSR)-6-(tert-butyldimethylsilyloxy)-7a-(3'-methoxybiphenyl-3-yl)-4,4a,5,6,7,7a-hexahydrocyclopenta[d][1,3]thiazin-2-yl)benzamide.

TABLE 33

| Prep | Chemical name | ES/MS (m/e) (M + 1) |
|---|---|---|
| 49a | N-(6-(tert-Butyldimethylsilyloxy)-7a-(3'-methoxybiphenyl-3-yl)-4,4a,5,6,7,7a-hexahydrocyclopenta[d][1,3]thiazin-2-yl)benzamide | 573 |

Preparation 50

Racemic N-((4aRS,6RS,7aSR)-6-Hydroxy-7a-(3'-methoxybiphenyl-3-yl)-4,4a,5,6,7,7a-hexahydrocyclopenta[d][1,3]thiazin-2-yl)benzamide

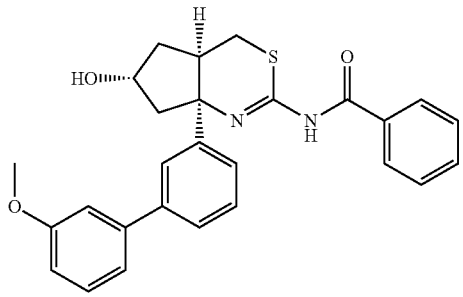

To a solution of racemic N-((4aRS,6RS,7aSR)-6-(tert-butyldimethylsilyloxy)-7a-(3'-methoxybiphenyl-3-yl)-4,4a,5,6,7,7a-hexahydrocyclopenta[d][1,3]thiazin-2-yl)benzamide (1.47 g, 2.31 mmol) in acetonitrile (6 mL) is added 20-25% aqueous fluorosilicic acid (2.82 g, 4.62 mmol) and the resulting mixture is stirred at room temperature for 3 h. The reaction is diluted with ethyl acetate and quenched with saturated aqueous sodium bicarbonate. The mixture is washed with water and brine. The organic layer is dried over sodium sulfate, filtered, and concentrated under reduced pressure. The crude product is purified by silica gel chromatography eluting with a linear gradient of 10% to 60% ethyl acetate in hexanes over 40 minutes to give the title compound as a racemic mixture (0.709 g, 64%). ES/MS m/e: 459 (M+1).

Preparation 51

N-((4aR,6R,7aS)-6-Hydroxy-7a-(3'-methoxybiphenyl-3-yl)-4,4a,5,6,7,7a-hexahydrocyclopenta[d][1,3]thiazin-2-yl)benzamide

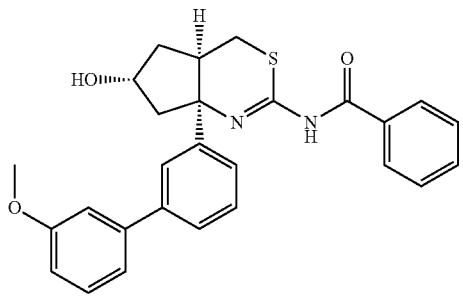

Racemic N-((4aRS,6RS,7aSR)-6-hydroxy-7a-(3'-methoxybiphenyl-3-yl)-4,4a,5,6,7,7a-hexahydrocyclopenta[d][1,3]thiazin-2-yl)benzamide (0.689 g, 1.50 mmol) is purified by chiral HPLC: 2.1×25 cm Chiralpak AD-H, 5 micron, 35% IPA/CO$_2$, flow rate: 70 mL/min, UV: 225 nm. The first eluting isomer is isolated to provide the enantiomerically enriched title compound (0.242 g, 35%). ES/MS m/e: 459 (M+1).

Preparation 52

N-((4aR,6R,7aS)-6-Methoxy-7a-(3'-methoxybiphenyl-3-yl)-4,4a,5,6,7,7a-hexahydrocyclopenta[d][1,3]thiazin-2-yl)benzamide

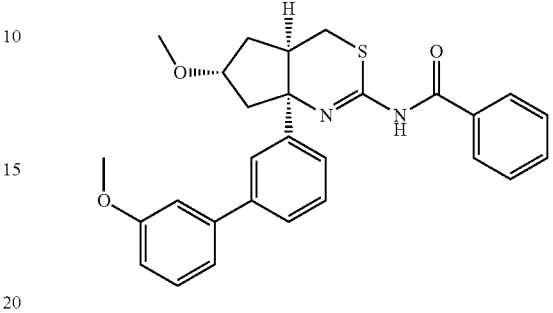

To a 0° C. mixture of N-((4aR,6R,7aS)-6-hydroxy-7a-(3'-methoxybiphenyl-3-yl)-4,4a,5,6,7,7a-hexahydrocyclopenta[d][1,3]thiazin-2-yl)benzamide (0.086 g, 0.169 mmol) and 48% aqueous fluoroboric acid (0.031 g, 0.169 mmol) in dichloromethane (0.6 mL) is added 2 M trimethylsilyldiazomethane in hexane (0.101 mL, 0.202 mmol). The mixture is stirred at 0° C. for 30 minutes and is poured into saturated aqueous solution of sodium bicarbonate. The mixture is diluted with water and is extracted with dichloromethane. The organic layer is washed sequentially with water and brine and is dried over sodium sulfate. The solvent is removed under reduced pressure and the crude product is purified by silica gel chromatography eluting with a linear gradient of 10% to 60% ethyl acetate in hexanes over 20 minutes to give the title compound (0.038 g, 48%). ES/MS m/e: 473 (M+1).

Preparation 53

N-((4aR,6R,7aS)-7a-(3'-Methoxybiphenyl-3-yl)-6-(methoxymethoxy)-4,4a,5,6,7,7a-hexahydrocyclopenta[d][1,3]thiazin-2-yl)benzamide

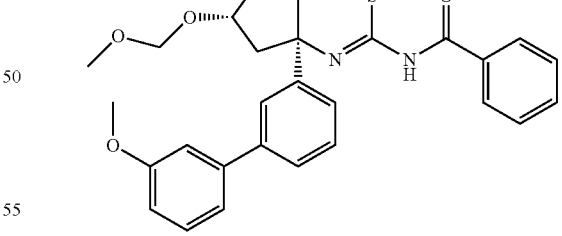

To a stirred 0° C. solution of N-((4aR,6R,7aS)-6-hydroxy-7a-(3'-methoxybiphenyl-3-yl)-4,4a,5,6,7,7a-hexahydrocyclopenta[d][1,3]thiazin-2-yl)benzamide (0.087 g, 0.190 mmol) in anhydrous dichloromethane (0.6 mL) is added chloromethoxymethane (0.031 g, 0.379 mmol), followed by diisopropylethylamine (0.049 g, 0.379 mmol). The resulting mixture is stirred at 0° C. for 1 hour, and then is warmed to room temperature over 24 h. The mixture is diluted with dichloromethane, quenched by addition of saturated aqueous solution of sodium bicarbonate, and is extracted three times with dichloromethane. The combined organic layers are washed with water and brine. The organic layer is dried over sodium sulfate, filtered, and concentrated under reduced pressure. The crude product is purified by silica gel chromatography eluting with a linear gradient of 0% to 60% ethyl acetate in hexanes over 26 minutes to give the title compound (0.089, 93%). ES/MS m/e: 503 (M+1).

Preparation 54

6-(tert-Butyldimethylsilyloxy)-7a-(3'-methoxybiphenyl-3-yl)-4,4a,5,6,7,7a-hexahydrocyclopenta[d][1,3]thiazin-2-amine

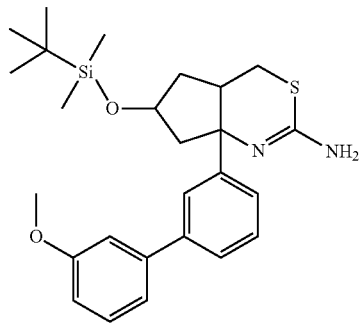

A mixture of N-(6-(tert-butyldimethylsilyloxy)-7a-(3'-methoxybiphenyl-3-yl)-4,4a,5,6,7,7a-hexahydrocyclopenta[d][1,3]thiazin-2-yl)benzamide (0.200 g, 0.349 mmol) and hydrazine (0.559 g, 1.75 mmol) in ethanol (4 mL) is stirred at 120° C. over night. The mixture is cooled, diluted with ethyl acetate and is washed with water. The organic layer is dried over sodium sulfate and the solvent is removed under reduced pressure to give the title compound (0.164 g, 100%). ES/MS m/e: 469 (M+1).

Preparation 55

Racemic (3aRS,5RS,6aSR)-6a-(3-Bromo-4-fluorophenyl)-1-(2,4-dimethoxybenzyl)hexahydro-1H-cyclopenta[c]isoxazol-5-ol

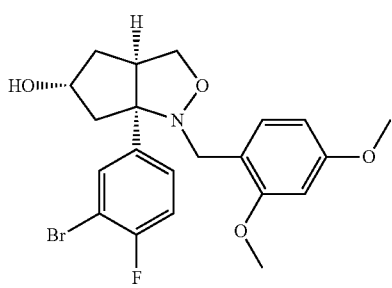

To a solution of 6a-(3-bromo-4-fluorophenyl)-5-(tert-butyldimethylsilyloxy)-1-(2,4-dimethoxybenzyl)hexahydro-1H-cyclopenta[c]isoxazole (3.00 g, 4.77 mmol) in THF (10 mL) is added 1 N tetrabutylammonium fluoride solution in THF (7.15 mL, 7.15 mmol). After stirring at room temperature for 2 hours, the reaction mixture is concentrated under reduced pressure to afford a residue that is diluted with dichloromethane and washed with water and brine. The organic layer is dried over sodium sulfate, filtered, and the filtrate is concentrated under reduced pressure to give a residue that is purified by silica gel chromatography eluting with a linear gradient of 0% to 10% methanol in dichloromethane over 20 minutes to give the title compound as a diastereomeric mixture (2.26 g, 100%). This mixture is purified again on silica gel chromatography to separate the diastereomers eluting with a linear gradient of 0% to 15% ethyl acetate in hexanes over 15 minutes to give the title compound as a racemic mixture (0.852 g, 37%). ES/MS m/e ($^{79}$Br/$^{81}$Br) 452, 454 (M+1).

The following compounds in Table 34 are prepared essentially as described in the preparation of racemic (3aRS,5RS,6aSR)-6a-(3-bromo-4-fluorophenyl)-1-(2,4-dimethoxybenzyl)hexahydro-1H-cyclopenta[c]isoxazol-5-ol.

TABLE 34

| Prep | Chemical name | ES/MS (m/e) (M + 1) |
|---|---|---|
| 55a | 6a-(3-Bromophenyl)-1-(2,4-dimethoxybenzyl)hexahydro-1H-cyclopenta[c]isoxazol-5-ol[44] | ($^{79}$Br/$^{81}$Br) 434/436 |
| 55b | Racemic (3aRS,5RS,6aSR)-6a-(3-Bromophenyl)-1-(2,4-dimethoxybenzyl)hexahydro-1H-cyclopenta[c]isoxazol-5-ol | ($^{79}$Br/$^{81}$Br) 434/436 |
| 55c | Racemic (3aRS,5RS,6aSR)-6a-(5-Bromo-2,4-difluorophenyl)-1-(2,4-dimethoxybenzyl)hexahydro-1H-cyclopenta[c]isoxazol-5-ol | ($^{79}$Br/$^{81}$Br) 470/472 |
| 55d | Racemic (3aRS,5RS,6aSR)-6a-(3-Bromo-4-fluorophenyl)-1-(4-methoxybenzyl)hexahydro-1H-cyclopenta[c]isoxazol-5-ol | ($^{79}$Br/$^{81}$Br) 422/424 |

[44]Isolated as a racemic mixture of diastereomers.

Preparation 56

Racemic (3aRS,5RS,6aSR)-6a-(3-Bromophenyl)-1-(2,4-dimethoxybenzyl)-5-methoxyhexahydro-1H-cyclopenta[c]isoxazole

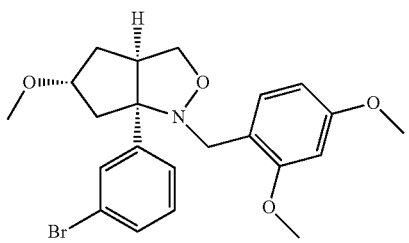

Sodium hydride (0.076 g, 1.89 mmol) is added to a 0° C. solution of racemic (3aRS,5RS,6aSR)-6a-(3-bromophenyl)-1-(2,4-dimethoxybenzyl)hexahydro-1H-cyclopenta[c]isoxazol-5-ol (0.684 g, 1.57 mmol) in DMF (7 mL). The reaction is warmed to room temperature for 10 minutes and then cooled to 0° C. Methyl iodide (0.246 g, 1.73 mmol) is added and the reaction is stirred at room temperature for 6 hours. Additional sodium hydride (0.032 g, 0.790 mmol) and methyl iodide (0.112 g, 0.790 mmol) is added and the reaction is stirred at room temperature for 18 hours. The reaction is quenched with water and extracted with ethyl acetate. The organic layer is dried over sodium sulfate, filtered and the solvent is removed under reduced pressure. The resulting residue is purified by silica gel chromatography with 10% ethyl acetate in $CH_2Cl_2$ to give the title compound (0.443 g, 63%). ES/MS m/e ($^{79}Br/^{81}Br$) 448, 450 (M+1).

The following compounds in Table 35 are prepared essentially by the method of racemic (3 aRS,5RS,6aSR)-6a-(3-bromophenyl)-1-(2,4-dimethoxybenzyl)-5-methoxyhexahydro-1H-cyclopenta[c] isoxazole.

TABLE 35

| Prep | Chemical name | ES/MS (m/e) (M + 1) |
|---|---|---|
| 56a | 6a-(3-Bromophenyl)-1-(2,4-dimethoxybenzyl)-5-methoxyhexahydro-1H-cyclopenta[c]isoxazole[45] | ($^{79}Br/^{81}Br$) 448/450 |
| 56b | Racemic (3aRS,5RS,6aSR)-6a-(3-Bromo-4-fluorophenyl)-1-(2,4-dimethoxybenzyl)-5-methoxyhexahydro-1H-cyclopenta[c]isoxazole | ($^{79}Br/^{81}Br$) 466/468 |

[45]Isolated as a mixture of diastereomers.

Preparation 57

Racemic (3aRS,5RS,6aSR)-6a-(3-Bromo-4-fluorophenyl)-5-isopropoxy-1-(4-methoxybenzyl)hexahydro-1H-cyclopenta[c]isoxazole

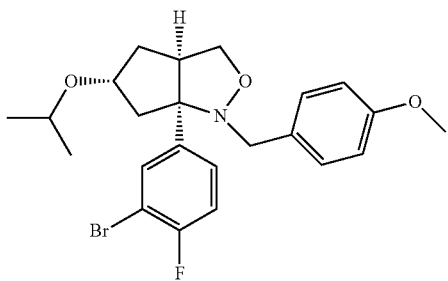

To a mixture of racemic (3aRS,5RS,6aSR)-6a-(3-bromo-4-fluorophenyl)-1-(4-methoxybenzyl)hexahydro-1H-cyclopenta[c]isoxazol-5-ol (1.72 g, 4.07 mmol) in dichloromethane (2.5 mL) is added silver trifluoromethanesulfonate (2.62 g, 10.2 mmol) and powdered dried 4A sieves (1.50 g). A solution of 2-iodopropane (1.73 g, 10.2 mmol) in dichloromethane (0.5 mL) is added to the mixture over 15 minutes. The thick mixture is stirred at room temperature overnight. The mixture is diluted with dichloromethane and is filtered through diatomaceous earth. The solvent is removed under reduced pressure and the residue is purified by silica gel chromatography with a linear gradient of 0% to 10% ethyl acetate in dichloromethane over 15 minutes to give the title compound (0.466 g, 25%). ES/MS m/e ($^{79}Br/^{81}Br$) 464, 466 (M+1).

Preparation 58

Racemic (3 aRS,5RS,6aSR)-6a-(3-Bromo-4-fluorophenyl)hexahydro-1H-cyclopenta[c] isoxazol-5-ol

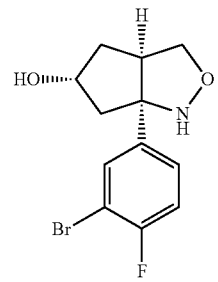

A mixture of racemic (3aRS,5RS,6aSR)-6a-(3-bromo-4-fluorophenyl)-1-(2,4-dimethoxybenzyl)hexahydro-1H-cyclopenta[c]isoxazol-5-ol (0.852 g, 1.79 mmol) and triethylsilane (0.624 g, 5.37 mmol) in TFA (4 mL) is heated to 80° C. for 3 h. The reaction is cooled to room temperature and concentrated under reduced pressure to afford a residue that is purified on a SCX column washing sequentially with dichloromethane, methanol and 7 N $NH_3$ in MeOH to give the title compound as racemic mixture (0.57 g, 100%). ES/MS m/e ($^{79}Br/^{81}Br$) 302, 304 (M+1).

The following compounds in Table 36 are prepared essentially as described in the preparation of racemic (3aRS,5RS,6aSR)-6a-(3-bromo-4-fluorophenyl)hexahydro-1H-cyclopenta[c]isoxazol-5-ol.

TABLE 36

| Prep | Chemical name | ES/MS (m/e) (M + 1) |
|---|---|---|
| 58a | 6a-(3-Bromophenyl)hexahydro-1H-cyclopenta[c]isoxazol-5-ol[46] | ($^{79}Br/^{81}Br$) 284/286 |
| 58b | Racemic (3aRS,5RS,6aSR)-6a-(5-Bromo-2,4-difluorophenyl)hexahydro-1H-cyclopenta[c]isoxazol-5-ol | ($^{79}Br/^{81}Br$) 320/322 |
| 58c | Racemic (3aRS,5RS,6aSR)-6a-(3-Bromo-4-fluorophenyl)hexahydro-1H-cyclopenta[c]isoxazol-5-ol | ($^{79}Br/^{81}Br$) 302/304 |
| 58d | 6a-(3-Bromophenyl)-5-methoxyhexahydro-1H-cyclopenta[c]isoxazole[46] | ($^{79}Br/^{81}Br$) 298/300 |
| 58e | Racemic (3aRS,5RS,6aSR)-6a-(3-Bromophenyl)-5-methoxyhexahydro-1H-cyclopenta[c]isoxazole | ($^{79}Br/^{81}Br$) 298/300 |
| 58f | Racemic (3aRS,5RS,6aSR)-6a-(3-Bromo-4-fluorophenyl)-5-methoxyhexahydro-1H-cyclopenta[c]isoxazole | ($^{79}Br/^{81}Br$) 316/318 |
| 58g | Racemic (3aRS,5RS,6aSR)-6a-(3-Bromo-4-fluorophenyl)-5-isopropoxyhexahydro-1H-cyclopenta[c]isoxazole | ($^{79}Br/^{81}Br$) 344/346 |

[46]Isolated as a mixture of diastereomers.

Preparation 59

Racemic (1RS,3SR,4RS)-3-Amino-3-(3-bromo-4-fluorophenyl)-4-(hydroxymethyl)cyclopentanol

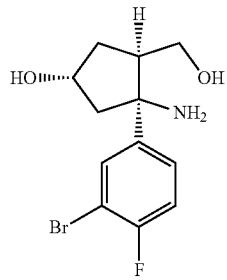

A mixture of racemic(3aRS,5RS,6aSR)-6a-(3-bromo-4-fluorophenyl)hexahydro-1H-cyclopenta[c]isoxazol-5-ol (0.57 g, 1.89 mmol) and zinc (0.617 g, 9.43 mmol) in acetic acid (12.6 mL) is heated to 42° C. under a nitrogen atmosphere for 3 hours. The reaction is cooled to room temperature, filtered, and concentrated under reduced pressure to afford a residue that is purified on a SCX column washing sequentially with dichloromethane, methanol and 7 N $NH_3$ in MeOH to give the title compound as racemic mixture (0.53 g, 92%). ES/MS m/e ($^{79}$Br/$^{81}$Br) 304, 306 (M+1).

The following compounds in Table 37 are prepared essentially as described in the preparation of racemic (1RS,3SR,4RS)-3-amino-3-(3-bromo-4-fluorophenyl)-4-(hydroxymethyl)cyclopentanol.

TABLE 37

| Prep | Chemical name | ES/MS (m/e) (M + 1) |
|---|---|---|
| 59a | 3-Amino-3-(3-bromophenyl)-4-(hydroxymethyl)cyclopentanol[47] | ($^{79}$Br/$^{81}$Br) 286/288 |
| 59b | Racemic (1RS,3SR,4RS)-3-Amino-3-(5-bromo-2,4-difluorophenyl)-4-(hydroxymethyl)cyclopentanol | ($^{79}$Br/$^{81}$Br) 322/324 |
| 59c | (2-Amino-2-(3-bromophenyl)-4-methoxycyclopentyl)methanol[47] | ($^{79}$Br/$^{81}$Br) 300/302 |
| 59d | Racemic ((1RS,2SR,4RS)-2-Amino-2-(3-bromophenyl)-4-methoxycyclopentyl)methanol | ($^{79}$Br/$^{81}$Br) 300/302 |
| 59e | Racemic ((1RS,2SR,4RS)-2-Amino-2-(3-bromo-4-fluorophenyl)-4-methoxycyclopentyl)methanol | ($^{79}$Br/$^{81}$Br) 318/320 |
| 59f | Racemic ((1RS,2SR,4RS)-2-Amino-2-(3-bromo-4-fluorophenyl)-4-isopropoxycyclopentyl)methanol | ($^{79}$Br/$^{81}$Br) 346/348 |

[47]Isolated as a mixture of diastereomers.

Preparation 60

Racemic N-((1SR,2RS,4RS)-1-(3-Bromo-4-fluorophenyl)-4-hydroxy-2-(hydroxymethyl)cyclopentylcarbamothioyl)benzamide

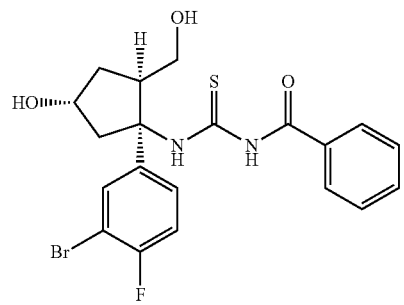

To a solution of racemic (1RS,3SR,4RS)-3-amino-3-(3-bromo-4-fluorophenyl)-4-(hydroxymethyl)cyclopentanol (0.48 g, 1.58 mmol) in THF (6.31 mL) is added benzoyl isothiocyanate (0.263 g, 1.58 mmol) and the mixture is stirred at room temperature for 1.5 h. The solvent is removed under reduced pressure and the crude product is purified by silica gel chromatography, eluting with a linear gradient of 0% to 10% methanol in dichloromethane over 20 minutes to give the title compound as racemic mixture (0.602 g, 76%). ES/MS m/e ($^{79}$Br/$^{81}$Br) 467, 469 (M+1).

The following compounds in Table 38 are prepared essentially as described in the preparation of racemic N-((1SR,2RS,4RS)-1-(3-bromo-4-fluorophenyl)-4-hydroxy-2-(hydroxymethyl)cyclopentylcarbamothioyl)benzamide.

TABLE 38

| Prep. No. | Chemical name | ES/MS (m/e) |
|---|---|---|
| 60a | N-(1-(3-Bromophenyl)-4-hydroxy-2-(hydroxymethyl)cyclopentylcarbamothioyl)benzamide[48] | ($^{79}$Br/$^{81}$Br) 449/451 (M + 1) |
| 60b | Racemic N-((1SR,2RS,4RS)-1-(5-Bromo-2,4-difluorophenyl)-4-hydroxy-2-(hydroxymethyl)cyclopentylcarbamothioyl)benzamide | ($^{79}$Br/$^{81}$Br) 485/487 (M + 1) |
| 60c | N-(1-(3-Bromophenyl)-2-(hydroxymethyl)-4-methoxycyclopentylcarbamothioyl)-benzamide[48] | ($^{79}$Br/$^{81}$Br) 463/465 (M + 1) |
| 60d | Racemic N-((1SR,2RS,4RS)-1-(3-Bromophenyl)-2-(hydroxymethyl)-4-methoxycyclopentylcarbamothioyl)-benzamide | ($^{79}$Br/$^{81}$Br) 463, 465 (M + 1) |
| 60e | Racemic N-((1SR,2RS,4RS)-1-(3-Bromo-4-fluorophenyl)-2-(hydroxymethyl)-4-methoxycyclopentylcarbamothioyl)benzamide | ($^{79}$Br/$^{81}$Br) 479, 481 (M − 1) |
| 60f | Racemic N-((1SR,2RS,4RS)-1-(3-Bromo-4-fluorophenyl)-2-(hydroxymethyl)-4-isopropoxycyclopentylcarbamothioyl)benzamide | ($^{79}$Br/$^{81}$Br) 507, 509 (M − 1) |

[48]Isolated as a mixture of diastereomers.

Preparation 61

Racemic N-((4aRS,6RS,7aSR)-7a-(3-Bromo-4-fluorophenyl)-6-hydroxy-4,4a,5,6,7,7a-hexahydrocyclopenta[d][1,3]thiazin-2-yl)benzamide

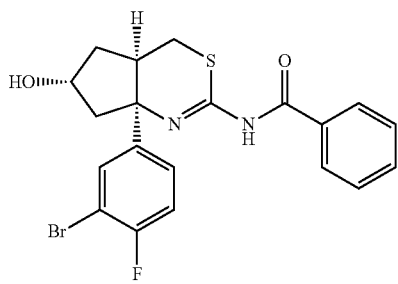

A solution of racemic N-((1SR,2RS,4RS)-1-(3-bromo-4-fluorophenyl)-4-hydroxy-2-(hydroxymethyl)cyclopentylcarbamothioyl)benzamide (1.21 g, 2.02 mmol) and triphenylphosphine (0.690 mg, 2.63 mmol) in anhydrous THF (18 mL) is added to a separate solution of di-tert-butyl azodicarboxylate (0.606 g, 2.63 mmol) in THF (36 mL) at room temperature. The reaction mixture is stirred at room temperature for 1 hr and concentrated under reduced pressure to give a residue that is purified by silica gel chromatography eluting with a linear gradient of 0% to 40% ethyl acetate in dichloromethane over 15 minutes to give the title compound as racemic mixture (0.557 g, 61%). ES/MS m/e ($^{79}$Br/$^{81}$Br) 449, 451 (M+1).

The following compounds in Table 39 are prepared essentially as described in the preparation of racemic N-((4aRS,6RS,7aSR)-7a-(3-bromo-4-fluorophenyl)-6-hydroxy-4,4a,5,6,7,7a-hexahydrocyclopenta[d][1,3]thiazin-2-yl)benzamide.

TABLE 39

| Prep | Chemical name | ES/MS (m/e) (M + 1) |
|---|---|---|
| 61a | Racemic N-((4aRS,6RS,7aSR)-7a-(3-Bromophenyl)-6-hydroxy-4,4a,5,6,7,7a-hexahydrocyclopenta[d][1,3]thiazin-2-yl)benzamide | ($^{79}$Br/$^{81}$Br) 431/433 |
| 61b | Racemic N-((4aRS,6RS,7aSR)-7a-(5-Bromo-2,4-difluorophenyl)-6-hydroxy-4,4a,5,6,7,7a-hexahydrocyclopenta[d][1,3]thiazin-2-yl)benzamide | ($^{79}$Br/$^{81}$Br) 467/469 |
| 61c | Racemic N-((4aRS,6RS,7aSR)-7a-(3-Bromophenyl)-6-methoxy-4,4a,5,6,7,7a-hexahydrocyclopenta[d][1,3]thiazin-2-yl)benzamide | ($^{79}$Br/$^{81}$Br) 445/447 |
| 61d | Racemic N-((4aRS,6SR,7aSR)-7a-(3-Bromophenyl)-6-methoxy-4,4a,5,6,7,7a-hexahydrocyclopenta[d][1,3]thiazin-2-yl)benzamide | ($^{79}$Br/$^{81}$Br) 445/447 |
| 61e | Racemic N-((4aRS,6RS,7aSR)-7a-(3-Bromo-4-fluorophenyl)-6-methoxy-4,4a,5,6,7,7a-hexahydrocyclopenta[d][1,3]thiazin-2-yl)benzamide | ($^{79}$Br/$^{81}$Br) 463/465 |
| 61f | Racemic N-((4aRS,6RS,7aSR)-7a-(3-Bromo-4-fluorophenyl)-6-isopropoxy-4,4a,5,6,7,7a-hexahydrocyclopenta[d][1,3]thiazin-2-yl)benzamide | ($^{79}$Br/$^{81}$Br) 491/493 |

Preparation 62

N-((4aR,6R,7aS)-7a-(3-Bromo-4-fluorophenyl)-6-hydroxy-4,4a,5,6,7,7a-hexahydrocyclopenta[d][1,3]thiazin-2-yl)benzamide

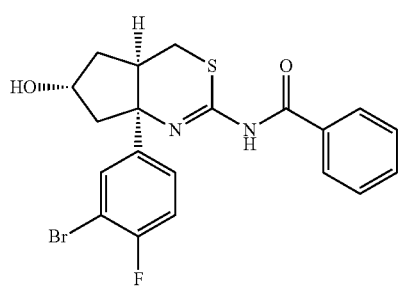

Racemic N-((4aRS,6RS,7aSR)-7a-(3-bromo-4-fluorophenyl)-6-hydroxy-4,4a,5,6,7,7a-hexahydrocyclopenta[d][1,3]thiazin-2-yl)benzamide (0.492 g, 1.09 mmol) is purified by chiral HPLC: Column: Chiralcel OJ-H 3×25 cm; eluent: 75:25 (methanol:acetonitrile); flow: 40 mL/min at UV 225 nm. The second eluting isomer is isolated to provide the enantiomerically enriched title compound (0.171 g, 35%). ES/MS m/e ($^{79}$Br/$^{81}$Br) 449, 451 (M+1).

The following compounds in Table 40 are prepared essentially as described in the preparation of N-((4aR,6R,7aS)-7a-(3-bromo-4-fluorophenyl)-6-hydroxy-4,4a,5,6,7,7a-hexahydrocyclopenta[d][1,3]thiazin-2-yl)benzamide

TABLE 40

| Prep | Chemical name | ES/MS (m/e) (M + 1) |
|---|---|---|
| 62a | N-((6R,7aS)-7a-(3-Bromo-4-fluorophenyl)-6-methoxy-4,4a,5,6,7,7a-hexahydrocyclopenta[d][1,3]thiazin-2-yl)benzamide | ($^{79}$Br/$^{81}$Br) 463/465 |

TABLE 40-continued

| Prep | Chemical name | ES/MS (m/e) (M + 1) |
|---|---|---|
| 62b | N-((4aR,6R,7aS)-7a-(3-Bromo-4-fluorophenyl)-6-isopropoxy-4,4a,5,6,7,7a-hexahydrocyclopenta[d][1,3]thiazin-2-yl)benzamide | ($^{79}$Br/$^{81}$Br) 491/493 |

Preparation 63

N-((4aR,6R,7aS)-7a-(4-Fluoro-3-(pyrimidin-5-yl)phenyl)-6-hydroxy-4,4a,5,6,7,7a-hexahydrocyclopenta[d][1,3]thiazin-2-yl)benzamide

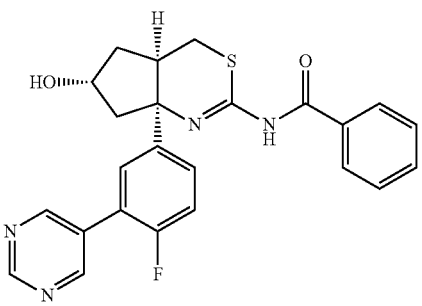

A solution of N-((4aR,6R,7aS)-7a-(3-bromo-4-fluorophenyl)-6-hydroxy-4,4a,5,6,7,7a-hexahydrocyclopenta[d][1,3]thiazin-2-yl)benzamide (0.588 g, 1.31 mmol) in a mixture of 1,2-dimethoxyethane (8 mL), ethanol (4 mL) and water (4 mL) is purged with nitrogen and is heated to 97° C. Pyrimidine-5-boronic acid (0.810 g, 6.54 mmol), cesium carbonate (2.56 g, 7.84 mmol) and bis(triphenylphosphine)palladium (II) chloride (0.184 g, 0.261 mmol) is added in a single portion and the reaction is heated at 97° C. for 30 minutes. The reaction is cooled, diluted with water and is extracted twice with ethyl acetate. The organic layer is dried over sodium sulfate and the crude product is purified by silica gel chromatography with a linear gradient of 0% to 40% ethyl acetate in dichloromethane over 20 minutes to give the title compound (0.464 g, 79%). ES/MS m/e: 449 (M+1).

The following compounds in Table 41 are prepared essentially as described in the preparation of N-((4aR,6R,7aS)-7a-(4-fluoro-3-(pyrimidin-5-yl)phenyl)-6-hydroxy-4,4a,5,6,7,7a-hexahydrocyclopenta[d][1,3]thiazin-2-yl)benzamide.

TABLE 41

| Prep | Chemical name | ES/MS (m/e) (M + 1) |
|---|---|---|
| 63a | N-((4aR,6R,7aS)-7a-(4-fluoro-3-(5-fluoropyridin-3-yl)phenyl)-6-hydroxy-4,4a,5,6,7,7a-hexahydrocyclopenta[d][1,3]thiazin-2-yl)benzamide[49] | 466 |
| 63b | Racemic N-((4aRS,6RS,7aSR)-7a-(3-(5-fluoropyridin-3-yl)phenyl)-6-hydroxy-4,4a,5,6,7,7a-hexahydrocyclopenta[d][1,3]thiazin-2-yl)benzamide | 448 |
| 63c | Racemic N-((4aRS,6RS,7aSR)-6-hydroxy-7a-(3-(pyrimidin-5-yl)phenyl)-4,4a,5,6,7,7a-hexahydrocyclopenta[d][1,3]thiazin-2-yl)benzamide | 431 |
| 63d | Racemic N-((4aRS,6RS,7aSR)-7a-(2,4-difluoro-5-(pyrimidin-5-yl)phenyl)-6-hydroxy-4,4a,5,6,7,7a-hexahydrocyclopenta[d][1,3]thiazin-2-yl)benzamide | 467 |
| 63e | Racemic N-((4aRS,6RS,7aSR)-6-methoxy-7a-(3-(pyrimidin-5-yl)phenyl)-4,4a,5,6,7,7a-hexahydrocyclopenta[d][1,3]thiazin-2-yl)benzamide | 445 |
| 63f | Racemic N-((4aRS,6RS,7aSR)-7a-(3-(5-fluoropyridin-3-yl)phenyl)-6-methoxy-4,4a,5,6,7,7a-hexahydrocyclopenta[d][1,3]thiazin-2-yl)benzamide | 462 |
| 63g | Racemic N-((4aRS,6SR,7aSR)-6-methoxy-7a-(3-(pyrimidin-5-yl)phenyl)-4,4a,5,6,7,7a-hexahydrocyclopenta[d][1,3]thiazin-2-yl)benzamide | 445 |
| 63h | N-((6R,7aS)-7a-(4-fluoro-3-(pyrimidin-5-yl)phenyl)-6-methoxy-4,4a,5,6,7,7a-hexahydrocyclopenta[d][1,3]thiazin-2-yl)benzamide | 463 |
| 63i | N-((4aR,6R,7aS)-7a-(4-fluoro-3-(pyrimidin-5-yl)phenyl)-6-isopropoxy-4,4a,5,6,7,7a-hexahydrocyclopenta[d][1,3]thiazin-2-yl)benzamide | 491 |
| 63j | Racemic N-((4aSR,7aSR)-7a-(3-(pyrimidin-5-yl)phenyl)-4a,5,7,7a-tetrahydro-4H-furo[3,4-d][1,3]thiazin-2-yl)benzamide | 417 |
| 63k | N-((4aS,7aS)-7a-(3-(pyrimidin-5-yl)phenyl)-4a,5,7,7a-tetrahydro-4H-furo[3,4-d][1,3]thiazin-2-yl)benzamide | 417 |
| 63m | Racemic N-((4aSR,7aSR)-7a-(2,4-difluoro-5-(pyrimidin-5-yl)phenyl)-4a,5,7,7a-tetrahydro-4H-furo[3,4-d][1,3]thiazin-2-yl)benzamide | 453 |
| 63n | N-((4aS,7aS)-7a-(2,4-difluoro-5-(pyrimidin-5-yl)phenyl)-4a,5,7,7a-tetrahydro-4H-furo[3,4-d][1,3]thiazin-2-yl)benzamide | 453 |
| 63p | N-((4aS,7aS)-7a-(2,4-difluoro-5-(5-fluoropyridin-3-yl)phenyl)-4a,5,7,7a-tetrahydro-4H-furo[3,4-d][1,3]thiazin-2-yl)benzamide | 470 |

[49] 2 N sodium carbonate solution is utilized instead of cesium carbonate.

Example 1

N-(3-((4aS,7aS)-2-Amino-4a,5,7,7a-tetrahydro-4H-furo[3,4-d][1,3]thiazin-7a-yl)-4-fluorophenyl)-5-fluoropicolinamide hydrochloride

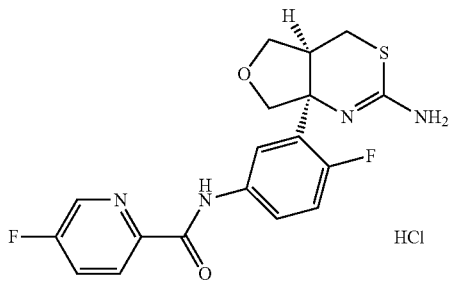

A solution of 4M hydrogen chloride in dioxane (834.8 μL; 3.3 mmol) is added to tert-butyl 7a-(5-(5-fluoropicolinamido)-2-fluorophenyl)-4a,5,7,7a-tetrahydro-4H-furo[3,4-d][1,3]thiazin-2-ylcarbamate (91 mg; 167.0 μmol) and stirred at ambient temperature. After 2 days, the reaction mixture is concentrated in vacuo. The residue is dissolved in minimal dichloromethane and methanol. Ether and hexane are added. The product is precipitated as the salt which is separated from the mother liquor by centrifugation and placed under vacuum to remove any solvent present to give the title compound (58 mg; 125 mmol). LC-ES/MS m/e 391 (M+1); $T_R$=1.675.

Example 1a

To a suspension of N-(3-((4aS,7aS)-2-amino-4a,5,7,7a-tetrahydro-4H-furo[3,4-d][1,3]thiazin-7a-yl)-4-fluorophenyl)-5-fluoropicolinamide (17.3 g, 42.10 mmol) in a mixture of ethanol (631.45 mL) and dichloromethane (420.96 mL) is added a solution of 4 M hydrogen chloride in 1,4-dioxane (46.31 mL, 185.22 mmol). The mixture is stirred at 22° C. for 1 h, concentrated and the residue is triturated with EtOH (200 mL). The solid is filtered off and washed with EtOH. The solid is triturated with water and the suspension is concentrated under reduced pressure. The residue is dried in a vacuum oven (18 h, 40° C.) to give the title compound as a white solid (17.1 g, 94%). ES/MS m/e: 391 (M+1).

Example 1b

N-(3-((4aS,7aS)-2-Amino-4a,5,7,7a-tetrahydro-4H-furo[3,4-d][1,3]thiazin-7a-yl)-4-fluorophenyl)-5-fluoropicolinamide To a suspension of N-(3-((4aS,7aS)-2-Amino-4a,5,7,7a-tetrahydro-4H-furo[3,4-d][1,3]thiazin-7a-yl)-4-fluorophenyl)-5-fluoropicolinamide hydrochloride (20 g, 47 mmol) in water (280 mL) at room temperature is added an aqueous solution of 2N sodium hydroxide (1.2 eq, 27 mL). The mixture is stirred for 30 minutes. The suspension is filtered and the solid is washed with water (3×100 mL). The solid is dried under vacuum at 45° C. to give the title compound as a white solid. The resulting solid is purified via the following two methods:

Method A: The solid (16 g) is suspended in 240 mL of water and an aqueous solution of 2N sodium hydroxide is added (1.5 eq, 31 mL). The mixture is placed in an ultrasound bath for 15 min at 22° C. and stirred at 22° C. for 3 h. The white solid is filtered, washed with water (3×100 mL), and dried in a vacuum oven at 45° C. overnight to yield the title compound (14 g). ES/MS m/e 391 (M+1).

Method B: The solid (3 g) is suspended in methanol (40 mL) and heated between 62 to 64° C. for 15 h with seeding with seeds of the free base of N-(3-((4aS,7aS)-2-Amino-4a,5,7,7a-tetrahydro-4H-furo[3,4-d][1,3]thiazin-7a-yl)-4-fluorophenyl)-5-fluoropicolinamide. The mixture is cooled to room temperature and the slurry is filtered. The solid is washed with methanol and dried in a vacuum oven at 50° C. for 4 h to yield the title compound (2.3 g). ES/MS m/e 391 (M+1).

Example 2

N-(3-((4aS,7aS)-2-Amino-4a,5,7,7a-tetrahydro-4H-furo[3,4-d][1,3]thiazin-7a-yl)-5-fluorophenyl)-5-fluoropicolinamide dihydrochloride

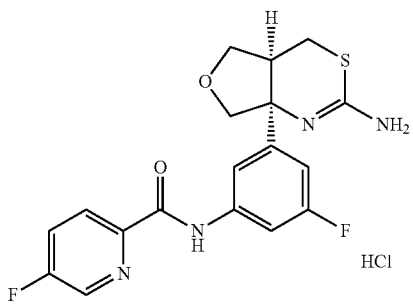

Pyridine (0.44 mL, 5.46 mmol) is added to a mixture of N-(3-((4aS,7aS)-2-benzamido-4a,5,7,7a-tetrahydro-4H-furo[3,4-d][1,3]thiazin-7a-yl)-5-fluorophenyl)-5-fluoropicolinamide (0.27 g, 0.546 mmol) and O-methylhydroxylamine hydrochloride (0.456 g, 5.46 mmol) in ethanol (15 mL). The resulting mixture is stirred at 50° C. for 6 h.

The mixture is cooled to room temperature and stirring is continued for 3 days. The mixture is diluted with dichloromethane and aqueous 0.1 M NaOH and is extracted five times with dichloromethane. The combined organic phase is diluted with MeOH to make a homogenous solution, dried over sodium sulfate, filtered, and the solvent is removed under reduced pressure to give a residue that is purified on silica gel with 5% methanol in dichloromethane to give the title compound as the freebase (0.109 g, 51%). Hydrogen chloride is bubbled through the solution of N-(3-((4aS,7aS)-2-amino-4a,5,7,7a-tetrahydro-4H-furo[3,4-d][1,3]thiazin-7a-yl)-5-fluorophenyl)-5-fluoropicolinamide (0.109 g, 0.279 mmol) in methanol for approximately 5 min. The solution is then concentrated under reduced pressure and dried on high vacuum to yield the title compound (0.128 g, 51%). ES/MS m/e: 391 (M+1)

The following compounds in Table 42 are prepared essentially as described in the preparation of N-(3-((4aS,7aS)-2-amino-4a,5,7,7a-tetrahydro-4H-furo[3,4-d][1,3]thiazin-7a-yl)-5-fluorophenyl)-5-fluoropicolinamide dihydrochloride.

TABLE 42

| Ex | Chemical name | Structure | ES/MS (m/e) (M + 1) |
|---|---|---|---|
| 3 | N-(3-((4aS,7aS)-2-Amino-4a,5,7,7a-tetrahydro-4H-furo[3,4-d][1,3]thiazin-7a-yl)phenyl)-5-fluoropicolinamide hydrochloride | 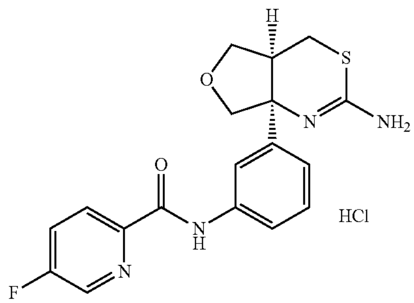 | 373 |
| 4 | Racemic N-(3-((4aSR,7aSR)-2-Amino-4a,5,7,7a-tetrahydro-4H-furo[3,4-d][1,3]thiazin-7a-yl)phenyl)-5-fluoropicolinamide hydrochloride | 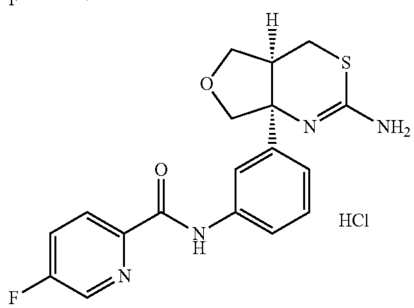 | 373 |

Example 5

N-(3-((8aS)-2-Amino-4,4a,5,7,8,8a-hexahydropyrano[4,3-d][1,3]thiazin-8a-yl)phenyl)-5-chloropicolinamide dihydrochloride

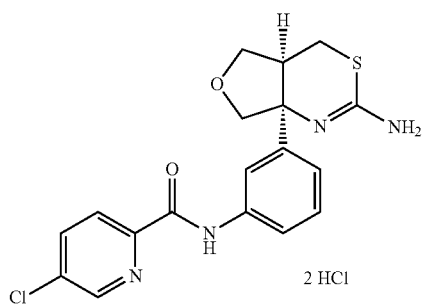

To a solution of tert-butyl (8aS)-8a-(3-(5-chloropicolinamido)phenyl)-4,4a,5,7,8,8a-hexahydropyrano[4,3-d][1,3]thiazin-2-ylcarbamate (0.172 g, 0.342 mmol) in $CH_2Cl_2$ (8 mL) is added TFA (4 mL) and the reaction is stirred at room temperature for 1 hour. The solvent is removed under reduced pressure. The residue is purified on a 10 g SCX column using 4:1 $CH_2Cl_2$:MeOH followed by 2:1 $CH_2Cl_2$: 7 N $NH_3$ in MeOH to afford the title compound as a freebase (0.127 g, 92%). The freebase (0.124 g, 0.308 mmol) is dissolved in $CH_2Cl_2$ and treated with 1 M HCl in $Et_2O$ (0.65 mL, 0.605 mmol) and the solvent is removed under reduced pressure to afford the title compound (0.127 g, 78%). ES/MS m/e ($^{35}Cl/^{37}Cl$) 403, 405 (M+1).

The following compounds in Table 43 are prepared essentially as described in the preparation of N-(3-((8aS)-2-amino-4,4a,5,7,8,8a-hexahydropyrano[4,3-d][1,3]thiazin-8a-yl)phenyl)-5-chloropicolinamide dihydrochloride.

TABLE 43

| Ex | Chemical name | Structure | ES/MS (m/e) (M + 1) |
|---|---|---|---|
| 6 | N-(3-((8aS)-2-Amino-4,4a,5,7,8,8a-hexahydropyrano[4,3-d][1,3]thiazin-8a-yl)-4-fluorophenyl)-5-chloropicolinamide hydrochloride | 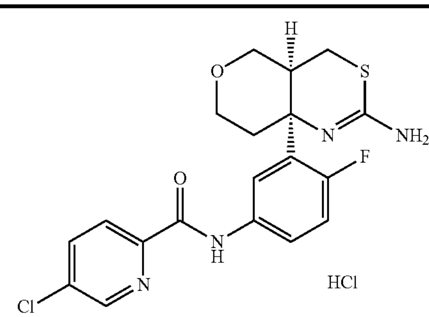 | ($^{35}Cl/^{37}Cl$) 421, 423 |

TABLE 43-continued

| Ex | Chemical name | Structure | ES/MS (m/e) (M + 1) |
|---|---|---|---|
| 7 | N-(3-((8aS)-2-Amino-4,4a,5,7,8,8a-hexahydropyrano[4,3-d][1,3]thiazin-8a-yl)-4-fluorophenyl)-5-fluoropicolinamide dihydrochloride | 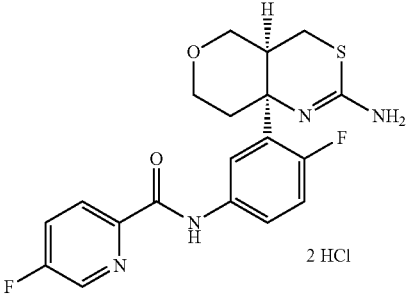 | 405 |
| 8 | N-(3-((8aS)-2-Amino-4,4a,5,7,8,8a-hexahydropyrano[4,3-d][1,3]thiazin-8a-yl)-4-fluorophenyl)thiazole-2-carboxamide hydrochloride | 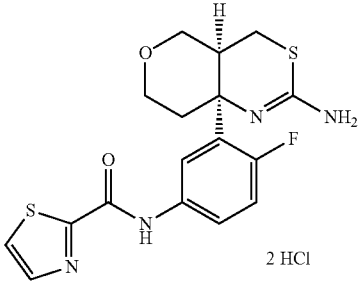 | 393 |
| 9 | N-(3-((8aS)-2-Amino-4,4a,5,7,8,8a-hexahydropyrano[4,3-d][1,3]thiazin-8a-yl)-4-fluorophenyl)picolinamide dihydrochloride | 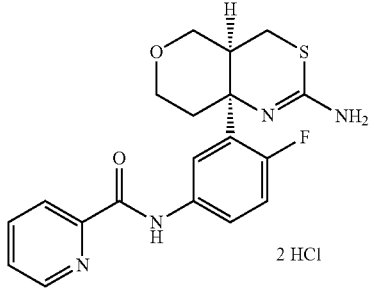 | 387 |
| 10 | N-(3-((8aS)-2-Amino-4,4a,5,7,8,8a-hexahydropyrano[4,3-d][1,3]thiazin-8a-yl)-4-fluorophenyl)-5-chloropyrimidine-2-carboxamide hydrochloride | 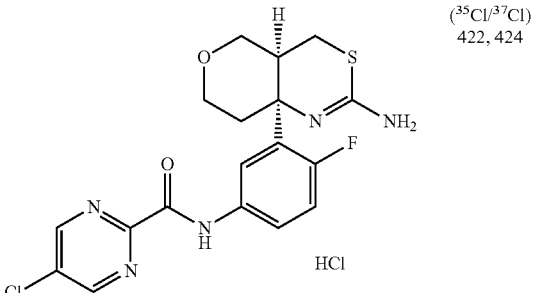 | ($^{35}$Cl/$^{37}$Cl) 422, 424 |
| 11 | N-(3-((8aS)-2-Amino-4,4a,5,7,8,8a-hexahydropyrano[4,3-d][1,3]thiazin-8a-yl)-4-fluorophenyl)-5-fluoropyrimidine-2-carboxamide hydrochloride | 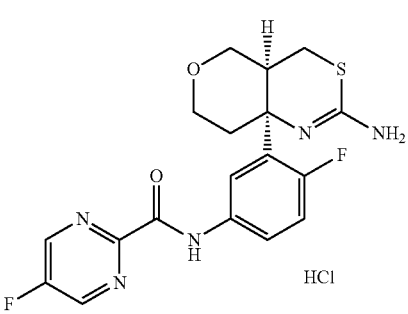 | 406 |

TABLE 43-continued

| Ex | Chemical name | Structure | ES/MS (m/e) (M + 1) |
|---|---|---|---|
| 12 | N-(5-((8aS)-2-Amino-4,4a,5,7,8,8a-hexahydropyrano[4,3-d][1,3]thiazin-8a-yl)-2-fluorophenyl)-5-chloropicolinamide dihydrochloride | 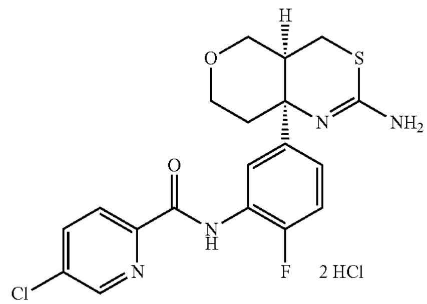 | ($^{35}$Cl/$^{37}$Cl) 421, 423 |
| 13 | N-(3-((8aS)-2-Amino-4,4a-5,7,8,8a-hexahydro-4H-benzo[d][1,3]thiazin-8a-yl)phenyl)-5-chloropicolinamide dihydrochloride | 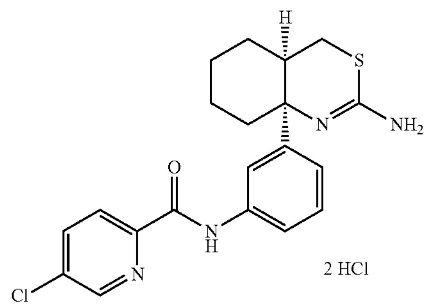 | ($^{35}$Cl/$^{37}$Cl) 401, 403 |
| 14 | N-(3-((4aR,7aS)-2-Amino-4,4a,5,6,7,7a-hexahydrocyclopenta[d][1,3]thiazin-7a-yl)phenyl)isonicotinamide dihydrochloride[50] | 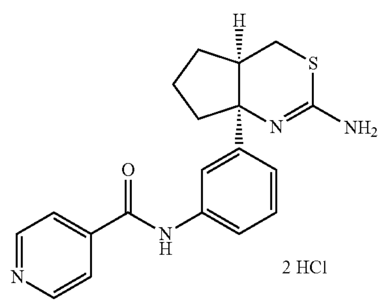 | 353 |
| 15 | N-(3-((4aR,7aS)-2-Amino-4,4a,5,6,7,7a-hexahydrocyclopenta[d][1,3]thiazin-7a-yl)phenyl)picolinamide dihydrochloride[50] | 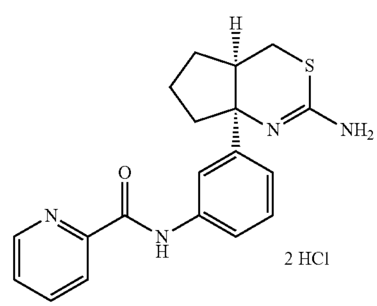 | 353 |
| 16 | N-(3-((7aS)-2-Amino-4,4a,5,6,7,7a-hexahydrocyclopenta[d][1,3]thiazin-7a-yl)phenyl)pyrazine-2-carboxamide dihydrochloride[50] | 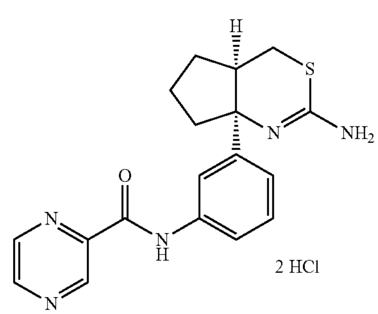 | 354 |

TABLE 43-continued

| Ex | Chemical name | Structure | ES/MS (m/e) (M + 1) |
|---|---|---|---|
| 17 | N-(3-((7aS)-2-Amino-4,4a,5,6,7,7a-hexahydrocyclopenta[d][1,3]thiazin-7a-yl)phenyl)pyrimidine-2-carboxamide dihydrochloride[50] | 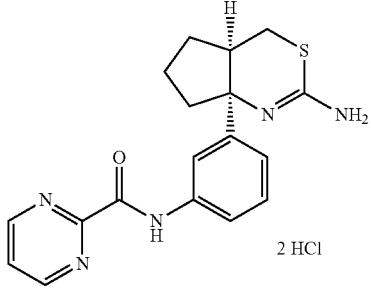 2 HCl | 354 |
| 18 | N-(3-((7aS)-2-Amino-4,4a,5,6,7,7a-hexahydrocyclopenta[d][1,3]thiazin-7a-yl)phenyl)benzamide hydrochloride[50] | 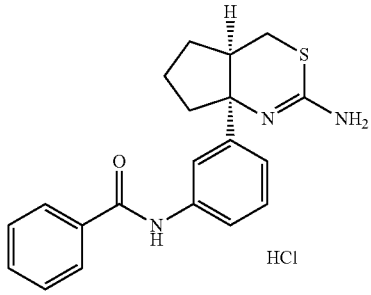 HCl | 352 |
| 19 | N-(3-((7aS)-2-Amino-4,4a,5,6,7,7a-hexahydrocyclopenta[d][1,3]thiazin-7a-yl)phenyl)pyrimidine-4-carboxamide dihydrochloride[50] | 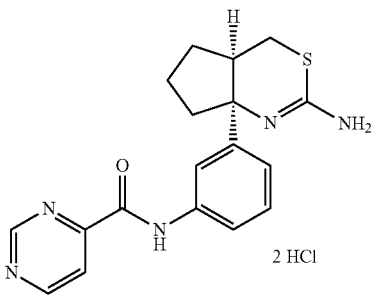 2 HCl | 354 |
| 20 | N-(3-((4aR,7aS)-2-Amino-4,4a,5,6,7,7a-hexahydrocyclopenta[d][1,3]thiazin-7a-yl)phenyl)-5-chloropicolinamide; hydrochloride[51] | 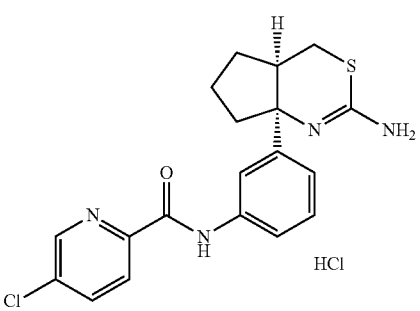 HCl | 387 |
| 21 | N-(3-((4aS,7aS)-2-Amino-4a,5,7,7a-tetrahydro-4H-furo[3,4-d][1,3]thiazin-7a-yl)-4-fluorophenyl)-5-chloropicolinamide dihydrochloride[50] | 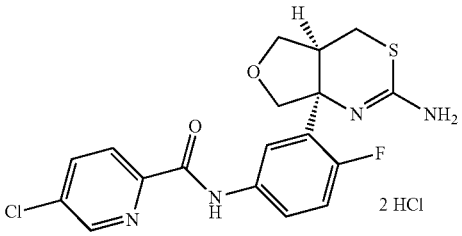 2 HCl | 407 |

TABLE 43-continued

| Ex | Chemical name | Structure | ES/MS (m/e) (M + 1) |
|----|---------------|-----------|---------------------|
| 22 | N-(3-((4aS,7aS)-2-Amino-4a,5,7,7a-tetrahydro-4H-furo[3,4-d][1,3]thiazin-7a-yl)-4-fluorophenyl)-5-fluoropyrimidine-2-carboxamide dihydrochloride[50] | 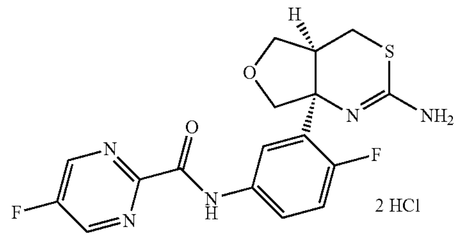 | 392 |

[50] 4 N HCl in 1,4-dioxane is utilized for deprotection instead of TFA to afford the HCl salt directly.
[51] HCl gas in dichloromethane/diethyl ether is utilized for deprotection instead of TFA to afford the HCl salt directly.

Example 23

(8aS)-8a-(2,4-Difluoro-5-(pyrimidin-5-yl)phenyl)-4,4a,5,7,8,8a-hexahydropyrano[4,3-d][1,3]thiazin-2-amine dihydrochloride

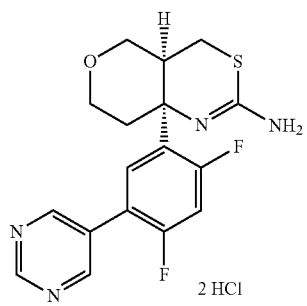

To a solution of tert-butyl 8a-(2,4-difluoro-5-(pyrimidin-5-yl)phenyl)-4,4a,5,7,8,8a-hexahydropyrano[4,3-d][1,3]thiazin-2-ylcarbamate (0.258 g, 0.558 mmol) in $CH_2Cl_2$ (8 mL) is added TFA (4 mL) and the reaction is stirred at room temperature for 1 hour. The solvent is removed under reduced pressure to afford a residue that is diluted with water and 1 N NaOH to adjust the pH to 12. The aqueous layer is extracted three times with EtOAc. The organic layer is dried over $Na_2SO_4$ and the crude product is purified by silica gel chromatography eluting with a linear gradient of 1% to 10% 7 N $NH_3$/MeOH in $CH_2Cl_2$ to afford the title compound as the freebase (0.165 g, 68%). The freebase (0.162 g, 0.448 mmol) is dissolved in $CH_2Cl_2$ and treated with of 1 M HCl in $Et_2O$ (0.94 mL, 0.940 mmol) and the solvent is removed under reduced pressure to afford the title compound (0.208 g, 86%). ES/MS m/e: 363 (M+1).

Example 24

(4aR,7aS)-7a-(3-(Pyrimidin-5-yl)phenyl)-4,4a,5,6,7,7a-hexahydrocyclopenta[d][1,3]thiazin-2-amine dihydrochloride

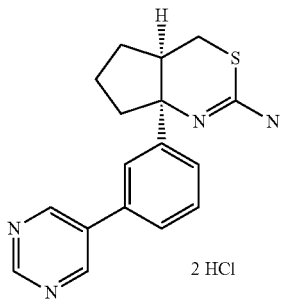

A mixture of tert-butyl (4aR,7aS)-7a-(3-bromophenyl)-4,4a,5,6,7,7a-hexahydrocyclopenta[d][1,3]thiazin-2-ylcarbamate (0.860 g, 2.09 mmol), pyrimidine-5-boronic acid (0.423 g, 3.34 mmol), (1,1'-bis(diphenylphosphino)ferrocene)palladium(II) chloride (0.171 g, 0.209 mmol) in 1,2-dimethoxyethane (10 mL) is heated to 100° C. under nitrogen atmosphere. Aqueous 2 M sodium carbonate (3.14 mL, 6.27 mmol) is added to the reaction mixture by syringe. The resulting mixture is stirred at 110° C. for 20 minutes. The reaction is cooled and extracted three times with dichloromethane and the combined extracts are dried over sodium sulfate, filtered, and concentrated under reduced pressure. The residue is purified by silica gel chromatography, eluting with a linear gradient of methanol in dichloromethane 0 to 20% over 30 minutes to give the title compound as a freebase (0.482 g, 74%). ES/MS m/e: 311 (M+1).

To the solution of (4aR,7aS)-7a-(3-(pyrimidin-5-yl)phenyl)-4,4a,5,6,7,7a-hexahydrocyclopenta[d][1,3]thiazin-2-amine (0.482 g, 1.55 mmol) in methanol (2 mL) is added 4 N HCl in 1,4-dioxane (2 mL) at room temperature. The resulting mixture is stirred at room temperature for 1 hour and is concentrated under reduced pressure to give the title compound (0.595 g, 100%). ES/MS m/e: 311 (M+1).

The following compound in Table 44 is prepared essentially as described in the preparation of (4aR,7aS)-7a-(3-(pyrimidin-5-yl)phenyl)-4,4a,5,6,7,7a-hexahydrocyclopenta[d][1,3]thiazin-2-amine dihydrochloride.

TABLE 44

| Ex | Chemical name | Structure | ES/MS (m/e) (M + 1) |
|----|---------------|-----------|---------------------|
| 25 | (8aS)-8a-(3-(Pyrimidin-5-yl)phenyl)-4a,5,6,7,8,8a-hexahydro-4H-benzo[d][1,3]thiazin-2-amine dihydrochloride | 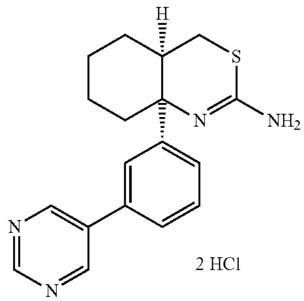 | 325 |

Example 26

(7aS)-7a-(4-Fluoro-3-(pyrimidin-5-yl)phenyl)-4,4-a,5,6,7,7a-hexahydrocyclopenta[d][1,3]thiazin-2-amine dihydrochloride

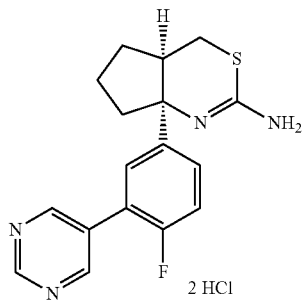

To a mixture of 5-((4aR,7aS)-2-(tert-butoxycarbonylamino)-4,4a,5,6,7,7a-hexahydrocyclopenta[d][1,3]thiazin-7a-yl)-2-fluorophenyl trifluoromethanesulfonate (0.630 g, 1.26 mmol), pyrimidin-5-ylboronic acid (0.189 g, 1.53 mmol), tricyclohexylphosphine (0.035 g, 0.125 mmol) and tris(dibenzylideneacetone)dipalladium (0) (0.057 g, 0.0622 mmol) in 1,4-dioxane (6 mL) is added 1.27 M aqueous potassium phosphate, tribasic, N-hydrate (1.76 mL, 2.24 mmol). The mixture is heated to 73° C. and stirred overnight. The reaction is cooled and diluted with water and EtOAc. The organic layer is dried over $Na_2SO_4$ and evaporated to dryness and the crude product is purified by silica gel chromatography eluting with a linear gradient of 1% to 10% 7 N $NH_3$/MeOH in $CH_2Cl_2$ to afford the title compound as the freebase (0.191 g, 46%). The freebase (0.191 g, 0.582 mmol) is dissolved in $CH_2Cl_2$ and treated with of 1 M HCl in $Et_2O$ (1.16 mL, 1.16 mmol) and the solvent is removed under reduced pressure to afford the title compound (0.24 g, 47.5%). ES/MS m/e: 329 (M+1).

Example 27

(4aR,6R,7aS)-2-Amino-7a-(3'-methoxybiphenyl-3-yl)-4,4a,5,6,7,7a-hexahydrocyclopenta[d][1,3]thiazin-6-ol hydrochloride

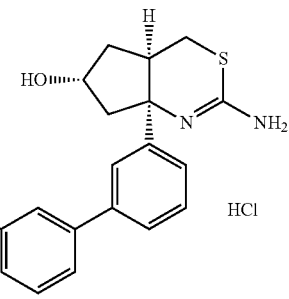

A mixture of N-((4aR,6R,7aS)-6-hydroxy-7a-(3'-methoxybiphenyl-3-yl)-4,4a,5,6,7,7a-hexahydrocyclopenta[d][1,3]thiazin-2-yl)benzamide (0.061 g, 0.133 mmol), o-methylhydroxylamine hydrochloride (0.111 g, 1.3 mmol) and pyridine (0.105 g, 1.30 mmol) in ethanol (5 mL) is heated to 50° C. for 15 h. The mixture is concentrated under reduced pressure. The crude product is purified by silica gel chromatography eluting with 0.5% to 10% $NH_3$ (7 N solution in methanol) in dichloromethane over 30 minutes to afford the title compound as a freebase (0.041 g, 87%). ES/MS m/e: 355 (M+1). A 1 N solution of HCl in $Et_2O$ (0.139 mL, 0.139 mmol) is added to a solution of (4aR,6R,7aS)-2-amino-7a-(3'-methoxybiphenyl-3-yl)-4,4a,5,6,7,7a-hexahydrocyclopenta[d][1,3]thiazin-6-ol (0.041 g, 0.116 mmol) in minimal dichloromethane and methanol. The solvent is removed under reduced pressure to give the title compound (0.045 g, 86%). ES/MS m/e: 355 (M+1).

The following compounds in Table 45 are prepared essentially as described in the preparation (4aR,6R,7aS)-2-amino-7a-(3'-methoxybiphenyl-3-yl)-4,4a,5,6,7,7a-hexahydrocyclopenta[d][1,3]thiazin-6-ol hydrochloride.

TABLE 45

| Ex | Chemical name | Structure | ES/MS (m/e) (M + 1) |
|---|---|---|---|
| 28 | (4aR,6R,7aS)-6-Methoxy-7a-(3'-methoxybiphenyl-3-yl)-4,4a,5,6,7,7a-hexahydrocyclopenta[d][1,3]thiazin-2-amine hydrochloride | 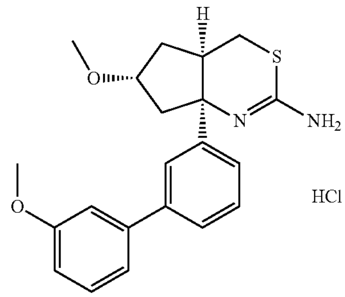 | 369 |
| 29 | (4aR,6R,7aS)-7a-(3'-Methoxybiphenyl-3-yl)-6-(methoxymethoxy)-4,4a,5,6,7,7a-hexahydrocyclopenta[d][1,3]thiazin-2-amine hydrochloride | 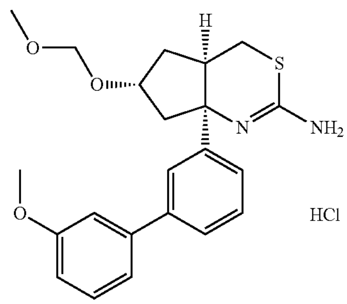 | 399 |
| 30 | (4aR,6R,7aS)-2-Amino-7a-(4-fluoro-3-(pyrimidin-5-yl)phenyl)-4,4a,5,6,7,7a-hexahydrocyclopenta[d][1,3]thiazin-6-ol dihydrochloride | 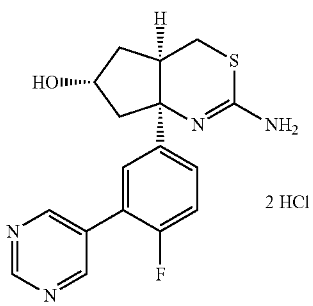 | 345 |
| 31 | 4aR,6R,7aS)-2-Amino-7a-(4-fluoro-3-(5-fluoropyridin-3-yl)phenyl)-4,4a,5,6,7,7a-hexahydrocyclopenta[d][1,3]thiazin-6-ol dihydrochloride | 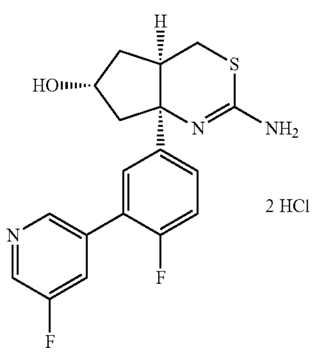 | 362 |
| 32 | Racemic (4aRS,6RS,7aSR)-2-Amino-7a-(3-(pyrimidin-5-yl)phenyl)-4,4a,5,6,7,7a-hexahydrocyclopenta[d][1,3]thiazin-6-ol dihydrochloride | 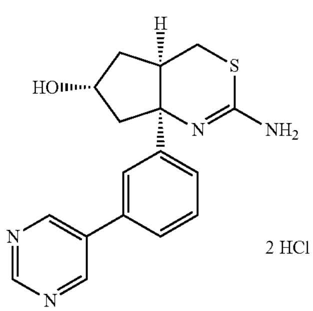 | 327 |

TABLE 45-continued

| Ex | Chemical name | Structure | ES/MS (m/e) (M + 1) |
|---|---|---|---|
| 33 | Racemix (4aRS,6RS,7aSR)-2-Amino-7a-(2,4-difluoro-5-(pyrimidin-5-yl)phenyl)-4,4a,5,6,7,7a-hexahydrocyclopenta[d][1,3]thiazin-6-ol dihydrochloride | 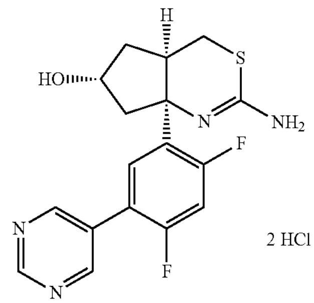 | 363 |
| 34 | Racemic (4aRS,6RS,7aSR)-2-Amino-7a-(3-(5-fluoropyridin-3-yl)phenyl)-4,4a,5,6,7,7a-hexahydrocyclopenta[d][1,3]thiazin-6-ol dihydrochloride | 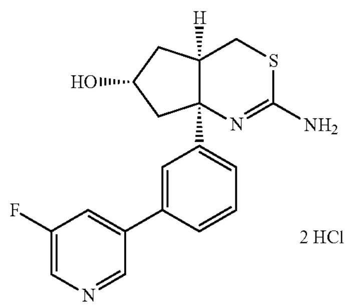 | 344 |
| 35 | Racemic (4aRS,6RS,7aSR)-6-Methoxy-7a-(3-(pyrimidin-5-yl)phenyl)-4,4a,5,6,7,7a-hexahydrocyclopenta[d][1,3]thiazin-2-amine | 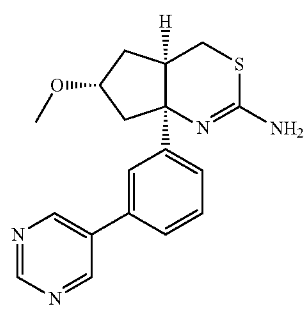 | 341 |
| 36 | Racemic (4aRS,6SR,7aSR)-6-Methoxy-7a-(3-(pyrimidin-5-yl)phenyl)-4,4a,5,6,7,7a-hexahydrocyclopenta[d][1,3]thiazin-2-amine | 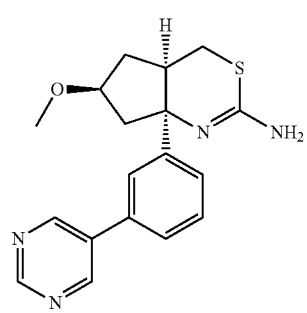 | 341 |
| 37 | Racemic (4aRS,6RS,7aSR)-7a-(3-(5-Fluoropyridin-3-yl)phenyl)-6-methoxy-4,4a,5,6,7,7a-hexahydrocyclopenta[d][1,3]thiazin-2-amine | 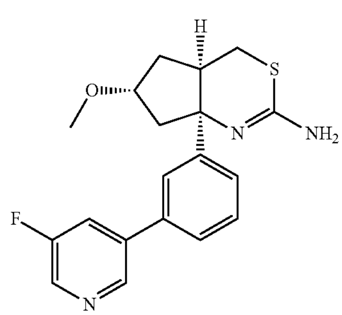 | 358 |

TABLE 45-continued

| Ex | Chemical name | Structure | ES/MS (m/e) (M + 1) |
|----|---------------|-----------|---------------------|
| 38 | (4aRS,6RS,7aSR)-7a-(4-fluoro-3-(pyrimidin-5-yl)phenyl)-6-methoxy-4,4a,5,6,7,7a-hexahydrocyclopenta[d][1,3]thiazin-2-amine dihydrochloride | 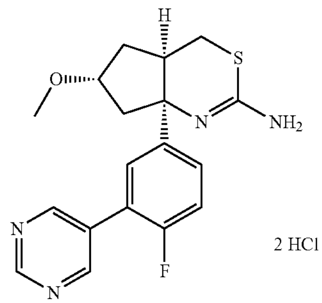 | 359 |
| 39 | Racemic (4aSR,7aSR)-7a-(3-(Pyrimidin-5-yl)phenyl)-4a,5,7,7a-tetrahydro-4H-furo[3,4-d][1,3]thiazin-2-amine dihydrochloride | 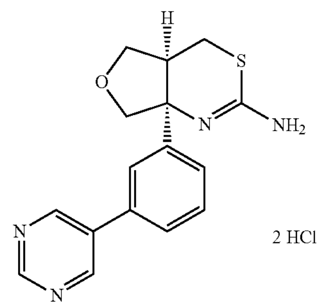 | 313 |
| 40 | (4aS,7aS)-7a-(3-(Pyrimidin-5-yl)phenyl)-4a,5,7,7a-tetrahydro-4H-furo[3,4-d][1,3]thiazin-2-amine dihydrochloride | 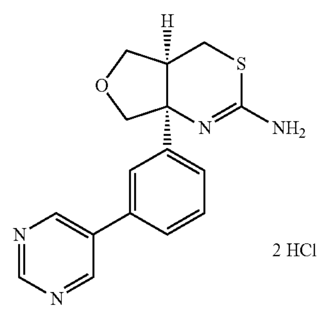 | 313 |
| 41 | (4aR,6R,7aS)-7a-(4-Fluoro-3-(pyrimidin-5-yl)phenyl)-6-isopropoxy-4,4a,5,6,7,7a-hexahydrocyclopenta[d][1,3]thiazin-2-amine dihydrochloride | 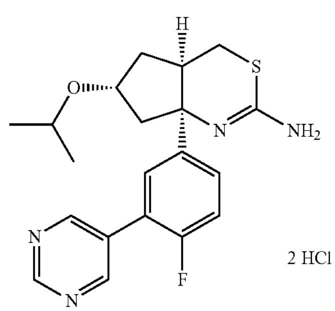 | 387 |

Example 42

(4aS,7aS)-7a-(2,4-Difluoro-5-(5-fluoropyridin-3-yl)phenyl)-4a,5,7,7a-tetrahydro-4H-furo[3,4-d][1,3]thiazin-2-amine dihydrochloride

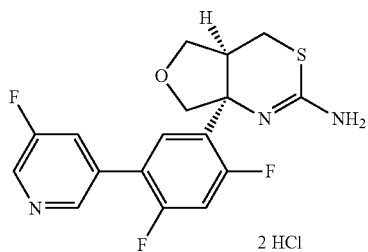

N Aqueous hydrochloric acid (8.70 mL) is added to N-((4aS,7aS)-7a-(2,4-difluoro-5-(5-fluoropyridin-3-yl)phenyl)-4a,5,7,7a-tetrahydro-4H-furo[3,4-d][1,3]thiazin-2-yl)benzamide (0.252 g, 0.435 mmol) in methanol (4 mL) and the mixture is heated to 90° C. After 18 hours, the heat is removed and the pH of the reaction mixture is adjusted to basic with 5 N aqueous sodium hydroxide. The mixture is extracted three times with 10% isopropyl alcohol in dichloromethane. The organic layer is concentrated under reduced pressure and the resulting residue is purified by radial chromatography eluting with 3% 2 M ammonia in methanol:dichloromethane to give the title compound as the freebase. The free base is dissolved in minimal dichloromethane and 1 M hydrogen chloride in ether is added in excess. Hexane (1 mL) is added and the solvent is removed under reduced pressure to give the title compound (0.129 g, 67%). ES/MS m/e: 366 (M+1).

The following compounds in Table 46 are prepared essentially by the method of (4aS,7aS)-7a-(2,4-difluoro-5-(5-fluoropyridin-3-yl)phenyl)-4a,5,7,7a-tetrahydro-4H-furo[3,4-d][1,3]thiazin-2-amine dihydrochloride.

Example 45

(4aS,7aS)-7a-(4-Fluoro-3-(pyrimidin-5-yl)phenyl)-4a,5,7,7a-tetrahydro-4H-furo[3,4-d][1,3]thiazin-2-amine dihydrochloride

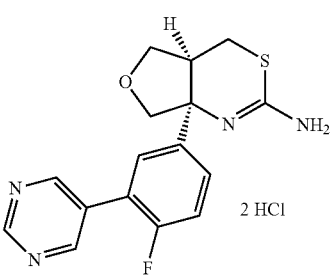

A solution of 1 M hydrogen chloride in diethyl ether is added in excess to (4aS,7aS)-7a-(4-fluoro-3-(pyrimidin-5-yl)phenyl)-4a,5,7,7a-tetrahydro-4H-furo[3,4-d][1,3]thiazin-2-amine (22 mg, 66.59 mmol) in minimal dichloromethane. The solvent is removed under reduced pressure to give the title compound (27 mg, 100%). LC-ES/MS m/e: 331 (M+1).

The following compounds in Table 47 are prepared essentially by the method of (4aS,7aS)-7a-(4-fluoro-3-(pyrimidin-5-yl)phenyl)-4a,5,7,7a-tetrahydro-4H-furo[3,4-d][1,3]thiazin-2-amine dihydrochloride.

TABLE 46

| Ex | Chemical name | Structure | MS (m/e) (M + 1) |
|----|---------------|-----------|------------------|
| 43 | Racemic (4aSR,7aSR)-7a-(2,4-Difluoro-5-(pyrimidin-5-yl)phenyl)-4a,5,7,7a-tetrahydro-4H-furo[3,4-d][1,3]thiazin-2-amine dihydrochloride | 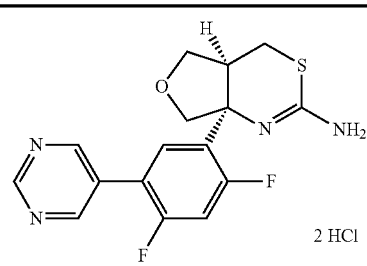 | 349 |
| 44 | (4aS,7aS)-7a-(2,4-Difluoro-5-(Pyrimidin-5-yl)phenyl)-4a,5,7,7a-tetrahydro-4H-furo[3,4-d][1,3]thiazin-2-amine dihydrochloride | 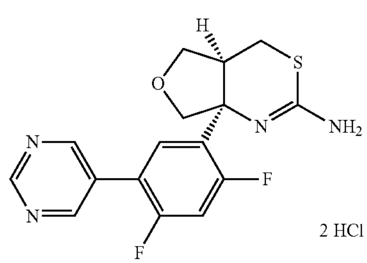 | 349 |

TABLE 47

| Ex | Chemical name | Structure | MS (m/e) (M + 1) |
|----|---------------|-----------|------------------|
| 46 | (4aS,7aS)-7a-(2-Fluoro-5-(pyrimidin-5-yl)phenyl)-4a,5,7,7a-tetrahydro-4H-furo[3,4-d][1,3]thiazin-2-aminedihydrochloride | (structure; 2 HCl) | 331 |

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 mM to 1 nM in a 96-well round-bottom plate before conducting the in vitro enzymatic and whole cell assays.

In Vitro Protease Inhibition Assays

BACE1 FRET Assay

Serial dilutions of test compounds are prepared as described above. Compounds are further diluted 20× in $KH_2PO_4$ buffer. Ten μL of each dilution is added to each well on row A to H of a corresponding low protein binding black plate containing the reaction mixture (25 μL of 50 mM $KH_2PO_4$, pH 4.6, 1 mM TRITON® X-100, 1 mg/mL Bovine Serum Albumin, and 15 μM of FRET substrate) (See Yang, et. al., *J. Neurochemistry*, 91(6) 1249-59 (2004)). The content is mixed well on a plate shaker for 10 minutes. Fifteen μL of two hundred pM human BACE1(1-460):Fc (See Vasser, et al., *Science*, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $EC_{50}$ and $IC_{50}$ values. (See Sinha, et al., *Nature*, 402, 537-540 (2000)).

The compounds exemplified herein were tested essentially as described above and exhibited an $IC_{50}$ value for BACE1 of lower than 1 μM. The following exemplified compounds were tested essentially as described above and exhibited the following activity for BACE1:

TABLE 48

| EXAMPLE | BACE1 $IC_{50}$ (nM) |
|---------|----------------------|
| 1 | 20.3 |
| 8 | 179 |
| 32 | 346 |
| 25 | 731 |

These data demonstrate that the compounds of Table 48 inhibit purified recombinant BACE1 enzyme activity in vitro.

Expression of Human BACE1

Human BACE1 (accession number: AF190725) is cloned from total brain cDNA by room temperature-PCR. The nucleotide sequences corresponding to amino acid sequences #1 to 460 are inserted into the cDNA encoding human $IgG_1$ (Fc) polypeptide (Vassar et al. 1999). This fusion protein of BACE1(1-460) and human Fc, named huBACE1:Fc, is constructed into the pJB02 vector. Human BACE1(1-460):Fc (huBACE1:Fc) is transiently expressed in HEK293 cells. 250 μg cDNA of each construct is mixed with Fugene 6 and added to 1 liter HEK293 cells. Four days after the transfection, conditioned media are harvested for purification.

Purification of huBACE1:Fc huBACE1:Fc is purified by Protein A chromatography. The enzyme is stored at −80° C. in small aliquots.

Whole Cell Assays for Measuring the Inhibition of Beta-Secretase Activity

HEK293Swe Whole Cell Assay

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met652 to Asn651Leu652, commonly called the Swedish mutation (noted HEK293/APP751sw) and shown to overproduce Abeta (Citron, et al., *Nature*, 360, 672-674 (1992)). In vitro Abeta reduction assays have been described in the literature (See Dovey, et al., *Journal of Neurochemistry*, 76, 173-181 (2001); Seubert, et al., *Nature*, 361, 260 (1993); and Johnson-Wood, et al., *Proc. Natl. Acad. Sci. USA*, 94, 1550-1555 (1997)).

Cells (HEK293/APP751sw at $3.5 \times 10^4$ cells/well, containing 200 μL culture media, DMEM containing 10% FBS) are incubated at 37° C. for 4 to 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 49

| EXAMPLE | HEK 293 Swe A-beta (1-40) ELISA $IC_{50}$ (nM) | HEK 293 Swe A-beta (1-42) ELISA $IC_{50}$ (nM) |
| --- | --- | --- |
| 1 | 18.5 | 19.7 |
| 8 | 78.0 | 89.6 |
| 32 | 670 | 173 |
| 25 | 1360 | 1150 |

These data demonstrate that the compounds of Table 49 inhibit native endogenous human BACE1 in cells in vitro.

PDAPP Primary Neuronal Assay

A confirmatory whole cell assay is also run in primary neuronal cultures generated from PDAPP transgenic embryonic mice. Primary cortical neurons are prepared from Embryonic Day 16 PDAPP embryos and cultured in 96 well plates ($15 \times 10^4$ cells/well in DMEM/F12 (1:1) plus 10% FBS). After 4-6 days in vitro, culture media is replaced with serum free DMEM/F12 (1:1) containing B27 supplement and neurons are incubated at 37° C. for 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 50

| EXAMPLE | PDAPP Neuron A-beta (1-40) ELISA $IC_{50}$ (nM) | PDAPP Neuron A-beta (1-42) ELISA $IC_{50}$ (nM) |
| --- | --- | --- |
| 1 | 10.7 | 9.23 |
| 8 | 32.8 | 41.3 |
| 32 | 436 | 352 |
| 25 | 734 | 659 |

These data demonstrate that the compounds of Table 50 inhibit native, endogenous murine BACE1 in cells in vitro.

In Vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Games et al., Nature 373, 523-527 (1995), and other non-transgenic or gene knockout animals are useful to analyze in vivo inhibition of Abeta and sAPPbeta production in the presence of inhibitory compounds. Generally, 2 to 12 month old PDAPP mice, gene knockout mice or non-transgenic animals are administered compound formulated in vehicles, such as corn oil, cyclodextran, phosphate buffers, PHARMASOLVE®, or other suitable vehicles. One to twenty-four hours following the administration of compound, animals are sacrificed, and brains as well as cerebrospinal fluid and plasma are removed for analysis of Abetas, C99, and sAPP fragments. (See Dovey, et al., Journal of Neurochemistry, 76, 173-181 (2001); and Johnson-Wood, et al., Proc. Natl. Acad. Sci. USA, 94, 1550-1555 (1997)).

For standard in vivo pharmacology studies, animals are dosed with various concentrations of compound and compared to a vehicle-treated control group dosed at the same time. For some time course studies, brain tissue, plasma, or cerebrospinal fluid is obtained from selected animals, beginning at time 0 to establish a baseline. Compound is administered to other groups and sacrificed at various times after dosing. Brain tissue, plasma, or cerebrospinal fluid is obtained from selected animals and analyzed for the presence of APP cleavage products, including Abeta peptides, sAPPbeta, and other APP fragments, for example, by specific sandwich ELISA assays. At the end of the test period, animals are sacrificed and brain tissues, plasma, or cerebrospinal fluid are analyzed for the presence of Abeta peptides, C99, and sAPPbeta, as appropriate. Brain tissues of APP transgenic animals are also analyzed for the amount of beta-amyloid plaques following compound treatment.

Animals (PDAPP or other APP transgenic or non-transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls or time zero controls. For example, 3 hours after administration of 10 mg/kg subcutaneous dose of the compound of Example 1 to young female PDAPP mice, Abeta 1-x peptide, C99 and sAPPb levels are reduced approximately 64%, 60%, and 44% in brain cortex, respectively, compared to vehicle-treated mice. Similarly, 3 hours after administration of a 10 mg/kg oral dose of the compound of Example 1 to young female PDAPP mice, Abeta 1-x peptide, C99 and sAPPb levels are reduced approximately 54%, 34% and 42% in brain cortex, respectively, compared to vehicle-treated mice. Consistent with changes in brain Abeta, C99 and sAPPb, 3 hours after oral administration of a 10 mg/kg dose of the compound of Example 1, CSF Abeta 1-x and 1-42 levels are reduced by approximately 62% and 62%, respectively. Consistent with a mechanism of BACE inhibition in vivo, CSF sAPPbeta levels are reduced 22%, while CSF sAPPalpha levels are unchanged 3 hours after oral administration of a 10 mg/kg dose of the compound of Example 1.

The compounds of the present invention are preferably formulated as pharmaceutical compositions administered by a variety of routes. Most preferably, such compounds are for oral administration. Such pharmaceutical compositions and processes for preparing same are well known in the art. See, e.g., Remington: *The Science and Practice of Pharmacy* (A. Gennaro, et. al., eds., 19$^{th}$ ed., Mack Publishing Co., 1995).

The compounds of Formula I are generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound which is N-(3-((4aS,7aS)-2-amino-4a,5,7,7a-tetrahydro-4H-furo[3,4-d][1,3]thiazin-7a-yl)-4-fluorophenyl)-5-fluoropicolinamide:

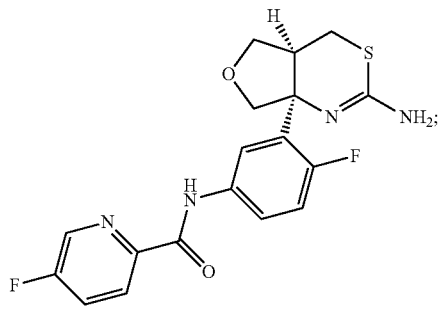

or a pharmaceutically acceptable salt thereof.

* * * * *